(12) United States Patent
Hannedouche et al.

(10) Patent No.: US 7,824,866 B2
(45) Date of Patent: Nov. 2, 2010

(54) LIGAND FOR G-PROTEIN COUPLED RECEPTOR GPR72 AND USES THEREOF

(75) Inventors: Sebastien Hannedouche, Brussels (BE); Marie-Odile Roy, Brussels (BE)

(73) Assignee: Euroscreen S.A., Brussels (BE)

( * ) Notice: Subject to any disclaimer, the term of this patent is extended or adjusted under 35 U.S.C. 154(b) by 0 days.

(21) Appl. No.: 11/811,961

(22) Filed: Jun. 12, 2007

(65) Prior Publication Data

US 2008/0274124 A1      Nov. 6, 2008

(30) Foreign Application Priority Data

Jun. 13, 2006     (EP) .................................. 06447078

(51) Int. Cl.
*G01N 33/566* (2006.01)
*C07K 14/705* (2006.01)

(52) U.S. Cl. ...................... 435/7.1; 435/7.2; 435/7.21; 436/501

(58) Field of Classification Search ....................... None
See application file for complete search history.

(56) References Cited

U.S. PATENT DOCUMENTS

| 2003/0129664 A1* | 7/2003 | Ahmad et al. ................. 435/7.2 |
| 2005/0130937 A1 | 6/2005 | Ben Dror et al. |
| 2006/0035974 A1 | 2/2006 | Yun et al. |
| 2007/0122845 A1 | 5/2007 | Kawano et al. |

FOREIGN PATENT DOCUMENTS

| EP | 0877083 A1 | 11/1998 |
| WO | WO-01/44439 | 6/2001 |
| WO | WO-02/075273 | 9/2002 |
| WO | WO 03/065044 A2 | 8/2003 |

OTHER PUBLICATIONS

Hansen et al., G Protein-Coupled Receptor 83 Overexpressed in Naive CD4+ CD25-- T Cells Leads to the Induction of Foxp3+ Regulatory T Cells In Vivo, Jul. 1, 2006, Journal of Immunology 177:209-215.*

Itoh et al., "GPR40, a free fatty acid receptor on pancreatic beta cells, regulates insulin secretion" Hepatology Research, Amsterdam, NL, vol. 33, No. 2, Oct. 2005, pp. 171-173, XP005180997.

McAllister Sean D et al, "CB1 and CB2 receptor-mediated signaling: A focus on endocannabinoids" Prostaglandins Leukotrienes and Essential Fatty Acids, vol. 66, No. 2-3, Feb. 2002, pp. 161-171, XP002411710.

* cited by examiner

*Primary Examiner*—John D Ulm
(74) *Attorney, Agent, or Firm*—Edwards Angell Palmer & Dodge LLP; Kathleen Williams; Amy DeCloux

(57) ABSTRACT

The present invention relates to methods, reagents and kits for detecting of GPR72 polypeptide activity in a sample and identifying agents which modulate polypeptide activity. It further relates to antibodies raised against GPR72. It further relates to substances for preventing, treating and/or alleviating diseases or disorders characterized by dysregulation of GPR72 polypeptide signalling.

19 Claims, 16 Drawing Sheets

FIGURE 1A Figure 1A and Figure 1B represents nucleotide sequence (SEQ ID NO:1) as cloned in pEFIN3 and deduced amino acid sequence (SEQ ID NO:2) of the human GPR72 receptor. The starts and stops codons are indicated in bold.

```
  1 ATG GTC CCT CAC CTC TTG CTG CTC TGT CTC CTC CCC TTG GTG CGA   45
  1  M   V   P   H   L   L   L   L   C   L   L   P   L   V   R    15

46 GCC ACC GAG CCC CAC GAG GGC CGG GCC GAC GAG CAG AGC GCG GAG   90
 16  A   T   E   P   H   E   G   R   A   D   E   Q   S   A   E    30

91 GCG GCC CTG GCC GTG CCC AAT GCC TCG CAC TTC TTC TCT TGG AAC  135
 31  A   A   L   A   V   P   N   A   S   H   F   F   S   W   N    45

136 AAC TAC ACC TTC TCC GAC TGG CAG AAC TTT GTG GGC AGG AGG CGC  180
 46  N   Y   T   F   S   D   W   Q   N   F   V   G   R   R   R    60

181 TAC GGC GCT GAG TCC CAG AAC CCC ACG GTG AAA GCC CTG CTC ATT  225
 61  Y   G   A   E   S   Q   N   P   T   V   K   A   L   L   I    75

226 GTG GCT TAC TCC TTC ATC ATT GTC TTC TCA CTC TTT GGC AAC GTC  270
 76  V   A   Y   S   F   I   I   V   F   S   L   F   G   N   V    90

271 CTG GTC TGT CAT GTC ATC TTC AAG AAC CAG CGA ATG CAC TCG GCC  315
 91  L   V   C   H   V   I   F   K   N   Q   R   M   H   S   A   105

316 ACC AGC CTC TTC ATC GTC AAC CTG GCA GTT GCC GAC ATA ATG ATC  360
106  T   S   L   F   I   V   N   L   A   V   A   D   I   M   I   120

361 ACG CTG CTC AAC ACC CCC TTC ACT TTG GTT CGC TTT GTG AAC AGC  405
121  T   L   L   N   T   P   F   T   L   V   R   F   V   N   S   135

406 ACA TGG ATA TTT GGG AAG GGC ATG TGC CAT GTC AGC CGC TTT GCC  450
136  T   W   I   F   G   K   G   M   C   H   V   S   R   F   A   150

451 CAG TAC TGC TCA CTG CAC GTC TCA GCA CTG ACA CTG ACA GCC ATT  495
151  Q   Y   C   S   L   H   V   S   A   L   T   L   T   A   I   165

496 GCG GTG GAT CGC CAC CAG GTC ATC ATG CAC CCC TTG AAA CCC CGG  540
166  A   V   D   R   H   Q   V   I   M   H   P   L   K   P   R   180

541 ATC TCA ATC ACA AAG GGT GTC ATC TAC ATC GCT GTC ATC TGG ACC  585
181  I   S   I   T   K   G   V   I   Y   I   A   V   I   W   T   195

586 ATG GCT ACG TTC TTT TCA CTC CCA CAT GCT ATC TGC CAG AAA TTA  630
196  M   A   T   F   F   S   L   P   H   A   I   C   Q   K   L   210

631 TTT ACC TTC AAA TAC AGT GAG GAC ATT GTG CGC TCC CTC TGC CTG  675
211  F   T   F   K   Y   S   E   D   I   V   R   S   L   C   L   225

676 CCA GAC TTC CCT GAG CCA GCT GAC CTC TTC TGG AAG TAC CTG GAC  720
226  P   D   F   P   E   P   A   D   L   F   W   K   Y   L   D   240

721 TTG GCC ACC TTC ATC CTG CTC TAC ATC CTG CCC CTC CTC ATC ATC  765
241  L   A   T   F   I   L   L   Y   I   L   P   L   L   I   I   255
```

FIGURE 1B

```
 766 TCT GTG GCC TAC GCT CGT GTG GCC AAG AAA CTG TGG CTG TGT AAT  810
 256  S   V   A   Y   A   R   V   A   K   K   L   W   L   C   N   270

811 ATG ATT GGC GAT GTG ACC ACA GAG CAG TAC TTT GCC CTG CGG CGC  855
 271  M   I   G   D   V   T   T   E   Q   Y   F   A   L   R   R   285

856 AAA AAG AAG AAG ACC ATC AAG ATG TTG ATG CTG GTG GTA GTC CTC  900
 286  K   K   K   K   T   I   K   M   L   M   L   V   V   V   L   300

901 TTT GCC CTC TGC TGG TTC CCC CTC AAC TGC TAC GTC CTC CTC CTG  945
 301  F   A   L   C   W   F   P   L   N   C   Y   V   L   L   L   315

946 TCC AGC AAG GTC ATC CGC ACC AAC AAT GCC CTC TAC TTT GCC TTC  990
 316  S   S   K   V   I   R   T   N   N   A   L   Y   F   A   F   330

991 CAC TGG TTT GCC ATG AGC AGC ACC TGC TAT AAC CCC TTC ATA TAC 1035
 331  H   W   F   A   M   S   S   T   C   Y   N   P   F   I   Y   345

1036 TGC TGG CTG AAC GAG AAC TTC AGG ATT GAG CTA AAG GCA TTA CTG 1080
 346  C   W   L   N   E   N   F   R   I   E   L   K   A   L   L   360

1081 AGC ATG TGT CAA AGA CCT CCC AAG CCT CAG GAG GAC AGG CCA CCC 1125
 361  S   M   C   Q   R   P   P   K   P   Q   E   D   R   P   P   375

1126 TCC CCA GTT CCT TCC TTC AGG GTG GCC TGG ACA GAG AAG AAT GAT 1170
 376  S   P   V   P   S   F   R   V   A   W   T   E   K   N   D   390

1171 GGC CAG AGG GCT CCC CTT GCC AAT AAC CTC CTG CCC ACC TCC CAA 1215
 391  G   Q   R   A   P   L   A   N   N   L   L   P   T   S   Q   405

1216 CTC CAG TCT GGG AAG ACA GAC CTG TCA TCT GTG GAA CCC ATT GTG 1260
 406  L   Q   S   G   K   T   D   L   S   S   V   E   P   I   V   420

1261 ACG ATG AGT TAG                                              1272
 421  T   M   S   *                                               424
```

Figure 2A Figures 2A and 2B represent nucleotide sequence (SEQ ID NO:3) as cloned in pEFIN3 and deduced amino acid sequence (SEQ ID NO:4) of the mouse GPR72 receptor. The starts and sotps codons are indicated in bold.

```
  1 ATG AAG GTT CCT CCT GTC CTG CTT CTC TTT CTT CTG TCC TCA GTG   45
  1  M   K   V   P   P   V   L   L   L   F   L   L   S   S   V   15

46 CGA GCT ACT GAG CAA CCG CAG GTC GTC ACT GAG CAT CCC AGC ATG   90
 16  R   A   T   E   Q   P   Q   V   V   T   E   H   P   S   M   30

91 GAG GCA GCC CTG ACC GGG CCC AAC GCC TCC TCG CAC TTC TGG GCC  135
 31  E   A   A   L   T   G   P   N   A   S   S   H   F   W   A   45

136 AAC TAC ACT TTC TCT GAC TGG CAG AAC TTC GTG GGC AGG AGA CGT  180
 46  N   Y   T   F   S   D   W   Q   N   F   V   G   R   R   R   60

181 TAT GGG GCC GAG TCC CAG AAC CCC ACG GTG AAA GCA CTG CTC ATC  225
 61  Y   G   A   E   S   Q   N   P   T   V   K   A   L   L   I   75

226 GTG GCC TAC TCA TTC ACC ATC GTC TTC TCG CTC TTC GGT AAT GTC  270
 76  V   A   Y   S   F   T   I   V   F   S   L   F   G   N   V   90

271 CTG GTC TGT CAT GTC ATC TTC AAG AAC CAG CGC ATG CAC TCG GCC  315
 91  L   V   C   H   V   I   F   K   N   Q   R   M   H   S   A  105

316 ACC AGC CTC TTC ATT GTC AAC CTG GCA GTG GCG GAC ATC ATG ATC  360
106  T   S   L   F   I   V   N   L   A   V   A   D   I   M   I  120

361 ACA TTG CTC AAC ACG CCC TTC ACT TTG GTC CGC TTT GTG AAC AGC  405
121  T   L   L   N   T   P   F   T   L   V   R   F   V   N   S  135

406 ACA TGG GTG TTT GGG AAG GGC ATG TGT CAT GTC AGT CGC TTT GCT  450
136  T   W   V   F   G   K   G   M   C   H   V   S   R   F   A  150

451 CAG TAC TGT TCT CTA CAT GTC TCA GCA CTG ACT CTG ACA GCT ATC  495
151  Q   Y   C   S   L   H   V   S   A   L   T   L   T   A   I  165

496 GCA GTG GAC CGC CAC CAG GTC ATC ATG CAT CCA CTG AAG CCT CGG  540
166  A   V   D   R   H   Q   V   I   M   H   P   L   K   P   R  180

541 ATC TCC ATC ACC AAG GGT GTC ATA TAT ATT GCT GTC ATC TGG GTC  585
181  I   S   I   T   K   G   V   I   Y   I   A   V   I   W   V  195

586 ATG GCT ACC TTC TTC TCT CTG CCA CAT GCC ATC TGC CAG AAA CTG  630
196  M   A   T   F   F   S   L   P   H   A   I   C   Q   K   L  210

631 TTT ACC TTC AAG TAC AGT GAG GAC ATT GTG CGC TCC CTC TGC CTG  675
211  F   T   F   K   Y   S   E   D   I   V   R   S   L   C   L  225

676 CCG GAC TTC CCG GAG CCA GCT GAC CTC TTC TGG AAG TAT CTG GAC  720
226  P   D   F   P   E   P   A   D   L   F   W   K   Y   L   D  240

721 CTG GCC ACC TTC ATC CTG CTC TAC CTA CTT CCA CTC TTC ATT ATC  765
241  L   A   T   F   I   L   L   Y   L   L   P   L   F   I   I  255
```

Figure 2B

```
 766 TCA GTG GCC TAT GCT CGT GTG GCC AAG AAG CTG TGG CTC TGT AAC  810
 256  S   V   A   Y   A   R   V   A   K   K   L   W   L   C   N   270

811 ACC ATT GGC GAC GTG ACC ACA GAG CAG TAC CTC GCC CTG CGA CGC  855
 271  T   I   G   D   V   T   T   E   Q   Y   L   A   L   R   R   285

856 AAG AAG AAG ACC ACC GTG AAG ATG CTG GTG CTT GTG GTA GTC CTC  900
 286  K   K   K   T   T   V   K   M   L   V   L   V   V   V   L   300

901 TTT GCC CTC TGC TGG TTC CCT CTC AAC TGC TAT GTC CTC CTC TTG  945
 301  F   A   L   C   W   F   P   L   N   C   Y   V   L   L   L   315

946 TCC AGC AAG GCC ATC CAC ACC AAC AAT GCC CTC TAC TTT GCC TTC  990
 316  S   S   K   A   I   H   T   N   N   A   L   Y   F   A   F   330

991 CAC TGG TTT GCC ATG AGC AGT ACT TGT TAT AAC CCC TTC ATC TAC 1035
 331  H   W   F   A   M   S   S   T   C   Y   N   P   F   I   Y   345

1036 TGC TGG CTC AAT GAG AAC TTT AGG GTT GAG CTT AAG GCA TTG CTG 1080
 346  C   W   L   N   E   N   F   R   V   E   L   K   A   L   L   360

1081 AGC ATG TGC CAA AGG CCA CCC AAG CCG CAG GAA GAC AGG CTA CCC 1125
 361  S   M   C   Q   R   P   P   K   P   Q   E   D   R   L   P   375

1126 TCC CCA GTT CCT TCC TTC AGG GTG GCA TGG ACA GAG AAG AGC CAT 1170
 376  S   P   V   P   S   F   R   V   A   W   T   E   K   S   H   390

1171 GGT CGG AGG GCT CCA CTA CCT AAT CAC CAC TTG CCC TCT TCC CAG 1215
 391  G   R   R   A   P   L   P   N   H   H   L   P   S   S   Q   405

1216 ATC CAG TCT GGG AAG ACA GAT CTG TCA TCT GTG GAA CCC GTT GTG 1260
 406  I   Q   S   G   K   T   D   L   S   S   V   E   P   V   V   420

1261 GCC ATG AGT TAG                                              1272
 421  A   M   S   *                                               424
```

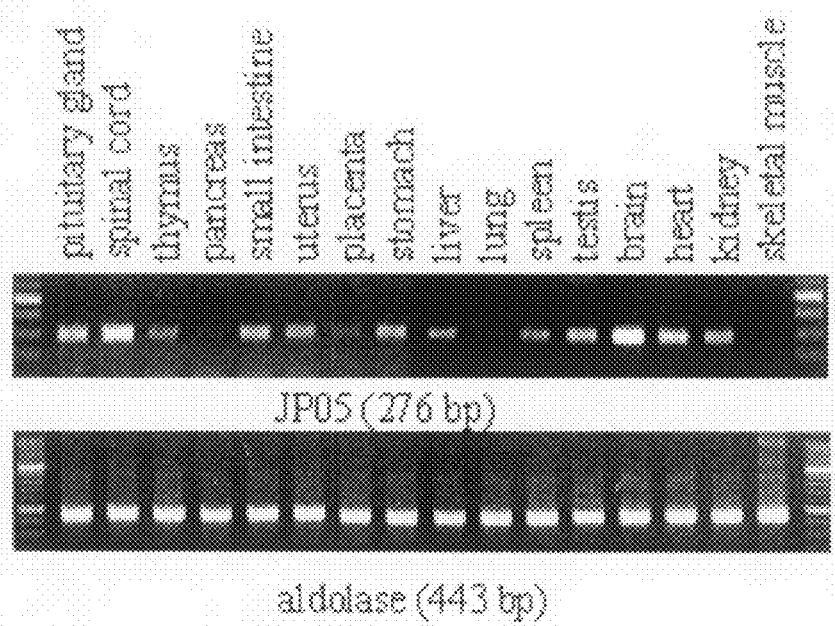
Figure 3 shows RT-PCR tissue distribution of the human GPR72 receptor

Figure 4 shows the mass spectrum obtained after electrospray-triple quadrupole mass spectrometry analysis of the purified active fraction.
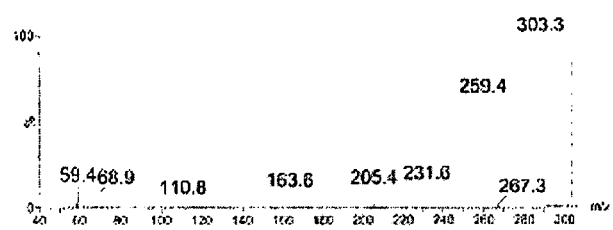
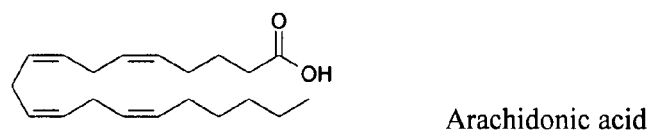
Arachidonic acid Figure 5 shows the aequorin calcium response of human GPR72 to arachidonic acid.
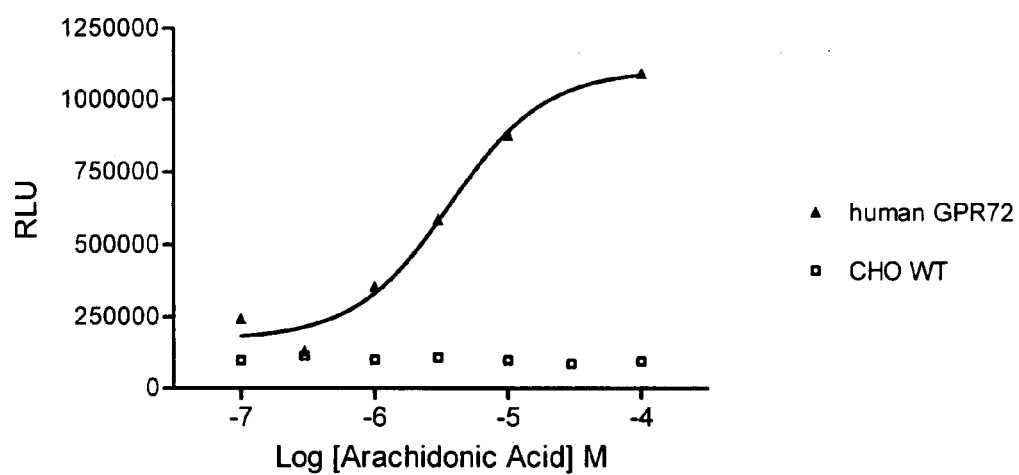

Figure 6 shows the aequorin calcium response of mouse GPR72 to arachidonic acid.
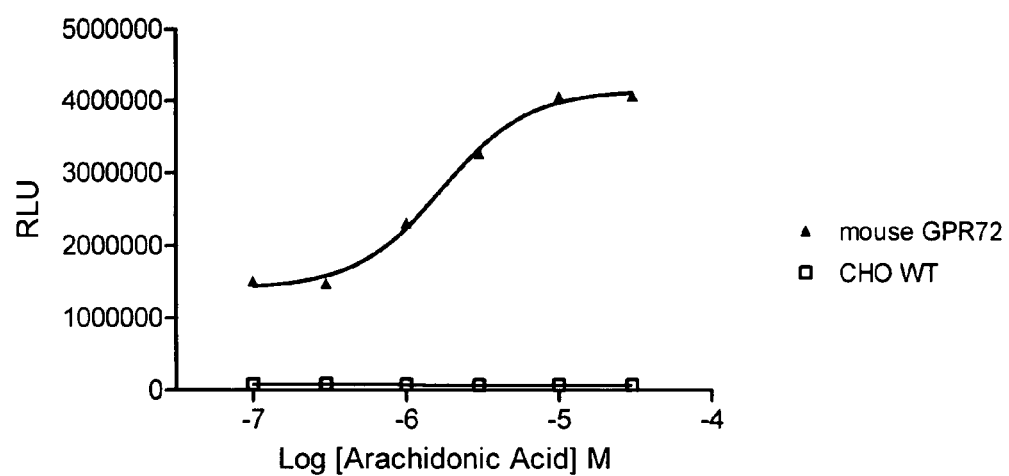

Figure 7 illustrates activation of human GPR72 receptor with several PUFAs and AA-PUFAs.
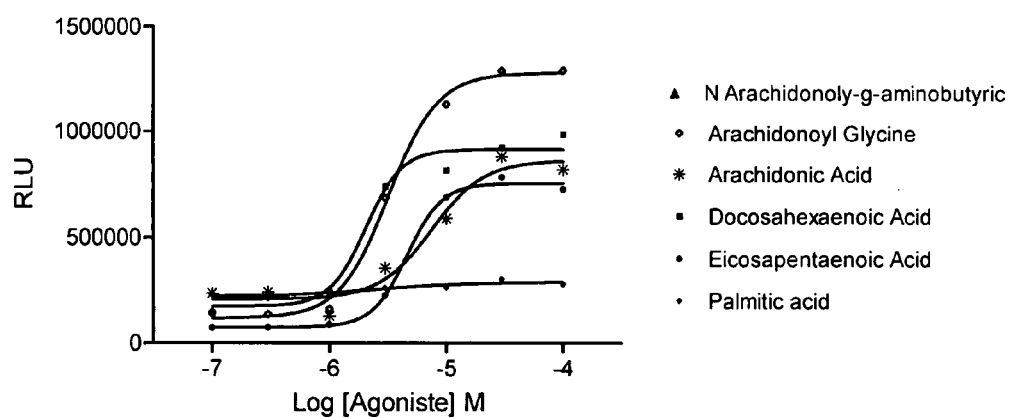

Figure 8 illustrates structure-activity relationship (SAR) of arachidonic acid on GPR72 activation

| | EC50 (µM) |
|---|---|
| Palmitic acid | inactive |
| 9Z-Palmitoleic acid | inactive |
| Stearic acid | inactive |
| 17-Octadecynoic acid | inactive |
| 6Z-Petroselinic acid | inactive |
| 9E-Elaidic acid | inactive |
| Octadeca-9Z,12Z,15Z-trienoic acid (α-Linolenic acid) | 4.7 |
| Octadeca-6Z,9Z,12Z-trienoic acid (γ-Linolenic acid) | 0.8 |
| Nonadecanoic acid | inactive |

Figure 8

| Compound | Activity |
|---|---|
| 9-cis-Retinoic acid | 0.4 |
| All-trans-retinal | inactive |
| All-trans-retinoic acid | 86 |
| Eicosanoic acid (Arachidic acid) | inactive |
| Eicosa-11Z,14Z-dienoic acid | 17.9 |
| Eicosa-8Z,11Z,14Z-trienoic acid (Dihomo-γ linolenic acid) | 44 |
| Eicosa-5Z,8Z,11Z-trienoic acid (Mead acid) | 6.3 |
| Eicosa-5Z,8Z,11Z,14Z-tetraenoic acid (Arachidonic acid) | 5 |
| Eicosa-8Z,11Z,14Z,17Z-tetraenoic acid | 6 |

Figure 8 (Continued)

| Compound | Activity |
|---|---|
| Arachidonic acid methyl ester | inactive |
| Eicosa-5Z,8Z,11Z,14Z,17Z-pentaenoic acid (EPA) | 3.3 |
| Heneicosanoic acid | inactive |
| Docosa-13Z-enoic acid | inactive |
| Docosa-13Z,16Z,19Z-trienoic acid | 25 |
| Docosa-7Z,10Z,13Z,16Z,19Z-pentaenoic acid | 9.3 |
| Docosa-4Z,7Z,10Z,13Z,16Z,19Z-hexaenoic acid (DHA) | 2 |
| N-arachidonoyl-L-taurine | 1.3 |
| N-arachidonoyl-L-serine | 3 |
| N-arachidonoyl-glycine | 3.5 |

Figure 8 (Continued)

| | |
|---|---|
| ![N-arachidonoyl-glycine structure] | |
| N-arachidonoyl-L-alanine ![structure] | 2.9 |
| N-arachidonoyl-3-hydroxy-γ-aminobutyric acid ![structure] | 0.7 |
| N-arachidonoyl-γ-aminobutyric acid ![structure] | 4.3 |

Figure 8 (Continued)

Figure 9 illustrates activation of human GPR72 receptor with additional PUFAs.
| | EC50 (μM) |
|---|---|
| Octadeca-6Z,9Z,12Z,15Z-tetraenoic acid (Stearidonic acid) 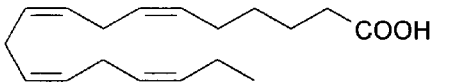 | 74 |
| Eicosa-11Z,14Z,17Z-trienoic acid 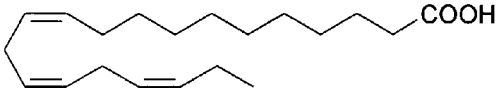 | 25 |
| Docosa-7Z,10Z,13Z,16Z-tetraenoic acid (Adrenic acid) 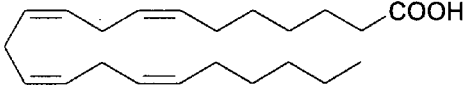 | 10 |
| Eicosa-5,8,11,14-tetraynoic acid 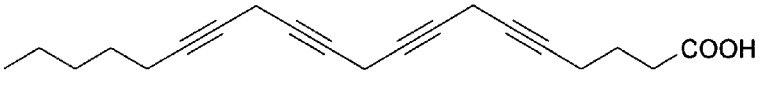 | 27 |
| Eicosa-5,8,11-triynoic acid 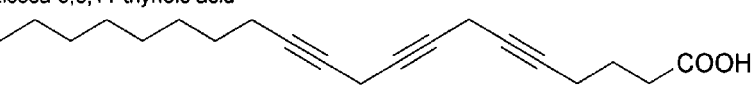 | 12 |
| 13-cis-Retinoic acid 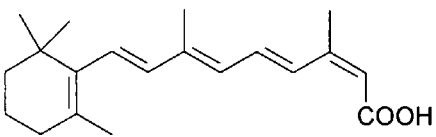 | 16 |

Figure 10 illustrates activation of human GPR72 receptor with three thiazolidinediones.
| | EC50 (µM) |
|---|---|
| Ciglitazone 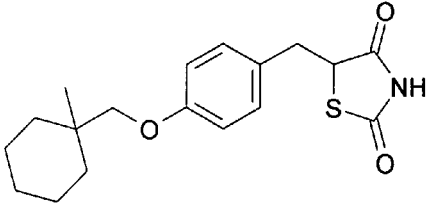 | 35 |
| MCC-555 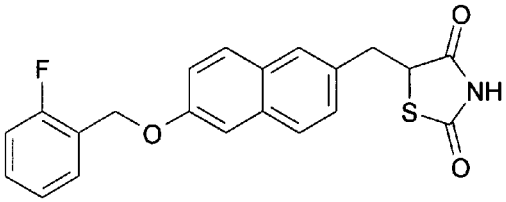 | 25 |
| Troglitazone 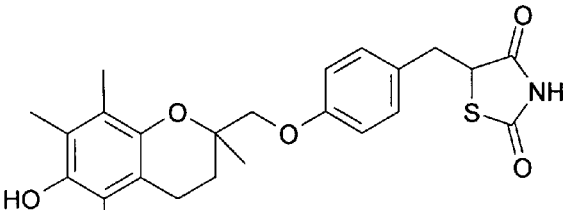 | 31 |

Figure 11 shows the aequorin calcium response of human GPR72 to two thiazolidinediones: Ciglitazone and MCC-555.
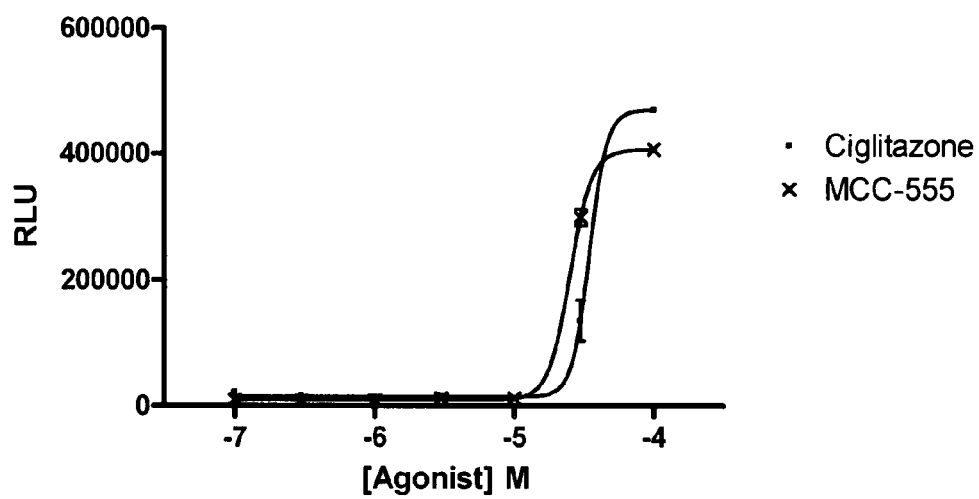

SEQUENCE LISTING

<160> NUMBER OF SEQ ID NOS: 16

<210> SEQ ID NO 1
<211> LENGTH: 1272
<212> TYPE: DNA
<213> ORGANISM: Homo sapiens

<400> SEQUENCE: 1

```
atggtccctc acctcttgct gctctgtctc ctcccttgg tgcgagccac cgagcccac      60 gagggccggg ccgacgagca gagcgcggag gcggccctgg ccgtgcccaa tgcctcgcac    120
ttcttctctt ggaacaacta caccttctcc gactggcaga actttgtggg caggaggcgc    180
```

```
tacggcgctg agtcccagaa ccccacggtg aaagccctgc tcattgtggc ttactccttc      240
atcattgtct tctcactctt tggcaacgtc ctggtctgtc atgtcatctt caagaaccag      300
cgaatgcact cggccaccag cctcttcatc gtcaacctgg cagttgccga cataatgatc      360
acgctgctca cacccccctt cactttggtt cgctttgtga acagcacatg gatatttggg      420
aagggcatgt gccatgtcag ccgctttgcc cagtactgct cactgcacgt ctcagcactg      480
acactgacag ccattgcggt ggatcgccac caggtcatca tgcaccccct gaaacccgg       540 atctcaatca caagggtgt catctacatc gctgtcatct ggaccatggc tacgttcttt       600
tcactcccac atgctatctg ccagaaatta tttaccttca atacagtga ggacattgtg       660 cgctccctct gcctgccaga cttccctgag ccagctgacc tcttctggaa gtacctggac      720
ttggccacct tcatcctgct ctacatcctg cccctcctca tcatctctgt ggcctacgct      780
cgtgtggcca agaaactgtg gctgtgtaat atgattggcg atgtgaccac agagcagtac      840
tttgccctgc ggcgcaaaaa gaagaagacc atcaagatgt tgatgctggt ggtagtcctc      900
tttgccctct gctggttccc cctcaactgc tacgtcctcc tcctgtccag caaggtcatc      960
cgcaccaaca atgccctcta ctttgccttc cactggtttg ccatgagcag cacctgctat     1020 aacccctca tatactgctg gctgaacgag aacttcagga ttgagctaaa ggcattactg      1080
agcatgtgtc aaagacctcc caagcctcag gaggacaggc caccctcccc agttccttcc     1140
ttcagggtgg cctggacaga gaagaatgat ggccagaggg ctccccttgc caataacctc     1200
ctgcccacct cccaactcca gtctgggaag acagacctgt catctgtgga acccattgtg     1260
acgatgagtt ag                                                         1272
```

<210> SEQ ID NO 2
<211> LENGTH: 423
<212> TYPE: PRT
<213> ORGANISM: Homo sapiens

<400> SEQUENCE: 2

```
Met Val Pro His Leu Leu Leu Cys Leu Leu Pro Leu Val Arg Ala
1               5                   10                  15

Thr Glu Pro His Glu Gly Arg Ala Asp Glu Gln Ser Ala Glu Ala Ala
            20                  25                  30

Leu Ala Val Pro Asn Ala Ser His Phe Phe Ser Trp Asn Asn Tyr Thr
        35                  40                  45

Phe Ser Asp Trp Gln Asn Phe Val Gly Arg Arg Tyr Gly Ala Glu
    50                  55                  60

Ser Gln Asn Pro Thr Val Lys Ala Leu Leu Ile Val Ala Tyr Ser Phe
65                  70                  75                  80

Ile Ile Val Phe Ser Leu Phe Gly Asn Val Leu Val Cys His Val Ile
                85                  90                  95

Phe Lys Asn Gln Arg Met His Ser Ala Thr Ser Leu Phe Ile Val Asn
            100                 105                 110

Leu Ala Val Ala Asp Ile Met Ile Thr Leu Leu Asn Thr Pro Phe Thr
        115                 120                 125

Leu Val Arg Phe Val Asn Ser Thr Trp Ile Phe Gly Lys Gly Met Cys
    130                 135                 140

His Val Ser Arg Phe Ala Gln Tyr Cys Ser Leu His Val Ser Ala Leu
145                 150                 155                 160

Thr Leu Thr Ala Ile Ala Val Asp Arg His Gln Val Ile Met His Pro
                165                 170                 175
```

-continued

| | | | | | | | | | | | |
|---|---|---|---|---|---|---|---|---|---|---|---|
|Leu|Lys|Pro|Arg|Ile|Ser|Ile|Thr|Lys|Gly|Val|Ile|Tyr|Ile|Ala|Val|
| | | |180| | | |185| | | |190| | | | |
|Ile|Trp|Thr|Met|Ala|Thr|Phe|Phe|Ser|Leu|Pro|His|Ala|Ile|Cys|Gln|
| | |195| | | | |200| | | | |205| | | |
|Lys|Leu|Phe|Thr|Phe|Lys|Tyr|Ser|Glu|Asp|Ile|Val|Arg|Ser|Leu|Cys|
| |210| | | | |215| | | | |220| | | | |
|Leu|Pro|Asp|Phe|Pro|Glu|Pro|Ala|Asp|Leu|Phe|Trp|Lys|Tyr|Leu|Asp|
|225| | | | |230| | | | |235| | | | |240|
|Leu|Ala|Thr|Phe|Ile|Leu|Leu|Tyr|Ile|Leu|Pro|Leu|Leu|Ile|Ile|Ser|
| | | | |245| | | | |250| | | | |255| |
|Val|Ala|Tyr|Ala|Arg|Val|Ala|Lys|Lys|Leu|Trp|Leu|Cys|Asn|Met|Ile|
| | | | |260| | | | |265| | | | |270| |
|Gly|Asp|Val|Thr|Thr|Glu|Gln|Tyr|Phe|Ala|Leu|Arg|Lys|Lys|Lys|
| | | | |275| | | | |280| | | | |285| |
|Lys|Thr|Ile|Lys|Met|Leu|Met|Leu|Val|Val|Leu|Phe|Ala|Leu|Cys|
| | |290| | | | |295| | | | |300| | | |
|Trp|Phe|Pro|Leu|Asn|Cys|Tyr|Val|Leu|Leu|Leu|Ser|Ser|Lys|Val|Ile|
|305| | | | |310| | | | |315| | | | |320|
|Arg|Thr|Asn|Asn|Ala|Leu|Tyr|Phe|Ala|Phe|His|Trp|Phe|Ala|Met|Ser|
| | | | |325| | | | |330| | | | |335| |
|Ser|Thr|Cys|Tyr|Asn|Pro|Phe|Ile|Tyr|Cys|Trp|Leu|Asn|Glu|Asn|Phe|
| | | |340| | | | |345| | | | |350| | |
|Arg|Ile|Glu|Leu|Lys|Ala|Leu|Leu|Ser|Met|Cys|Gln|Arg|Pro|Pro|Lys|
| | | |355| | | | |360| | | | |365| | |
|Pro|Gln|Glu|Asp|Arg|Pro|Pro|Ser|Pro|Val|Pro|Ser|Phe|Arg|Val|Ala|
| | |370| | | | |375| | | | |380| | | |
|Trp|Thr|Glu|Lys|Asn|Asp|Gly|Gln|Arg|Ala|Pro|Leu|Ala|Asn|Asn|Leu|
|385| | | | |390| | | | |395| | | | |400|
|Leu|Pro|Thr|Ser|Gln|Leu|Gln|Ser|Gly|Lys|Thr|Asp|Leu|Ser|Ser|Val|
| | | | |405| | | | |410| | | | |415| |
|Glu|Pro|Ile|Val|Thr|Met|Ser|
| | | |420| | | | | | | | | | | | |

<210> SEQ ID NO 3
<211> LENGTH: 1272
<212> TYPE: DNA
<213> ORGANISM: Mus musculus

<400> SEQUENCE: 3

| | | | | |
|---|---|---|---|---|
|atgaaggttc|ctcctgtcct|gcttctcttt|cttctgtcct|cagtgcgagc tactgagcaa|60|
|ccgcaggtcg|tcactgagca|tcccagcatg|gaggcagccc|tgaccgggcc caacgcctcc|120|
|tcgcacttct|gggccaacta|cactttctct|gactggcaga|acttcgtggg caggagacgt|180|
|tatggggccg|agtcccagaa|ccccacggtg|aaagcactgc|tcatcgtggc ctactcattc|240|
|accatcgtct|tctcgctctt|cggtaatgtc|ctggtctgtc|atgtcatctt caagaaccag|300|
|cgcatgcact|cggccaccag|cctcttcatt|gtcaacctgg|cagtggcgga catcatgatc|360|
|acattgctca|acacgccctt|cactttggtc|cgctttgtga|acagcacatg ggtgtttggg|420|
|aagggcatgt|gtcatgtcag|tcgctttgct|cagtactgtt|ctctacatgt ctcagcactg|480|
|actctgacag|ctatcgcagt|ggaccgccac|caggtcatca|tgcatccact gaagcctcgg|540|
|atctccatca|ccaagggtgt|catatatatt|gctgtcatct|gggtcatggc taccttcttc|600|
|tctctgccac|atgccatctg|ccagaaactg|tttaccttca|gtacagtga ggacattgtg|660|

```
cgctccctct gcctgccgga cttcccggag ccagctgacc tcttctggaa gtatctggac    720
ctggccacct tcatcctgct ctacctactt ccactcttca ttatctcagt ggcctatgct    780
cgtgtggcca agaagctgtg gctctgtaac accattggcg acgtgaccac agagcagtac    840
ctcgccctgc gacgcaagaa gaagaccacc gtgaagatgc tggtgcttgt ggtagtcctc    900
tttgccctct gctggttccc tctcaactgc tatgtcctcc tcttgtccag caaggccatc    960
cacaccaaca atgccctcta ctttgccttc cactggtttg ccatgagcag tacttgttat   1020
aaccccttca tctactgctg gctcaatgag aactttaggg ttgagcttaa ggcattgctg   1080
agcatgtgcc aaaggccacc caagccgcag gaagacaggc tacctccccc agttccttcc   1140
ttcagggtgg catggacaga gaagagccat ggtcggaggg ctccactacc taatcaccac   1200
ttgccctctt cccagatcca gtctgggaag acagatctgt catctgtgga acccgttgtg   1260
gccatgagtt ag                                                       1272

<210> SEQ ID NO 4
<211> LENGTH: 423
<212> TYPE: PRT
<213> ORGANISM: Mus musculus

<400> SEQUENCE: 4

Met Lys Val Pro Pro Val Leu Leu Phe Leu Leu Ser Ser Val Arg
1               5                   10                  15

Ala Thr Glu Gln Pro Gln Val Val Thr Glu His Pro Ser Met Glu Ala
            20                  25                  30

Ala Leu Thr Gly Pro Asn Ala Ser Ser His Phe Trp Ala Asn Tyr Thr
        35                  40                  45

Phe Ser Asp Trp Gln Asn Phe Val Gly Arg Arg Arg Tyr Gly Ala Glu
    50                  55                  60

Ser Gln Asn Pro Thr Val Lys Ala Leu Leu Ile Val Ala Tyr Ser Phe
65                  70                  75                  80

Thr Ile Val Phe Ser Leu Phe Gly Asn Val Leu Val Cys His Val Ile
                85                  90                  95

Phe Lys Asn Gln Arg Met His Ser Ala Thr Ser Leu Phe Ile Val Asn
            100                 105                 110

Leu Ala Val Ala Asp Ile Met Ile Thr Leu Leu Asn Thr Pro Phe Thr
        115                 120                 125

Leu Val Arg Phe Val Asn Ser Thr Trp Val Phe Gly Lys Gly Met Cys
    130                 135                 140

His Val Ser Arg Phe Ala Gln Tyr Cys Ser Leu His Val Ser Ala Leu
145                 150                 155                 160

Thr Leu Thr Ala Ile Ala Val Asp Arg His Gln Val Ile Met His Pro
                165                 170                 175

Leu Lys Pro Arg Ile Ser Ile Thr Lys Gly Val Ile Tyr Ile Ala Val
            180                 185                 190

Ile Trp Val Met Ala Thr Phe Phe Ser Leu Pro His Ala Ile Cys Gln
        195                 200                 205

Lys Leu Phe Thr Phe Lys Tyr Ser Glu Asp Ile Val Arg Ser Leu Cys
    210                 215                 220

Leu Pro Asp Phe Pro Glu Pro Ala Asp Leu Phe Trp Lys Tyr Leu Asp
225                 230                 235                 240

Leu Ala Thr Phe Ile Leu Leu Tyr Leu Leu Pro Leu Phe Ile Ile Ser
                245                 250                 255

Val Ala Tyr Ala Arg Val Ala Lys Lys Leu Trp Leu Cys Asn Thr Ile
```

-continued

```
                260                 265                 270
Gly Asp Val Thr Thr Glu Gln Tyr Leu Ala Leu Arg Arg Lys Lys Lys
            275                 280                 285

Thr Thr Val Lys Met Leu Val Leu Val Val Leu Phe Ala Leu Cys
290                 295                 300

Trp Phe Pro Leu Asn Cys Tyr Val Leu Leu Ser Ser Lys Ala Ile
305                 310                 315                 320

His Thr Asn Asn Ala Leu Tyr Phe Ala Phe His Trp Phe Ala Met Ser
                325                 330                 335

Ser Thr Cys Tyr Asn Pro Phe Ile Tyr Cys Trp Leu Asn Glu Asn Phe
            340                 345                 350

Arg Val Glu Leu Lys Ala Leu Leu Ser Met Cys Gln Arg Pro Pro Lys
                355                 360                 365

Pro Gln Glu Asp Arg Leu Pro Ser Pro Val Pro Ser Phe Arg Val Ala
            370                 375                 380

Trp Thr Glu Lys Ser His Gly Arg Arg Ala Pro Leu Pro Asn His His
385                 390                 395                 400

Leu Pro Ser Ser Gln Ile Gln Ser Gly Lys Thr Asp Leu Ser Ser Val
                405                 410                 415

Glu Pro Val Val Ala Met Ser
            420
```

<210> SEQ ID NO 5
<211> LENGTH: 7
<212> TYPE: PRT
<213> ORGANISM: Artificial Sequence
<220> FEATURE:
<223> OTHER INFORMATION: peptide derived from MARCKS

<400> SEQUENCE: 5

```
Phe Lys Lys Ser Phe Lys Leu
1               5
```

<210> SEQ ID NO 6
<211> LENGTH: 13
<212> TYPE: PRT
<213> ORGANISM: Artificial Sequence
<220> FEATURE:
<223> OTHER INFORMATION: kinase substrate Sigma A7433

<400> SEQUENCE: 6

```
Arg Arg Leu Ile Glu Asp Ala Glu Tyr Ala Ala Arg Gly
1               5                   10
```

<210> SEQ ID NO 7
<211> LENGTH: 8
<212> TYPE: DNA
<213> ORGANISM: Artificial Sequence
<220> FEATURE:
<223> OTHER INFORMATION: CRE DNA sequence

<400> SEQUENCE: 7 tgacgtca                                                           8

<210> SEQ ID NO 8
<211> LENGTH: 11
<212> TYPE: DNA
<213> ORGANISM: Artificial Sequence
<220> FEATURE:
<223> OTHER INFORMATION: NF-kB consensus sequence

<400> SEQUENCE: 8

-continued

```
gggggactttc c                                                              11

<210> SEQ ID NO 9
<211> LENGTH: 21
<212> TYPE: DNA
<213> ORGANISM: Homo sapiens

<400> SEQUENCE: 9
accatggtcc ctcacctctt g                                                    21

<210> SEQ ID NO 10
<211> LENGTH: 19
<212> TYPE: DNA
<213> ORGANISM: Homo sapiens

<400> SEQUENCE: 10
ctaactcatc gtcacaatg                                                       19

<210> SEQ ID NO 11
<211> LENGTH: 25
<212> TYPE: DNA
<213> ORGANISM: Mus musculus

<400> SEQUENCE: 11
cagtggctgg acatgaaggt tcctc                                                25

<210> SEQ ID NO 12
<211> LENGTH: 24
<212> TYPE: DNA
<213> ORGANISM: Mus musculus

<400> SEQUENCE: 12
cagctttccc taactcatgg ccac                                                 24

<210> SEQ ID NO 13
<211> LENGTH: 20
<212> TYPE: DNA
<213> ORGANISM: Artificial Sequence
<220> FEATURE:
<223> OTHER INFORMATION: Aldolase primer

<400> SEQUENCE: 13
ggcaagggca tcctggctgc                                                      20

<210> SEQ ID NO 14
<211> LENGTH: 20
<212> TYPE: DNA
<213> ORGANISM: Artificial Sequence
<220> FEATURE:
<223> OTHER INFORMATION: Aldolase primer

<400> SEQUENCE: 14
taacgggcca gaacattggc                                                      20

<210> SEQ ID NO 15
<211> LENGTH: 20
<212> TYPE: DNA
<213> ORGANISM: Artificial Sequence
<220> FEATURE:
<223> OTHER INFORMATION: GPR72 primer

<400> SEQUENCE: 15
cgcacttctt ctcttggaac                                                      20
```

```
<210> SEQ ID NO 16
<211> LENGTH: 20
<212> TYPE: DNA
<213> ORGANISM: Artificial Sequence
<220> FEATURE:
<223> OTHER INFORMATION: GPR72 primer

<400> SEQUENCE: 16
catgtgctgt tcacaaagcg                                              20
```

LIGAND FOR G-PROTEIN COUPLED RECEPTOR GPR72 AND USES THEREOF

PRIORITY INFORMATION

This application claims priority to European Application No. 06447078.4, filed on Jun. 13, 2006 the contents of which are incorporated herein in their entirety.

FIELD OF THE INVENTION

The present invention is related to natural ligands for an orphan G protein coupled receptor GPR72 and methods of use.

BACKGROUND OF THE INVENTION AND STATE OF THE ART

G-protein coupled receptors (GPCRs) are proteins responsible for transducing a signal within a cell. GPCRs have usually seven transmembrane domains. Upon binding of a ligand to an extra-cellular portion or fragment of a GPCR, a signal is transduced within the cell that results in a change in a biological or physiological property or behaviour of the cell. GPCRs, along with G-proteins and effectors (intracellular enzymes and channels modulated by G-proteins), are the components of a modular signalling system that connects the state of intra-cellular second messengers to extra-cellular inputs.

GPCR genes and gene products can modulate various physiological processes and are potential causative agents of disease. The GPCRs seem to be of critical importance to both the central nervous system and peripheral physiological processes.

The GPCR protein superfamily is represented by five families: Family I, receptors typified by rhodopsin and the beta2-adrenergic receptor and currently represented by over 200 unique members; Family II, the parathyroid hormone/calcitonin/secretin receptor family; Family III, the metabotropic glutamate receptor family, Family IV, the CAMP receptor family, important in the chemotaxis and development of *D. discoideum*; and Family V, the fungal mating pheromone receptor such as STE2.

G proteins represent a family of heterotrimeric proteins composed of α, β and γ subunits, that bind guanine nucleotides. These proteins are usually linked to cell surface receptors (receptors containing seven transmembrane domains) for signal transduction. Indeed, following ligand binding to the GPCR, a conformational change is transmitted to the G protein, which causes the α-subunit to exchange a bound GDP molecule for a GTP molecule and to dissociate from the βγ-subunits.

The GTP-bound form of the α, β and γ-subunits typically functions as an effector-modulating moiety, leading to the production of second messengers, such as cAMP (e.g. by activation of adenyl cyclase), diacylglycerol or inositol phosphates.

More than 20 different types of α-subunits are known in humans. These subunits associate with a small pool of β and γ subunits. Examples of mammalian G proteins include Gi, Go, Gq, Gs and Gt. G proteins are described extensively in Lodish et al., *Molecular Cell Biology* (Scientific American Books Inc., New York, N.Y., 1995; and also by Downes and Gautam, 1999, The G-Protein Subunit Gene Families. *Genomics* 62:544-552), the contents of both of which are incorporated herein by reference.

Known and uncharacterized GPCRs currently constitute major targets for drug action and development. There are ongoing efforts to identify new G protein coupled receptors which can be used to screen for new agonists and antagonists having potential prophylactic and therapeutic properties.

More than 300 GPCRs have been cloned to date, excluding the family of olfactory receptors. Mechanistically, approximately 50-60% of all clinically relevant drugs act by modulating the functions of various GPCRs (Cudermann et al., *J. Mol. Med.*, 73:51-63, 1995).

GPR72 initially referred to as GIR for glucocorticoid-induced receptor gene is also called JP05 or GPR83 (SEQ ID NO: 1, human polynucleotide sequence, SEQ ID NO: 2 human amino acid sequence). The predicted amino acid sequence was found to share significant similarity with the rhodopsin like G-protein coupled receptors family. The highest homology of GPR72 with known receptors is found with tachykinin receptors NK-1, NK-2, and NK-3 (32, 31 and 33%, respectively). The genomic organization of the mouse GPR72 gene has been determined and compared with the human gene [De Moerlooze et al., Cell Genet. 90 (2000) 146-150]. It is similar in both species, although differences leading to specific splicing variants in the mouse have been found. Comparative genetic mapping of the GPR72 gene showed that it maps to regions of conserved syngeny on mouse chromosome 9 (A2-3 region) and human chromosome 11 (q21 region) [Parker et al. Biochimica and Biophysica Acta, 1491 (2000) 369-375]. The human GPR72 polypeptide shares 89.5% identity with its mouse ortholog (SEQ ID NO:3, mouse polynucleotide sequence, SEQ ID NO:4 mouse amino acid sequence). GPR72 was originally identified as a stress-response element from murine thymoma WEHI-7TG cells after being treated with glucocorticoids and forskolin [Harrigan et al. Mol. Cell. Biol. 9 (1989) 3438-3446; Harrigan et al. Mol. Endocrinol. 5 (1991) 1331-1338]. CNS regulation of GPR72 mRNA following in vivo administration of dexamethasone suggests a potential role of this receptor in glucocorticoid-mediated effects such as, hypothalamic pituitary adrenal (HPA) function and stress regulation [Adams et al. Molecular Brain Research 117 (2003) 39-46]. In addition GPR72 transcript levels are increased significantly in rat prefrontal cortex for 7 days after discontinuation of chronic amphetamine exposure. The induction of GPR72 expression by amphetamine is associated with augmented behavioral activation suggesting that modulation of GPR72 expression may be involved in behavioral sensitization, and GPR72 may play a role at the interface between stress and neuroadaptation to psychostimulants [Wang et al. The journal of neuroscience 21 (2001) 9027-9035]. GPR72 mRNA were detected in high levels in human, rat and murine brain and spinal cord by Northern blot or RT-PCR analysis [Sah et al. Neuroscience 133 (2005) 281-292; Brezillon et al. Brain research 921 (2001) 21-30; Pesini et al. Molecular brain research 57 (1998) 281-300]. More specifically, distribution of GPR72 mRNA was examined in the human forebrain using in situ hybridization analysis. The results revealed a wide but discrete distribution of the transcript with strongly GPR72 mRNA expressing cells, presumably neurons, present in the cerebral cortex (layer II), hippocampus (pyramidal CA3 neurons and granule cells), amygdala (basal and periamygdaloid cortical nuclei), in the endopiriform nucleus, diagonal band of Broca, thalamus (nucleus reuniens, parafascicular nucleus) and hypothalamus (posterior, dorsal, and around the medial mammillary). Weaker signals were detected in the deeper cortical layers and throughout the striatum. A few positive cells were evident in the raphe but not in the substantia nigra or pontine nuclei [Brezillon et al. Brain research 921 (2001) 21-30]. The distribution patterns of GPR72 mRNA in the human brain suggest involvement in control of emotions and of neuroendocrine, cognitive and motor functions.

Polyunsaturated Fatty Acids (PUFAs) are fatty acids containing at least 16 carbons and two or more double bonds, optionally cyclic or branched, and optionally substituted with hydroxyl groups. Some examples are: linolenic acid (LA) (18:2n-6), alpha-linolenic acid (ALA) (18:3n-3), gamma-linolenic acid (GLA) (18:3n-6), arachidonic acid (AA) (20:4n-6), eicosapentaenoic acid (EPA) (20:5n-3), docosahexaenoic acid (DHA) (22:6n-3).

PUFAs occur throughout animal, plant, algae, fungi and bacteria. Found widely in many lipid compounds such as membranes, storage oils, glycolipids, phospholipids, sphingolipids and lipoproteins. Interest in PUFAs arises from their potential in therapeutic applications as well as in food and nutritional applications. They are produced commercially from selected seed plants, and some marine sources.

PUFAs provide structural and functional characteristics, and are involved in a wide range of biological components including membranes (in phospholipids). They are involved in regulating architecture, dynamics, phase transitions and permeability of membranes, and control of membrane-associated process. Also they are involved in regulating membrane-bound proteins such as ATPase, transport proteins and histocompatibility complexes. In addition, PUFAs regulate expression of some genes, including those coding for fatty-acid synthase, nitric-oxide synthase, sodium-channel proteins. Thus they have an impact on cellular biochemical activities, transport processes and cell-stimulus responses. They are involved in physiological processes including immune responses and cold adaptation, and implicated in pathological conditions such as cardiovascular disease.

Neurons contain a very high percentage of long-chain polyunsaturated fatty acids because they are used to construct complex structures such as the brain, which has very high rates of signal transfer and data processing. Excluding water, the mammalian brain is about 60 percent lipid (lipid is a general term for fatty biochemicals including phospholipids, triglycerides, ceramides and free fatty acids). However the central nervous system is unique compared to other tissues because it cannot directly use alpha-linolenic or linoleic acids, only their long chain PUFA derivates, which are mainly docosahexaenoic acid (DHA) and arachidonic acid (AA) [Broadhurst et al. Br J Nutr 79 (1998) 3-21].

Long chain PUFAs are the building material of the central nervous system and also are required for the normal behavior of cell signaling systems, which determine how neurons function [Clandinin Lipids; 34 (1999) 131-137].

In humans PUFA metabolism and eicosanoid function became important when it was discovered that arachidonate is the precursor for prostaglandins. Ecosanoids are a diverse group of hormones including prostaglandins, thromboxanes and leukotrienes. Research shows that eicosanoid hormones are fundamental to proper maintenance of homeostasis, and are linked to important physiological and pathophysiological conditions. The eicosanoid pathway in mammals begins with the phospholipase-mediated release of PUFAs from membrane phospholipids and is followed by cyclooxygenase-catalysed reactions that give rise to the major classes of metabolites, prostaglandins, thromboxanes, lipoxins and leukotrienes involved in the inflammatory response.

Lately, PUFA chemically related compounds where identified where the alpha amino group of an amino acid forms an amide bond with the carboxylic acid of arachidonic acid. These compounds generically named N-acyl-amino acids include but are not limited to N-arachidonoyl-glycine, N-arachidonoyl-L-serine, N-arachidonoyl-aminobutyric acid [Huang et al. J. B. C. 276 (2001) 42639-42644; Milman et al. PNAS 103 (2006) 2428-2433]. These PUFA derivatives are referred herein as AA-PUFAs for practical reason.

Antinociceptive actions have been described for N-arachidonoylglycine and N-arachidonoylg-aminobutyric and vasodilatory action was associated to N-arachidonoyl L-serine. These AA-PUFAs are also known for their inhibitory properties on fatty acid amide hydrolase. [Cascio et al. BBRC 314 (2004) 192-196; [Huang et al. J. B. C. 276 (2001) 42639-42644; Milman et al. PNAS 103 (2006) 2428-2433].

Interestingly, several arachidonic acid metabolites and other fatty acids have been shown to function as ligands for GPCRs, demonstrating that they can function as mediators, in vivo. Unesterified PUFAs are present in the plasma and in the brain. For example, arachidonic acid and DHA are present at 9 to 22 µM in the plasma and between 3 to 8 nmol/g fresh tissue in the brain, respectively [Kazushige et al. J. Neurochem 63 (1994) 727-736; Rosenberger et al. J. Neurochem 88 (2004) 1168-1178]. N-arachidonoyl-glycine was reported to be present in rat brain at concentration of 50 pmol/g dry tissue [Huang et al. JBC 276 (2001) 42639-42644].

Concentration of Arachidonic acid can be increased by 2 fold after LPS infusion in rat and by 20 fold following ischemia [Cao et al., Life Sciences 78 (2005) 74-81].

PUFAs in Human Nutrition and Disease

The importance of a balanced PUFAs intake has been recognized by health organizations throughout the world over the past decade. There is now some consensus that PUFAs should form a bare minimum 3%, and preferably 10-20%, of the total lipid intake, and that the 6- to 3-ratio should ideally be around 4 or 5:1. Although the biological effects of eicosanoids are undisputed, most diverse pharmacological effects have been proposed for PUFAs. An increase in PUFA consumption carries an elevated risk of exposure to toxic oxidation products, which are implicated in cancer, thrombotic and inflammatory diseases.

A substantial body of evidence links long chain PUFA deficiency to attention-deficit and/or hyperactivity disorders, dyslexia, senile dementia, clinical depression, bipolar disorder, schizophrenia, and other problems of a dual psychological and physiological nature [Peet et al., Marius Press (1999)].

A role of PUFAs was proposed in cocaine addiction [Buydens-Branchey et al., Psychiatry Res. 120 (2003) 29-35], and DHA was shown to ameliorate the impairment of spatial cognition learning ability in amyloid beta-infused rats [Hashimoto et al., J. Nutr. 135 (2005) 549-555]. Specific biological actions of arachidonic acid are described in animal models, such as decrease locomotive activity of mice [Laborit et al., Chem. Biol. Interact. 10 (1975) 309-312], moreover increased arachidonic acid concentration is found in the brain of Flinders Sensitive Line rats, an animal model of depression [Green et al., J. Lipid Res. 46 (2005) 1093-6].

The recognition of such long chain PUFA deficiencies has led many researchers to investigate its connection to numerous psychiatric disorders. So far the correlations have been remarkably positive.

Depression—In the past 100 years, the lifetime risk of developing major clinical depression has increased one hundredfold in North America. This increase coincides with the adoption of a diet based heavily on refined, processed agricultural commodities and a resultant dramatic reduction in n-3 PUFA consumption [Hibbeln & Salem Am. J. Clin. Nutr. 62 (1995) 1-9]. Studies have found that major depression is associated with low blood levels of DHA.

Hyperactivity Disorders and Dyslexia —PUFA deficiency also has been linked to attention deficit-hyperactivity disorder (ADHD) [Stevens et al., Am. J. Clin. Nutr. 62 (1995) 761-768]. Conversion of LA and ALA to long chain PUFA and/or PUFA metabolites in hyperactive children is probably not adequate to maintain normal brain function, or the inadequate conversion exacerbates a preexisting brain abnormality.

In several cases learning and health problems could be associated with low total PUFA levels, especially DHA [Stevens et al., Physiol. Behav. 59 (1996) 915-920].

Dyslexia is often characterized by a visual defect that decreases the eye's ability to adapt to the dark. In a 1995 controlled study conducted in Scotland, supplemental DHA at 480 mg per day for a month was shown to improve this problem in 10 dyslexics [Stordy Dyslexia Rev. 9 (1997) 1-3].

Senile dementia and Alzheimer's disease—Reduced levels of PUFAs have been observed in blood samples from Alzheimer's patients and those suffering from other forms of dementia. Higher levels of fish consumption were correlated to a lower incidence of dementia, including Alzheimer's dementia, in a study of 5,386 Dutch persons over age 55 [Kalmijn et al., Ann. Neurol. 42 (1997) 776-782]. Excessive oxidation of PUFAs in neuronal cell membranes may play a role in the development of Alzheimer's and related dementias.

Schizophrenia and bipolar disorder—Schizophrenia is the most extensively studied neurological disease in relation to lipid metabolism. Red blood cell fatty acids measured in schizophrenics from Ireland, England, Scotland, Japan and the United States have been shown to contain lower than normal levels of AA and DHA, and of PUFAs in general. Schizophrenia may manifest itself when at least two genetic abnormalities in fatty acid metabolism are simultaneously present: an increased rate of removal of PUFAs, especially AA and DHA from phospholipid cell membranes; and a reduced rate of incorporation of these same PUFAs in the cell membranes [Horrobin et al., Schizophr. Res. 30 (1998) 193-208].

Bipolar disorder, alcoholism and schizotypy (antisocial, "disconnected" personality disorder) are also more common in relatives of schizophrenics. Dyslexia and schizotypy arise when only the defect in PUFA incorporation is present [Christensen and Christensen Acta Psychiatr. Scand. 78 (1988) 586-591].

SUMMARY OF THE INVENTION

The present invention is based on the unusual and unexpected finding that the GPR72 receptor is specifically activated by polyunsaturated free fatty acids (PUFAs) and their salts, such as arachidonic acid, as well as the chemically related lipoamino acids (N-acyl-aminoacids) derived from PUFAs (AA-PUFAs) and their salts, such as N-arachidonoyl-glycine.

One embodiment of the present invention is a method for detecting GPR72 polypeptide activity in a sample comprising the steps of:

a) incubating a sample possibly comprising GPR72 polypeptide with PUFA under conditions which permit binding of GPR72 polypeptide and PUFA, b) detecting the second messenger level in said sample, c) incubating an identical or similar sample to the sample of step a) in the absence of PUFA under conditions which permit binding of GPR72 polypeptide and PUFA, d) detecting the reference level of second messenger produced in said sample, e) optionally, incubating a reference sample comprising GPR72 polypeptide with PUFA under conditions which permit binding of GPR72 polypeptide and PUFA, f) optionally, detecting an increase of second messenger in said reference sample, and g) comparing the second messenger level detected in step b) to the second messenger level detected in step d), and/or optionally to the second messenger level detected in step f), wherein GPR72 polypeptide activity is detected when the second messenger level detected in step b) is higher than the second messenger level detected in step d).

Another embodiment of the present invention is a method as described above wherein said sample comprises cells expressing GPR72 polypeptide.

Another embodiment of the present invention is a method as described above wherein said sample comprises cell membranes comprising GPR72 polypeptide.

Another embodiment of the present invention is a method as described above wherein said incubating is performed in or on virus-induced budding membranes comprising GPR72 polypeptide.

Another embodiment of the present invention is a method as described above, wherein step a) is performed in the presence of Gα16 polypeptide.

Another embodiment of the present invention is a method of identifying an agent that binds to GPR72 polypeptide, said method comprising:

(a) contacting a GPR72 polypeptide with PUFA in the presence or absence of a candidate binding agent under conditions permitting binding of said PUFA to said GPR72 polypeptide; and, (b) measuring binding of said GPR72 polypeptide to said PUFA, wherein a decrease in binding in the presence of said candidate binding agent, relative to binding in the absence of said candidate binding agent, identifies said candidate binding agent as an agent that binds to GPR72 polypeptide.

Another embodiment of the present invention is a method as described above, wherein said PUFA is detectably labeled.

Another embodiment of the present invention is a method as described above, wherein the label is chosen from the group consisting of a radioisotope, a fluorophore, a quencher of fluorescence, an enzyme, an affinity tag and epitope tag.

Another embodiment of the present invention is a method as described above, wherein said agent is present in a sample.

Another embodiment of the present invention is a method of identifying an agent that increases the signaling activity of GPR72 polypeptide, said method comprising:

(a) contacting a GPR72 polypeptide with an agent;

(b) measuring a signaling activity of said GPR72 polypeptide in the presence of said agent; and, (c) comparing said activity measured in the presence of said agent to the activity measured in a reaction in which said GPR72 polypeptide is contacted with PUFA, wherein said agent is identified as an agonist that increases the signaling of said GPR72 polypeptide when the amount of said activity measured in the presence of said agent is at least 10% of the amount induced by said PUFA.

Another embodiment of the present invention is a method as described above, wherein said agent is present in a sample.

Another embodiment of the present invention is a method of identifying an agent that decreases the signaling activity of GPR72 polypeptide, said method comprising:

(a) contacting a GPR72 polypeptide with PUFA in the presence or absence of said agent;

(b) measuring a signaling activity of said GPR72 polypeptide;

(c) comparing the amount of said activity measured in a reaction containing GPR72 polypeptide and said PUFA without said agent to the amount of said activity measured in a reaction containing said GPR72 polypeptide, said PUFA and said agent, wherein a decrease in said activity in the presence of said agent relative to the activity in the absence of said agent identifies said agent as an antagonist or inverse agonist for said GPR72 polypeptide.

Another embodiment of the present invention is a method as described above, wherein said agent is present in a sample.

Another embodiment of the present invention is a method as described above wherein said GPR72 polypeptide is expressed by cells on their surface.

Another embodiment of the present invention is a method as described above wherein said GPR72 polypeptide is comprised in cell membranes.

Another embodiment of the present invention is a method as described above, wherein said GPR72 polypeptide is present in or on virus-induced budding membranes.

Another embodiment of the present invention is a method as described above wherein said cells are selected from the group consisting of: COS7-cells, a CHO cell, a LM (TK-) cell, a NIH-3T3 cell, HEK-293 cell, K-562 cell and a 1321N1 astrocytoma cell and other cell lines, or wherein said cell membranes are derived from one of said cell lines.

Another embodiment of the present invention is a method as described above, further performed in the presence of Gα16 polypeptide.

Another embodiment of the present invention is a method as described above wherein said measuring or said detecting is performed using a method selected from label displacement, surface plasmon resonance, fluorescence resonance energy transfer, fluorescence quenching, and fluorescence polarization.

Another embodiment of the present invention is a method as described above wherein said agent is selected from the group consisting of a natural or synthetic peptide, a polypeptide, an antibody or antigen-binding fragment thereof, a lipid, a carbohydrate, a nucleic acid, and a small organic molecule.

Another embodiment of the present invention is a method as described above wherein said detecting or measuring a signalling activity or measuring the binding of said GPR72 polypeptide comprises detecting a change in the level of a second messenger.

Another embodiment of the present invention is a method as described above wherein the step of detecting or measuring a signalling activity or measuring the binding of said GPR72 polypeptide comprises measurement of guanine nucleotide binding or exchange, adenylate cyclase activity, cAMP, protein kinase C activity, phosphatidylinositol breakdown, diacylglycerol, inositol trisphosphate, intracellular calcium, arachinoid acid concentration, MAP kinase activity, tyrosine kinase activity, or, reporter gene expression.

Another embodiment of the present invention is a method as described above wherein said detecting or measuring a signalling activity comprises using an aequorin-based assay.

Another embodiment of the present invention is an agent obtained by a screening method disclosed herein.

Another embodiment of the present invention is an antibody which specifically binds to GPR72 polypeptide and which increases or decreases:
(a) the binding of PUFA to the GPR72 polypeptide, or
(b) the signalling activity of PUFA on the GPR72 polypeptide.

Another embodiment of the present invention is a method of in vitro diagnosing a disease or disorder characterized by dysregulation of GPR72 polypeptide binding, said method comprising:
a) contacting a tissue sample comprising a GPR72 polypeptide with PUFA;
b) detecting binding of said PUFA to said tissue sample; and,
c) comparing the binding detected in step (b) with a standard, wherein a difference in binding relative to said standard is diagnostic of a disease or disorder characterized by dysregulation of GPR72 polypeptide binding.

Another embodiment of the present invention is a method of in vitro diagnosing a disease or disorder characterized by dysregulation of GPR72 polypeptide signalling, said method comprising:
a) contacting a tissue sample comprising a GPR72 polypeptide with PUFA;
b) detecting a signalling activity of GPR72 polypeptide in said tissue sample; and,
c) comparing the signalling activity detected in step (b) with a standard, wherein a difference in signalling activity relative to said standard is diagnostic of a disease or disorder characterized by dysregulation of GPR72 polypeptide signalling.

Another embodiment of the present invention is a method as described above wherein said comparing is performed on a microarray.

Another embodiment of the present invention is a kit for detecting binding to GPR72 polypeptide, an agent binding to GPR72 polypeptide or an agent decreasing or increasing the signalling activity of GPR72 polypeptide, said kit comprising a GPR72 polypeptide and PUFA, and packaging materials therefore, wherein said GPR72 polypeptide and PUFA are packaged separately.

Another embodiment of the present invention is a kit as described above, wherein said GPR72 polypeptide is present in a cell expressing GPR72 polypeptide.

Another embodiment of the present invention is a kit as described above, wherein said GPR72 polypeptide is present in an isolated cell membrane comprising GPR72 polypeptide.

Another embodiment of the present invention is a kit as described above, wherein said GPR72 polypeptide is present in or on virus-induced budding membranes.

Another embodiment of the present invention is a kit as described above, wherein said cell is selected from the group consisting of: COS7-cells, a CHO cell, a LM (TK-) cell, a NIH-3T3 cell, HEK-293 cell, K-562 cell and a 1321N1 astrocytoma cell and other cell lines, or wherein said cell membranes are derived from one of said cell lines.

Another embodiment of the present invention is a kit as described above, wherein said kit further comprises an antibody specific for GPR72 polypeptide or a GPR72 polypeptide-specific nucleic probe packaged separately.

Another embodiment of the present invention is a kit as described above, said kit further comprising one or more components of a second messenger assay.

Another embodiment of the present invention is a kit as described above, said kit further comprising Gα16 polypeptide.

Another embodiment of the present invention is a kit for screening agents that increase or decrease the signalling activity of GPR72 polypeptide, said kit comprising
(a) an isolated polynucleotide encoding a GPR72 polypeptide, PUFA and means for detecting GPR72 polypeptide signalling, and packaging materials therefore, or (b) a cell transformed with a polynucleotide encoding a GPR72 polypeptide, PUFA and means for detecting GPR72 polypeptide signalling, and packaging materials therefore.

Another embodiment of the present invention is a kit for the diagnosis of a disease or a disorder characterized by dysregulation of GPR72 signalling, said kit comprising PUFA, and packaging materials therefore.

Another embodiment of the present invention is a kit for the diagnosis of a disease or disorder characterized by dysregulation of GPR72 signalling, said kit comprising an antibody specific for GPR72 polypeptide, an antibody as mentioned above, or a GPR72 polypeptide-specific nucleic acid probe.

Another embodiment of the present invention is a kit as described above further comprising a standard wherein said standard is chosen from the group consisting of: a cell line expressing GPR72 polypeptide, membranes comprising GPR72 polypeptide, virus-induced budding membranes comprising GPR72 polypeptide, and, a tissue sample comprising GPR72 polypeptide. According to the present invention, said tissue sample may be taken from a healthy patient or subject.

Another embodiment of the present invention is a use of PUFA, or an antibody as described above for the manufacture of a pharmaceutical composition for preventing, treating and/or alleviating a disease or disorder characterized by the dysregulation of GPR72 polypeptide signalling.

Another embodiment of the present invention is a use of PUFA or an antibody as mentioned above, for the diagnosis of a disease or disorder characterized by the dysregulation of GPR72 polypeptide signalling.

Another embodiment of the present invention is a use of PUFA or an antibody as mentioned above, for the preparation of a kit to detect or measure the binding or signalling of GPR72.

Another embodiment of the present invention is a use of PUFA or an antibody as mentioned above, for the validation of an assay comprising the use of a GPR72 non-human transgenic animal.

Another embodiment of the present invention is a method for the production of a pharmaceutical composition comprising the steps of admixing an antibody as described above, with a pharmaceutical carrier.

Another embodiment of the present invention is a pharmaceutical composition comprising an antibody as described above.

Another embodiment of the present invention is a composition comprising a PUFA and a GPR72 polypeptide.

Another embodiment of the present invention is a functional antibody or antigen-binding fragment thereof which specifically binds to GPR72 polypeptide and which increases or decreases the signalling activity of the GPR72 polypeptide.

Another embodiment of the present invention is an antibody which specifically binds to GPR72 polypeptide, and which increases or decreases the signalling activity of the GPR72 polypeptide.

Another embodiment of the present invention is an antibody which specifically binds to GPR72 polypeptide, and which increases the signalling activity of the GPR72 polypeptide, when the amount of said activity measured in the presence of the antibody is at least 10% of the amount induced by PUFAs. Another embodiment of the present invention is an antibody which specifically binds to GPR72 polypeptide, and which increases or decreases the signalling activity of the GPR72 polypeptide.

Another embodiment of the present invention is an antibody as described herein wherein said antibody is an agonist of GPR72 polypeptide.

Another embodiment of the present invention is an antibody as described herein wherein said antibody is an antagonist of GPR72 polypeptide.

Another embodiment of the present invention is an antibody as described herein wherein said antibody is monoclonal.

Another embodiment of the present invention is an antibody as described herein wherein said antibody is polyclonal.

Another embodiment of the present invention is an antibody as described herein wherein said antibody is humanized.

Another embodiment of the present invention is an antibody as described above wherein said antibody is chimeric.

Another embodiment of the present invention is an antibody as described above wherein said antibody is a single chain antibody.

Another embodiment of the present invention is a functional fragment of an antibody as described herein.

Another embodiment of the present invention is a functional fragment as described herein, which comprises the antigen binding fragment.

Another embodiment of the present invention is a homologous sequence of the amino acid sequence of an antibody or functional fragment as described above, or of a nucleotide sequence encoding said antibody or functional fragment.

Another embodiment of the present invention is an antibody, functional fragment or homologous sequence as described herein for preventing, treating and/or alleviating diseases or disorders characterized by dysregulation of formyl GPR72 polypeptide signalling.

It will be understood that in the above-mentioned embodiments the term PUFA can be replaced by AA-PUFA.

Another embodiment of the present invention is the antibody, functional fragment or homologous sequence as described above, the use as described above, the kit as described above or the method as described above, wherein said disease or disorder characterized by dysregulation of GPR72 polypeptide signalling is chosen from the group consisting of migraine, vomiting, psychotic and neurological disorders, including anxiety, schizophrenia, manic depression, depression, delirium, dementia and severe mental retardation, degenerative diseases, neurodegenerative diseases such as Alzheimer's disease or Parkinson's disease, Hyperactivity disorders like attention deficit-hyperactivity disorder (ADHA), dyslexia, depression, senile dementia, bipolar disorders like alcoholism and schizotypy and dyskinasias, such as Huntington's disease or Gilles de la Tourett's syndrome and other related diseases including thrombosis and other cardiovascular diseases, autoimmune and inflammatory diseases such as psoriasis, Eczeme, inflammatory and trophic diseases of skin, rheumatoid arthritis, scleroderma, lupus, polymyositis, dermatomysitis, Crohn's disease, inflammatory bowel disease (IBD), Irritable Bowel Syndrome, Ulcerative Colitis, Asthma, Chronic Obstructive Pulmonary Disease, Allergic Rhinitis, Fibromyalgia, Organ Transplant Rejection, Graft versus host disease, Multiple Sclerosis, Acute, Ischemic Stroke, Infectious diseases, Hepatitis A, Hepatitis B, Hepatitis C, Sepsis, Septic shock, Chronic bronchitis, infections such as bacterial, fungal, protozoan and viral infections, such as infections caused by HIV1 and HIV2, and pain, anorexia, bulimia, asthma, acute heart failure, hypertension, urinary retention, osteoporosis, angina pectoris, myocardial infarction, ulcers, allergies, benign prostatic hypertrophy, and Type 1 Diabetes, Type 2 Diabetes, Osteoarthritis, Diabetic Retinopathy, Diabetic Nephropathy and fertility dysfunctions, foetal developmental disorders, cell migration, cancer, development of tumours and tumour metastasis, inflammatory and neoplastic processes, wound and bone healing and dysfunction of regulatory growth functions, obesity, anorexia, bulimia, acute heart failure, hypotension, hypertension, urinary retention, osteoporosis, angina pectoris, restenosis, atherosclerosis, thrombosis and other cardiovascular diseases, autoimmune and, diseases characterized by excessive smooth muscle cell proliferation, aneurysms, diseases characterized by loss of smooth muscle cells or reduced smooth muscle cell proliferation, stroke, ischemia, ulcers, allergies and prostatic hypertrophy.

A further embodiment of the present invention is the method, kit, use, composition, fragment, sequence or antibody as described above wherein said GPR72 polypeptide corresponds to a sequence represented by SEQ ID NO: 2, a homologue thereof, or a fusion protein thereof.

A further embodiment of the present invention is the method, kit, use, composition, fragment, sequence or antibody as described above, wherein the fusion protein is made through the fusion of GPR72 and additional sequences which may be chosen from the group consisting of glutathione-S-transferase (GSP), maltose binding protein, alkaline phosphatase, thioredoxin, green fluorescent protein (GFP), histidine tags (e.g. 6× or greater His), and epitope tags (e.g. Myc tag, FLAF tag) sequences.

A further embodiment of the present invention is the method, kit, use, antibody and composition as described above wherein PUFA is replaced by AA-PUFA, or a combination thereof.

A further embodiment of the present invention is the method kit, use, antibody and composition as described above wherein PUFA or AA-PUFA is chosen from the group consisting of: Octadeca-9Z,12Z,15Z-trienoic acid (α-Linolenic acid), Octadeca-6Z,9Z,12Z-trienoic acid (γ-Linolenic acid), 9-cis-Retinoic acid, All-trans-retinoic acid, Eicosa-11Z,14Z-dienoic acid, Eicosa-8Z,11Z,14Z-trienoic acid (Dihomo-γ linolenic acid), Eicosa-5Z,8Z,11Z-trienoic acid (Mead acid), Eicosa-5Z,8Z,11Z,14Z-tetraenoic acid (Arachidonic acid), Eicosa-8Z,11Z,14Z,17Z-tetraenoic acid, Eicosa-5Z,8Z,11Z, 14Z,17Z-pentaenoic acid (EPA), Docosa-13Z,16Z,19Z-trienoic acid, Docosa-7Z,10Z,13Z,16Z,19Z-pentaenoic acid, Docosa-4Z,7Z,10Z,13Z,16Z,19Z-hexaenoic acid (DHA), N-arachidonoyl-L-taurine, N-arachidonoyl-L-serine, N-arachidonoyl-glycine, N-arachidonoyl-L-alanine, N-arachidonoyl-3-hydroxy-γ-aminobutyric acid, Octadeca-6Z,9Z,12Z,15Z-tetraenoic acid, Eicosa-11Z,14Z,17Z-trienoic acid, Docosa-7Z,10Z,13Z, 16Z-tetraenoic acid, Eicosa-5,8,11,14-tetraynoic acid, Eicosa-5,8,11-triynoic acid, 13-cis-Retinoic acid and N-arachidonoyl-γ-aminobutyric acid.

A further embodiment of the present invention is the method kit, use, antibody and composition as described above wherein PUFA is replaced by Ciglitazone, MCC-555, Troglitazone, or a combination thereof.

DESCRIPTION OF FIGURES

FIG. 1A and FIG. 1B represent nucleotide sequence (SEQ ID NO. 1) as cloned in pEFIN3 and deduced amino acid sequence (SEQ ID NO. 2) of the human GPR72 receptor. The starts and stops codons are indicated in bold.

FIG. 2A and FIG. 2B represent represents nucleotide sequence (SEQ ID NO. 3) as cloned in pEFIN3 and deduced amino acid sequence (SEQ ID NO. 4) of the mouse GPR72 receptor. The starts and stops codons are indicated in bold.

FIG. 3 shows RT-PCR tissue distribution of the human GPR72 receptor.

FIG. 4 shows the mass spectrum obtained after electrospray-triple quadrupole mass spectrometry analysis of the purified active fraction.

FIG. 5 shows the aequorin calcium response of human GPR72 to arachidonic acid.

FIG. 6 shows the aequorin calcium response of mouse GPR72 to arachidonic acid.

FIG. 7 illustrates activation of human GPR72 receptor with several PUFAs and AA-PUFAs.

FIG. 8 illustrates structure-activity relationship (SAR) of arachidonic acid on GPR72 activation.

FIG. 9 illustrates activation of human GPR72 receptor with additional PUFAs.

FIG. 10 illustrates activation of human GPR72 receptor with three thiazolidinediones.

FIG. 11 shows the aequorin calcium response of human GPR72 to two thiazolidinediones: Ciglitazone and MCC-555.

DETAILED DESCRIPTION OF THE INVENTION

The invention is based on the discovery that PUFAs and AA-PUFAs are natural ligands for the orphan G protein coupled receptor GPR72 polypeptide and on methods of using the binding of this ligand to the receptor in drug screening methods. The known ligand and its interaction with the receptor GPR72 polypeptide also provides for the diagnosis of conditions involving dysregulated receptor activity. The invention also relates to a kit comprising GPR72 polypeptide and homologous sequences, its corresponding polynucleotide and/or recombinant cells expressing the polynucleotide, to identify agonist, antagonist, inverse agonist and modulator compounds of the receptor polypeptide and/or its corresponding polynucleotide. Such kits are useful for the diagnosis, prevention and/or a treatment of diseases and disorders related to GPR72 polypeptide activity.

The invention also relates to novel agonist, antagonist, inverse agonist and modulator compounds of the receptor polypeptide and its corresponding polynucleotide, identified according to the method of the invention.

All references referred to below and above are incorporated herein by reference in their entirety.

The invention is based on the finding that PUFAs and AA-PUFAS, as defined herein, are natural ligands of the orphan receptor GPR72 (SEQ ID NO: 2). This invention thus relates to the PUFA and/or AA-PUFA ligand/receptor pair, and to functional homologs of the receptor which also bind PUFA and/or AA-PUFA and cells transformed by a vector comprising the nucleotide sequence encoding the receptor (SEQ ID NO: 1) in combination with the PUFA and/or AA-PUFA ligand. The invention also relates to a composition consisting essentially of an isolated GPR72 polypeptide and an isolated PUFA and/or AA-PUFA, as well as to methods of identifying agents that modulate the activities of GPR72 polypeptides. The methods are useful for the identification of agonist, inverse agonist or antagonist compounds useful for the development of new drugs. The interaction of GPR72 with PUFA and/or AA-PUFA is also useful for the development of diagnostics for diseases related to GPR72 activity.

For practical reason it will be understood that in the below-mentioned sections the term PUFA(s) can be replaced by AA-PUFA(s).

The invention encompasses a method of identifying an agent that modulates the function of GPR72 polypeptide, the method comprising: a) contacting a GPR72 polypeptide with a PUFA in the presence and absence of a candidate modulator under conditions permitting the binding of the PUFA to the GPR72 polypeptide; and b) measuring binding of the GPR72 polypeptide to the PUFA wherein a decrease in binding in the presence of the candidate modulator, relative to binding in the absence of the candidate modulator, identifies the candidate modulator as an agent that modulates the function of GPR72 polypeptide.

The invention further encompasses a method of detecting, in a sample, the presence of an agent that modulates the function of GPR72, the method comprising: a) contacting a GPR72 polypeptide with a PUFA in the presence and absence of the sample under conditions permitting the binding of the PUFA to the GPR72 polypeptide; and b) measuring binding of the GPR72 polypeptide to the PUFA wherein a decrease in binding in the presence of the sample, relative to binding in the absence of the sample, indicates the presence, in the sample of an agent that modulates the function of GPR72.

In one embodiment of either of the preceding methods, the measuring is performed using a method selected from label displacement, surface plasmon resonance, fluorescence resonance energy transfer, fluorescence quenching, and fluorescence polarization.

The invention further encompasses a method of identifying an agent that modulates the function of GPR72, the method comprising: a) contacting a GPR72 polypeptide with a PUFA in the presence and absence of a candidate modulator; and b) measuring a signalling activity of the GPR72 polypeptide, wherein a change in the activity in the presence of the candidate modulator relative to the activity in the absence of the candidate modulator identifies the candidate modulator as an agent that modulates the function of GPR72 polypeptide.

The invention further encompasses a method of identifying an agent that modulates the function of GPR72 polypeptide, the method comprising: a) contacting a GPR72 polypeptide with a candidate modulator; b) measuring a signalling activity of the GPR72 polypeptide in the presence of the candidate modulator; and c) comparing the activity measured in the presence of the candidate modulator to the activity measured in a sample or reaction in which the GPR72 polypeptide is contacted with a PUFA at its $EC_{50}$, wherein the candidate modulator is identified as an agent that modulates the function of GPR72 polypeptide when the amount of the activity measured in the presence of the candidate modulator is at least 10% of the amount induced by the PUFA present at its $EC_{50}$. The present application indicates that in certain methods of the present invention the PUFA may be present at its $EC_{50}$. However, this is only a preferred condition in said method and other PUFA concentrations may be used.

The invention further encompasses a method of detecting the presence, in a sample, of an agent that modulates the function of GPR72 polypeptide, the method comprising: a) contacting a GPR72 polypeptide with PUFA in the presence and absence of the sample; b) measuring a signalling activity of the GPR72 polypeptide; and c) comparing the amount of the activity measured in a reaction containing GPR72 polypeptide and PUFA without the sample to the amount of the activity measured in a reaction containing GPR72 polypeptide, PUFA and the sample, wherein a change in the activity in the presence of the sample relative to the activity in the absence of the sample indicates the presence, in the sample, of an agent that modulates the function of GPR72 polypeptide.

The invention further encompasses a method of detecting the presence, in a sample, of an agent that modulates the function of GPR72 polypeptide, the method comprising: a) contacting a GPR72 polypeptide with the sample; b) measuring a signalling activity of the GPR72 polypeptide in the presence of the sample; and c) comparing the activity measured in the presence of the sample to the activity measured in a reaction in which the GPR72 polypeptide is contacted with a PUFA present at its $EC_{50}$, wherein an agent that modulates the function of GPR72 polypeptide is detected if the amount of the activity measured in the presence of the sample is at least 10% of the amount induced by the PUFAs present at its $EC_{50}$.

In one embodiment of each of the preceding methods, the PUFA is detectably labeled. In a preferred embodiment, the PUFA is detectably labeled with a moiety selected from the group consisting of a radioisotope, a fluorophore, a quencher of fluorescence, an enzyme, and an affinity tag.

In an embodiment of each of the preceding methods, the contacting is performed in or on a cell expressing the GPR72 polypeptide.

In an embodiment of each of the preceding methods the contacting is performed in or on synthetic liposomes.

In an embodiment of each of the preceding methods the contacting is performed in or on virus-induced budding membranes containing a GPR72 polypeptide.

In an embodiment of each of the preceding methods the contacting is performed using a membrane fraction from cells expressing the GPR72 polypeptide.

In an embodiment of each of the preceding methods the measuring is performed using a method selected from the group consisting of label displacement, surface plasmon resonance, fluorescence resonance energy transfer, fluorescence quenching, and fluorescence polarization.

In an embodiment of each of the preceding methods the agent is selected from the group consisting of a natural or synthetic peptide or polypeptide, an antibody or antigen-binding fragment thereof, a lipid, a carbohydrate, a nucleic acid, an antisense nucleotide, and a small organic molecule.

In one embodiment of the methods wherein a signalling activity is measured, the step of measuring a signalling activity of the GPR72 polypeptide comprises detecting a change in the level of a second messenger.

In another embodiment of the methods wherein a signalling activity is measured, the step of measuring a signalling activity comprises measurement of guanine nucleotide binding or exchange, adenylate cyclase activity, cAMP, Protein Kinase C activity, phosphatidylinositol breakdown, diacylglycerol, inositol trisphosphate, intracellular calcium, arachinoid acid, MAP kinase activity, tyrosine kinase activity, or reporter gene expression.

In one embodiment, the step of measuring a signalling activity comprises using an aequorin-based assay.

The invention further comprises a method of modulating the activity of a GPR72 polypeptide in a cell, the method comprising the step of delivering to the cell an agent that modulates the activity of a GPR72 polypeptide, such that the activity of GPR72 polypeptide is modulated.

The invention further encompasses a method of diagnosing a disease or disorder characterized by dysregulation of GPR72 polypeptide signalling, the method comprising: a) contacting a tissue sample with an antibody specific for a GPR72 polypeptide; b) detecting binding of the antibody to the tissue sample; and c) comparing the binding detected in step (b) with a standard, wherein a difference in binding relative to the standard is diagnostic of a disease or disorder characterized by dysregulation of GPR72 polypeptide.

The invention further encompasses a method of diagnosing a disease or disorder characterized by dysregulation of GPR72 polypeptide signalling, the method comprising: a) isolating nucleic acid from a tissue sample; b) amplifying a GPR72 polynucleotide, using the nucleic acid as a template; and c) comparing the amount of amplified GPR72 polynucleotide produced in step (b) with a standard, wherein a difference in the amount of amplified GPR72 polynucleotide relative to the standard is diagnostic of a disease or disorder characterized by dysregulation of GPR72 polypeptide.

The invention further encompasses a method of diagnosing a disease or disorder characterized by dysregulation of GPR72 polypeptide signalling, the method comprising: a) isolating nucleic acid from a tissue sample; b) amplifying a GPR72 polynucleotide, using the nucleic acid as a template; and c) comparing the sequence of the amplified GPR72 polynucleotide produced in step (b) with a standard, wherein a difference in the sequence, relative to the standard is diagnostic of a disease or disorder characterized by dysregulation of GPR72 polypeptide. In one embodiment, the step of amplifying comprises RT/PCR. In another embodiment, the standard is SEQ ID NO: 1. In another embodiment, the step of comparing the sequence comprises minisequencing. In another embodiment, the step of comparing the amount is performed using a microarray.

The invention further encompasses a composition comprising or consisting essentially of an isolated GPR72 polypeptide and an isolated PUFA. An isolated GPR72 polypeptide and an isolated PUFA together can form a complex that is useful for the identification of agents that modulate their interaction, the identification of agents that modulate the activity of GPR72 polypeptides, and the identification of individuals suffering from a disease or disorder mediated by or involving GPR72 polypeptide. Complexed or uncomplexed (i.e., bound or unbound) isolated GPR72 polypeptide and isolated PUFA is thus the essential element or basis of the assays and methods of the invention. The composition "consisting essentially of" an isolated GPR72 polypeptide and an isolated PUFA can comprise additional components, however, such additional components are not essential to the novel interaction upon which the invention is based. The composition "consisting essentially of" an isolated GPR72 polypeptide and an isolated PUFA is distinct from and excludes naturally occurring complexes between GPR72 polypeptides and PUFA, present e.g., in cells, tissues or in cell or tissue extracts. The composition of the invention is also distinct from and excludes complexes between GPR72 polypeptides expressed from recombinant constructs and naturally-occurring PUFA.

Kits according to the invention are useful, for example, for screening for agents that modulate the activity of GPR72 polypeptide, identifying the presence of an agent that modulates GPR72 polypeptide in a sample, or for diagnosis of a disease or disorder characterized by dysregulation of GPR72 polypeptide. Kits according to the invention will additionally comprise packaging materials necessary for such kits. Kits according to the invention can additionally comprise a standard. In one embodiment, the standard is a sample from an individual not affected by a disease or disorder characterized by dysregulation of GPR72 polypeptide.

As used herein, the term "GPR72 polypeptide" refers to a polypeptide having at least 70% amino acid identity, preferably 71%, 72%, 73%, 74%, 75%, 76%, 77%, 78%, 79%, 80% amino acid identity, preferably 81%, 82%, 83%, 84%, 85%, 86%, 87%, 88%, 89%, 90%, 91%, 92%, 93%, 94%, 95%, 96%, 97%, 98%, 99%, up to and including 100% identity, with SEQ ID NO: 2, and which has GPR72 activity i.e., the GPR72 polypeptide binds a PUFAs. An GPR72 polypeptide may also be a functional fragment of SEQ ID NO: 2 i.e. a portion of SEQ ID NO:2 which is still capable of binding to a PUFAs. A functional fragment of SEQ ID NO: 2 may comprise at least 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 or 99% of the amino acids of the sequence represented by SEQ ID NO:2.

Optimally, a GPR72 polypeptide also has GPR72 signalling activity as defined herein.

As used herein, "GPR72 polypeptide activity" refers to specific binding to or signalling by a PUFA or AA-PUFA as defined herein.

A homologous sequence (which may exist in other mammal species or specific groups of human populations), where homology indicates sequence identity, means a sequence which presents a high sequence identity (more than 70, 71, 72, 73, 74, 75, 76, 77, 78, 79, 80, 81, 82, 83, 84, 85, 86, 87, 88, 89, 90, 91, 92, 93, 94, 95, 96, 97, 98 or 99% sequence identity) with the complete human nucleotide of SEQ ID NO: 1 or the complete human amino acid sequence of SEQ ID NO: 2. A functional homolog is characterized by the ability to bind a PUFA as defined herein or by the ability to initiate or propagate a signal in response to ligand binding, or both.

Homologous sequences of a sequence according to the invention may include an amino acid or nucleotide sequence encoding a similar receptor which exists in other animal species (rat, mouse, cat, dog, etc.) or in specific human population groups, but which are involved in the same biochemical pathway.

Such homologous sequences may comprise additions, deletions or substitutions of one or more amino acids or nucleotides, which do not substantially alter the functional characteristics of the receptor according to the invention. That is, homologs will have at least 90% of the activity of wild-type full length human GPR72 polypeptide and will bind PUFA specifically.

Such homologous sequences can also be nucleotide sequences of more than 50, 100, 200, 300, 400, 600, 800 or 1000 nucleotides which are able to hybridize to the complete human GPR72 sequence under stringent hybridisation conditions (such as the ones described by SAMBROOK et al., Molecular Cloning, Laboratory Manuel, Cold Spring, Harbor Laboratory press, New York). An example of "stringent hybridization conditions" is as follows: hybridize in 50% formamide, 5×SSC, 50 mM sodium phosphate (pH 6.8), 0.1% sodium pyrophosphate, 5×Denhardt's solution, 50 µg/ml sonicated salmon sperm DNA, 0.1% SDS and 10% dextran sulfate at 42° C.; and wash at 42° C. (or higher, e.g., up to two degrees C. below the $T_m$ of the perfect complement of the probe sequence) in 0.2×SSC and 0.1% SDS.

As used herein, the term "GPR72 signalling activity" refers to the initiation or propagation of signalling by a GPR72 polypeptide. GPR72 signalling activity is monitored by measuring a detectable step in a signalling cascade by assaying one or more of the following: stimulation of GDP for GTP exchange on a G protein; alteration of adenylate cyclase activity; protein kinase C modulation; phosphatidylinositol breakdown (generating second messengers diacylglycerol, and inositol trisphosphate); intracellular calcium flux; activation of MAP kinases; modulation of tyrosine kinases; or modulation of gene or reporter gene activity. A detectable step in a signalling cascade is considered initiated or mediated if the measurable activity is altered by 10% or more above or below a baseline established in the substantial absence of a PUFAs relative to any of the GPR72 polypeptide activity assays described herein below. The measurable activity can be measured directly, as in, for example, measurement of cAMP or diacylglycerol levels. Alternatively, the measurable activity can be measured indirectly, as in, for example, a reporter gene assay.

The term "PUFAs" or "PUFA" means Polyunsaturated Fatty Acid(s) which (is a) are fatty acid(s) containing at least 16 carbons and two or more double bonds, optionally cyclic or branched, and optionally substituted with hydroxyl groups. Some examples are: linolenic acid (LA) (18:2n-6), alpha-linolenic acid (ALA) (18:3n-3), gamma-linolenic acid (GLA) (18:3n-6), arachidonic acid (AA) (20:4n-6), eicosapentaenoic acid (EPA) (20:5n-3), docosahexaenoic acid (DHA) (22:6n-3).

The term "AA-PUFAs" or "AA-PUFA" means (an) amino acid(s) conjugated PUFA molecule(s) where the alpha amino group of an amino acid forms an amide bond with the carboxylic acid of a PUFA. AA-PUFAs include but are not limited to N-arachidonoyl-glycine, N-arachidonoyl-L-serine, N-arachidonoyl-taurine, N-arachidonoyl-aminobutyric acid [Huang et al. J. B. C. 276 (2001) 42639-42644; Milman et al. PNAS 103 (2006) 2428-2433].

The term amino acid means any molecule that contains both amino and carboxylic acid functional groups. In biochemistry, this shorter and more general term is frequently used to refer to alpha amino acids: those amino acids in which the amino and carboxylate functionalities are attached to the same carbon, the so-called α-carbon. Aside from the twenty standard amino acids, there are a vast number of nonstandard amino acids. Examples of nonstandard amino acids include the sulfur-containing taurine and the neurotransmitter GABA. Other examples are 1-amino isobutyric acid, dehydroalanine, dehydro-amino-butyric acid, carnitine, ornithine, citrulline, homocysteine, hydroxyproline, hydroxylysine and sarcosine.

The term "specifically binds" means that the PUFA has an $EC_{50}$, $IC_{50}$, or a $K_d$ of 100 µM or less.

As used herein, the term "detectable step" refers to a step that can be measured, either directly, e.g., by measurement of a second messenger or detection of a modified (e.g., phosphorylated) protein, or indirectly, e.g., by monitoring a downstream effect of that step. For example, adenylate cyclase activation results in the generation of cAMP. The activity of adenylate cyclase can be measured directly, e.g., by an assay that monitors the production of cAMP in the assay, or indirectly, by measurement of actual levels of cAMP.

Preferably, a recombinant cell according to the invention is a recombinant cell transformed by a plasmid, cosmid or viral vector, preferably a baculovirus, an adenovirus, or a semliki forest virus, and the cell is preferably selected from the group consisting of bacterial cells, yeast cells, insect cells or mammal cells.

According to a preferred embodiment of the present invention, the cell is selected from the group consisting of COS-7 cells, a CHO cell, a LM (TK-) cell, a NIH-3T3 cell, HEK-293 cell, K-562 cell or a 1321N1 astrocytoma cell. Other transfectable cell lines are also useful, however. Preferably, the vector comprises regulatory elements operatively linked to the polynucleotide sequence encoding the receptor according to the invention, so as to permit expression thereof.

Another aspect of the present invention is related to the use of a specific active portion of GPR72 polypeptide. As used herein, an "active portion" refers to a portion of a sequence that is of sufficient size to exhibit normal or near normal pharmacology (e.g., receptor activity (as defined herein), the response to an activator or inhibitor, or ligand binding are at least 90% of the level of activity, response, or binding exhibited by a wild type receptor). "A portion" as it refers to a sequence encoding a GPR72 polypeptide receptor, refers to less than 100% of the sequence (i.e., 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50% etc. . . . ). The active portion could be a GPR72 polypeptide receptor which comprises a partial deletion of the complete nucleotide or amino acid sequence and which still maintains the active site(s) and protein domain(s) necessary for the binding of and interaction with a specific ligand, preferably PUFA.

In another embodiment of any of the preceding methods, the contacting is performed in or on synthetic liposomes (Mirzabekov et al., 2000) or virus-induced budding membranes containing a GPR72 polypeptide. (see Patent application WO0102551, Virus-like particles, their Preparation and their Use preferably in Pharmaceutical Screening and Functional Genomics (2001) incorporated herein by reference).

As used herein, "ligand" refers to a moiety that is capable of associating or binding to a receptor. According to the method of the invention, a ligand and a receptor have a binding constant that is sufficiently strong to allow detection of binding by an assay method that is appropriate for detection of a ligand binding to a receptor (e.g. a second messenger assay to detect an increase or decrease in the production of a second messenger in response to ligand binding to the receptor, a binding assay to measure protein-ligand binding or an immunoassay to measure antibody-antigen interactions). A ligand according to the invention includes the actual molecule that binds a receptor or a ligand may be any nucleotide, antibody, antigen, enzyme, small organic molecule, peptide, polypeptide or nucleic acid capable of binding to the receptor. A ligand is preferably PUFA, a peptide or a small molecule. According to the method of the invention, a ligand and receptor specifically bind to each other (e.g. via covalent or hydrogen bonding or via an interaction between, for example, a protein and a ligand, an antibody and an antigen or protein subunits).

Another aspect of the present invention is related to a method for the screening, detection and recovery of candidate modulators of a receptor of the invention comprising the steps of: contacting a cell expressing GPR72 polypeptide with PUFA under conditions which permit binding of PUFA to GPR72 polypeptide, in the presence of the candidate modulator, performing a second messenger assay, and comparing the results of the second messenger assay obtained in the presence or absence of the candidate modulator.

Another aspect of the present invention is related to a method for the screening, detection and possible recovery of candidate modulators of a receptor of the invention comprising the steps of: contacting a cell membrane expressing GPR72 polypeptide with PUFA under conditions which permit binding of PUFA to GPR72 polypeptide, performing a second messenger assay, and comparing the results of the second messenger assay obtained in the presence or absence of the candidate modulator.

In another embodiment, the step of measuring a signalling activity of the GPR72 polypeptide comprises detecting a change in the level of a second messenger.

A further aspect of the present invention is related to the unknown agonist and/or antagonist compounds identified and/or recovered by the method of the invention, as well as to a diagnostic kit comprising the (unknown) compounds or a pharmaceutical composition (including a vaccine) comprising an adequate pharmaceutical carrier and a sufficient amount of the (unknown) compound.

An antagonist compound according to the invention means a molecule or a group of molecules able to bind to the receptor according to the invention and block the binding of natural compounds (PUFAs).

The invention further encompasses a method of diagnosing a disease or disorder characterized by dysregulation of GPR72 polypeptide signalling, the method comprising: a) contacting a tissue sample with an antibody specific for a GPR72 polypeptide and an antibody specific for a GPR72 ligand; b) detecting binding of the antibodies to the tissue sample; and c) comparing the binding detected in step (b) with a standard, wherein a difference in binding of either antibody or both, relative to the standard, is diagnostic of a disease or disorder characterized by dysregulation of GPR72 polypeptide.

The invention further encompasses a method of diagnosing a disease or disorder characterized by dysregulation of GPR72 polypeptide signalling, the method comprising: a) isolating a tissue sample; b) measuring the concentration of PUFA; and c) comparing the amount of PUFA measured in step (b) with a standard, wherein a difference in the amount of PUFA relative to the standard is diagnostic of a disease or disorder characterized by dysregulation of GPR72 polypeptide.

A further aspect of the present invention is related to a non-human mammal comprising a homozygous null mutation (homozygous "knock-out") of the polynucleotide sequence encoding the GPR72 polypeptide receptor according to the invention, or a transgenic non-human mammal that over expresses a GPR72 polypeptide above the natural level of expression. As used herein. "above the natural level of expression" refers to a level that is at least 2-fold, preferably 5-fold, more preferably 10-fold and most preferably 100-fold or more (i.e., 150-fold, 200-fold, 250-fold, 500-fold, 1000-fold, 10,000-fold etc.) as compared to the level of expression of the endogenous receptor in its normal native context. A transgenic non-human mammal according to the invention will express the transgene in at least one tissue or cell type but can express the GPR72 polypeptide transgene in all tissues and cells. A transgenic non-human mammal can be obtained by a method well known by a person skilled in the art, for instance, as described in document WO 98/20112 using the classical technique based upon the transfection of embryonic stem cells, preferably according to the method described by Carmeliet et al. (Nature, Vol. 380, p. 435-439, 1996).

"Gene targeting" is a type of homologous recombination that occurs when a fragment of genomic DNA is introduced into a mammalian cell and that fragment locates and recombines with endogenous homologous sequences as exemplified in U.S. Pat. Nos. 5,464,764, and 5,777,195, the contents of which are hereby incorporated by reference herein in their entireties. As used herein the term "transgenic animal" refers to a non-human animal in which one or more, and preferably essentially all, of the cells of the animal contain a transgene introduced by way of human intervention, such as by transgenic techniques known in the art. The transgene can be introduced into the cell, directly or indirectly by introduction into a precursor of the cell, by way of deliberate genetic manipulation, such as by microinjection or by infection with a recombinant virus.

Preferably, the transgenic non-human mammal overexpressing the polynucleotide encoding the GPR72 polypeptide receptor according to the invention comprises the polynucleotide incorporated in a DNA construct with an inducible promoter allowing the overexpression of the receptor and possibly also tissue and cell-specific regulatory elements.

In one embodiment, the kits according to the invention comprise reagents for measuring the binding of a PUFA to a GPR72 polypeptide. In another embodiment, the kit comprises reagents for measuring a signalling activity of a GPR72 polypeptide.

In one embodiment, a screening or diagnostic kit according to the invention includes a GPR72 receptor polypeptide or a cellular membrane preparation comprising a GPR72 polypeptide and one or more PUFAs in separate containers. Such kits can additionally comprise all the necessary means and media for performing a detection of specific binding (for example of PUFAs) to the GPR72 polypeptide receptor according to the invention. Binding or signalling activity can be correlated with a method of monitoring one or more of the symptoms of the diseases described hereafter.

The diagnostic kits can thus further comprise elements necessary for a specific diagnostic measurement, or, for example, the measurements of bound compounds using high throughput screening techniques known to the person skilled in the art, e.g., the techniques described in WO 00/02045. Such kits can be used, e.g. to monitor dosage and effectiveness of GPR72 polypeptide modulating agents used for treatment. The high throughput screening diagnostic dosage and monitoring can be performed by using various solid supports, such as microtiter plates or biochips selected by the person skilled in the art.

In a pharmaceutical composition according to the invention, the adequate pharmaceutical carrier is a carrier of solid, liquid or gaseous form, which can be selected by the person skilled in the art according to the type of administration and the possible side effects of the compound administered to modulate GPR72 polypeptide activity. The pharmaceutical carrier useful according to the invention does not include tissue culture medium or other media comprising serum. The ratio between the pharmaceutical carrier and the specific compound can be selected by the person skilled in the art according to the patient treated, the administration and the possible side effects of the compound, as well as the type of disease of disorder treated or sought to be prevented.

The pharmaceutical composition finds advantageous applications in the field of treatment and/or prevention of various diseases or disorders, preferably selected from the group consisting of migraine, vomiting, psychotic and neurological disorders, including anxiety, schizophrenia, manic depression, depression, delirium, dementia and severe mental retardation, degenerative diseases, neurodegenerative diseases such as Alzheimer's disease or Parkinson's disease, Hyperactivity disorders like attention deficit-hyperactivity disorder (ADHA), dyslexia, depression, senile dementia, bipolar disorders like alcoholism and schizotypy and dyskinasias, such as Huntington's disease or Gilles de la Tourett's syndrome and other related diseases including thrombosis and other cardiovascular diseases, autoimmune and inflammatory diseases such as psoriasis, Eczeme, inflammatory and trophic diseases of skin, rheumatoid arthritis, scleroderma, lupus, polymyositis, dermatomysitis, Crohn's disease, inflammatory bowel disease (IBD), Irritable Bowel Syndrome, Ulcerative Colitis, Asthma, Chronic Obstructive Pulmonary Disease, Allergic Rhinitis, Fibromyalgia, Organ Transplant Rejection, Graft versus host disease, Multiple Sclerosis, Acute, Ischemic Stroke, Infectious diseases, Hepatitis A, Hepatitis B, Hepatitis C, Sepsis, Septic shock, Chronic bronchitis, infections such as bacterial, fungal, protozoan and viral infections, such as infections caused by HIV1 and HIV2, and pain, anorexia, bulimia, asthma, acute heart failure, hypertension, urinary retention, osteoporosis, angina pectoris, myocardial infarction, ulcers, allergies, benign prostatic hypertrophy, and Type 1 Diabetes, Type 2 Diabetes, Osteoarthritis, Diabetic Retinopathy, Diabetic Nephropathy and fertility dysfunctions, foetal developmental disorders, cell migration, cancer, development of tumours and tumour metastasis, inflammatory and neoplastic processes, wound and bone healing and dysfunction of regulatory growth functions, obesity, anorexia, bulimia, acute heart failure, hypotension, hypertension, urinary retention, osteoporosis, angina pectoris, restenosis, atherosclerosis, thrombosis and other cardiovascular diseases, autoimmune and, diseases characterized by excessive smooth muscle cell proliferation, aneurysms, diseases characterized by loss of smooth muscle cells or reduced smooth muscle cell proliferation, stroke, ischemia, ulcers, allergies and prostatic hypertrophy.

Among the mentioned diseases the preferred applications are related to therapeutic agents targeting 7™ receptors that can play a function in preventing, improving or correcting dysfunctions or diseases, including, but not limited to migraine, vomiting, psychotic and neurological disorders, including anxiety, schizophrenia, manic depression, depression, delirium, dementia and severe mental retardation, degenerative diseases, neurodegenerative diseases such as Alzheimer's disease or Parkinson's disease, Hyperactivity disorders like attention deficit-hyperactivity disorder (ADHA), dyslexia, depression, senile dementia, bipolar disorders like alcoholism and schizotypy and dyskinasias, such as Huntington's disease or Gilles de la Tourett's syndrome and other related diseases including thrombosis and other cardiovascular diseases, autoimmune and inflammatory diseases such as psoriasis, Eczeme, inflammatory and trophic diseases of skin, rheumatoid arthritis, scleroderma, lupus, polymyositis, dermatomyositis, Crohn's disease, inflammatory bowel disease (IBD), Irritable Bowel Syndrome, Ulcerative Colitis, Asthma, Chronic Obstructive Pulmonary Disease, Allergic Rhinitis, Fibromyalgia, Organ Transplant Rejection, Graft versus host disease, Multiple Sclerosis, Acute, Ischemic Stroke, Infectious diseases, Hepatitis A, Hepatitis B, Hepatitis C, Sepsis, Septic shock, Chronic bronchitis, infections such as bacterial, fungal, protozoan and viral infections, such as infections caused by HIV1 and HIV2, and pain, anorexia, bulimia, asthma, acute heart failure, hypertension, urinary retention, osteoporosis, angina pectoris, myocardial infarction, ulcers, allergies, benign prostatic hypertrophy, and Type 1 Diabetes, Type 2 Diabetes, Osteoarthritis, Diabetic Retinopathy, Diabetic Nephropathy and fertility dysfunctions, foetal developmental disorders, cell migration, cancer, development of tumours and tumour metastasis, inflammatory and neoplastic processes, wound and bone healing and dysfunction of regulatory growth functions, obesity, anorexia, bulimia, acute heart failure, hypotension, hypertension, urinary retention, osteoporosis, angina pectoris, restenosis, atherosclerosis, thrombosis and other cardiovascular diseases, autoimmune and, diseases characterized by excessive smooth muscle cell proliferation, aneurysms, diseases characterized by loss of smooth muscle cells or reduced smooth muscle cell proliferation, stroke, ischemia, ulcers, allergies and prostatic hypertrophy.

The invention further encompasses an agent which modulates GPR72 polypeptide activity identified by the method or detected in a sample as mentioned above.

The invention further encompasses the use of said agent for the modulation of GPR72 polypeptide activity.

The invention further encompasses the use of said agent for the manufacture of a medicament for the treatment of GPR72 polypeptide-related diseases or for the manufacture of a kit for the modulation of GPR72 polypeptide activity.

The invention further encompasses a pharmaceutical composition comprising an adequate pharmaceutical carrier or diluent and a sufficient amount of said agent.

The invention further encompasses a pharmaceutical composition according to according to the above-mentioned, further comprising a vesicle or an adjuvant able to modulate the immune response of a patient to which it is administered.

The invention further encompasses the use of the above-mentioned pharmaceutical composition for the manufacture of a medicament for the treatment of GPR72 polypeptide-related diseases or for the manufacture of a kit for the modulation of GPR72 polypeptide.

The invention also relates to the use of a PUFA for the modulation of GPR72 polypeptide activity in vivo and/or in vitro.

The invention also relates to the use of a PUFA in the validation of an assay comprising a non-human mammal comprising a partial or total deletion of the polynucleotide encoding GPR72 polypeptide.

The invention also relates to the use of a PUFA in the validation of an assay comprising a non-human mammal overexpressing the polynucleotide encoding GPR72 polypeptide.

As used herein, an "antagonist" is a ligand which competitively binds to a receptor at the same site as an agonist, but does not activate an intracellular response initiated by an active form of the receptor. An antagonist thereby inhibits the intracellular response induced by an agonist, for example PUFA, by at least 10%, preferably 15-25%, more preferably 25-50% and most preferably, 50-100%, as compared to the intracellular response in the presence of an agonist and in the absence of an antagonist.

As used herein, an "agonist" refers to a ligand that activates an intracellular response when it binds to a receptor at concentrations equal to or lower than PUFA concentrations which induce an intracellular response. An agonist according to the invention can increase the intracellular response mediated by a receptor by at least 2-fold, preferably 5-fold, more preferably 10-fold and most preferably 100-fold or more (i.e., 150-fold, 200-fold, 250-fold, 500-fold, 1000-fold, 10,000-fold etc. . . . ), as compared to the intracellular response in the absence of agonist. An agonist according to the invention may promotes internalization of a cell surface receptor such that the cell surface expression of a receptor is decreased by at least 2-fold, preferably 5-fold, more preferably 10-fold and most preferably, 100-fold or more (i.e., 150-fold, 200-fold, 250-fold, 500-fold, 1000-fold, 10,000-fold etc. . . . ), as compared to the number of cell surface receptors present on the surface of a cell in the absence of an agonist.

As used herein, an "inverse agonist" refers to a ligand which decreases a constitutive activity of a cell surface receptor when it binds to a receptor. An inverse agonist according to the invention can decrease the constitutive intracellular response mediated by a receptor by at least 2-fold, preferably 5-fold, more preferably 10-fold and most preferably 100-fold or more (i.e., 150-fold, 200-fold, 250-fold, 500-fold, 1000-fold, 10,000-fold etc. . . . ), as compared to the intracellular response in the absence of inverse agonist.

An "inhibitor" compound according to the invention is a molecule directed against the receptor or against the natural ligand for the receptor that decreases the binding of the ligand to the receptor by at least 10%, preferably 15-25%, more preferably 25-50% and most preferably, 50-100%, in the presence of PUFA, as compared to the binding in the presence of PUFA and in the absence of inhibitor. An "inhibitor" compound of the invention can decrease the intracellular response induced by an agonist, for example PUFA, by at least 10%, preferably 15-25%, more preferably 25-50% and most preferably, 50-100%. An "inhibitor" also refers to a nucleotide sequence encoding an inhibitor compound of the invention. An inhibitor, useful according to the present invention, includes, but is not limited to an antibody which specifically binds to at least a portion of GPR72 polypeptide which is required for signal transduction through GPR72 polypeptide (such as the ligand binding site), or chemical compounds which are capable of blocking or reducing (e.g., by at least 10%) the signal transduction pathway which is coupled to the GPR72 polypeptide receptor. Such inhibitors include, but are not limited to sub-lethal doses of pertussis toxin, N-ethylmaleimide (NEM; Sigma), dibutyryl cAMP (Boehringer Mannheim, Corp.), and H-89 (N-[2-((p-bromocinnamyl)amino) ethyl]-5-isoquinolinesulfonamide-HCL; Calbiochem).

As used herein, "natural ligand" refers to a naturally occurring ligand, found in nature, which binds to a receptor in a manner that is at least equivalent to PUFAs. A "natural ligand" does not refer to an engineered ligand that is not found in nature and that is engineered to bind to a receptor, where it did not formerly do so in a manner different, either in degree or kind, from that which it was engineered to do. Such an engineered ligand is no longer naturally-occurring but is "non-natural" and is derived from a naturally occurring molecule.

As used herein, a "modulator" refers to a compound that increases or decreases the cell surface expression of GPR72, increases or decreases the binding of a ligand to GPR72, or any compound that increases or decreases the intracellular response initiated by an active form of GPR72 either in the presence or absence of a ligand for the receptor, for example PUFA. A modulator includes an agonist, antagonist, inhibitor or inverse agonist, as defined herein. A modulator can be for example, a polypeptide, a peptide, an antibody or antigen-binding fragment thereof, a lipid, a carbohydrate, a nucleic acid, and a small organic molecule. Candidate modulators can be natural or synthetic compounds, including, for example, synthetic small molecules, compounds contained in extracts of animal, plant, bacterial or fungal cells, as well as conditioned medium from such cells.

As used herein, "increase" and "decrease" refer to a change in ligand binding to the GPR72 polypeptide receptor and/or cell signalling through GPR72 polypeptide of at least 10%. An "increase" or "decrease" in binding or signalling is preferably measured in response to contacting GPR72 polypeptide with a ligand in the presence of a candidate modulator, wherein the change in binding or signalling is relative to the binding or signalling in the absence of the candidate modulator.

As used herein, the term "small molecule" refers to a compound having molecular mass of less than 3000 Daltons, preferably less than 2000 or 1500, still more preferably less than 1000, and most preferably less than 600 Daltons. A "small organic molecule" is a small molecule that comprises at least carbon, hydrogen and oxygen atoms.

As used herein, the terms "change", "difference", "decrease", or "increase" as applied to e.g., binding or signalling activity or amount of a substance refer to an at least 10% increase or decrease in binding, signalling activity, or for example, level of mRNA, polypeptide or ligand relative to a standard in a given assay.

As used herein, the term "dysregulation" refers to the signalling activity of GPR72 polypeptide in a sample wherein:

a) a 10% or greater increase or decrease in the amount of one or more of GPR72 polypeptide, ligand or mRNA level is measured relative to a standard, as defined herein, in a given assay or;

b) at least a single base pair change in the GPR72 polypeptide coding sequence is detected relative to SEQ ID NO: 1, and results in an alteration of GPR72 polypeptide ligand binding or signalling activity as defined in paragraphs a), c) or d) or;

c) a 10% or greater increase or decrease in the amount of GPR72 polypeptide ligand binding activity is measured relative to a standard, as defined herein, in a given assay or;

d) a 10% or greater increase or decrease in a second messenger, as defined herein, is measured relative to the standard, as defined herein, in a given assay.

As used herein, the term "conditions permitting the binding of PUFA to a GPR72 polypeptide" refers to conditions of, for example, temperature, salt concentration, pH and protein concentration under which GPR72, binds GPR72 polypeptide. Exact binding conditions will vary depending upon the nature of the assay, for example, whether the assay uses viable cells or only a membrane fraction of cells. However, because GPR72 polypeptide is a cell surface protein favored conditions will generally include physiological salt (90 mM) and pH (about 7.0 to 8.0). Temperatures for binding can vary from 15° C. to 37° C., but will preferably be between room temperature and about 30° C. The concentration of PUFA in a binding reaction will also vary, but will preferably be about 100 nM to 100 μM (e.g., in a reaction with radiolabelled tracer PUFAs).

As used herein, the term "sample" refers to the source of molecules being tested for the presence of an agent or modulator compound that modulates binding to or signalling activity of a GPR72 polypeptide. A sample can be an environmental sample, a natural extract of animal, plant yeast or bacterial cells or tissues, a clinical sample, a synthetic sample, or a conditioned medium from recombinant cells or a fermentation process. The sample may thus contain a variety of different cells. The term "tissue sample" refers to a tissue that is tested for the presence, abundance, quality or an activity of a GPR72 polypeptide, a nucleic acid encoding a GPR72 polypeptide, a GPR72 ligand or an agent or compound that modifies the ligand binding or activity of a GPR72 polypeptide.

As used herein, a "tissue" is an aggregate of cells that perform a particular function in an organism. The term "tissue" as used herein refers to cellular material from a particular physiological region. The cells in a particular tissue can comprise several different cell types. A non-limiting example of this would be brain tissue that further comprises neurons and glial cells, as well as capillary endothelial cells and blood cells, all contained in a given tissue section or sample. In addition to solid tissues, the term "tissue" is also intended to encompass non-solid tissues, such as blood.

As used herein, the term "membrane fraction" refers to a preparation of cellular lipid membranes comprising a GPR72 polypeptide. As the term is used herein, a "membrane fraction" is distinct from a cellular homogenate, in that at least a portion (i.e., at least 10%, and preferably more) of non-membrane-associated cellular constituents has been removed. The term "membrane associated" refers to those cellular constituents that are either integrated into a lipid membrane or are physically associated with a component that is integrated into a lipid membrane.

As used herein, the "second messenger assay" preferably comprises the measurement of guanine nucleotide binding or exchange, adenylate cyclase, intra-cellular cAMP, intracellular inositol phosphate, intra-cellular diacylglycerol concentration, arachidonic acid concentration, MAP kinase(s) or tyrosine kinase(s), protein kinase C activity, or reporter gene expression or an aequorin-based assay according to methods known in the art and defined herein.

As used herein, the term "second messenger" refers to a molecule, generated or caused to vary in concentration by the activation of a G-Protein Coupled Receptor that participates in the transduction of a signal from that GPCR. Non-limiting examples of second messengers include cAMP, diacylglycerol, inositol trisphosphate, arachidonic acid release, and intracellular calcium. The term "change in the level of a second messenger" refers to an increase or decrease of at least 10% in the detected level of a given second messenger relative to the amount detected in an assay performed in the absence of a candidate modulator.

As used herein, the term "aequorin-based assay" refers to an assay for GPCR activity that measures intracellular calcium flux induced by activated GPCRs, wherein intracellular calcium flux is measured by the luminescence of aequorin expressed in the cell.

As used herein, the term "binding" refers to the physical association of a ligand (e.g., a ligand such as PUFAs, or an antibody) with a receptor (e.g., GPR72). As the term is used herein, binding is "specific" if it occurs with an $IC_{50}$ or a $K_d$ of 1 mM less, generally in the range of 100 µM to 100 nM. For example, binding is specific if the $EC_{50}$ or $K_d$ is 100 µM, 50 µM, 10 µM, 1 µM, 950 nM, 900 nM, 850 nM, 800 nM, 750 nM, 700 nM, 650 nM, 600 nM, 550 nM, 500 nM, 450 nM, 350 nM, 300 nM, 250 nM, 200 nM, 150 nM, 100 nM, 75 nM, 50 nM, 25 nM, 10 nM or less.

As used herein, the term "$EC_{50}$," refers to that concentration of a compound at which a given activity, including binding of PUFAs or other ligand and a functional activity of a receptor polypeptide, is 50% of the maximum for that receptor activity measurable using the same assay in the absence of compound. Stated differently, the "$EC_{50}$" is the concentration of compound that gives 50% activation, when 100% activation is set at the amount of activity that does not increase with the addition of more agonist. It should be noted that the "$EC_{50}$" of an analog of PUFA will vary according to the identity of the analogue used in the assay; for example, PUFA analogues can have $EC_{50}$ values higher than, lower than or the same as PUFA. Therefore, where a PUFA analogue differs from PUFA, one of skill in the art can determine the $EC_{50}$ for that analogue according to conventional methods. The $EC_{50}$ of a given PUFA analogue is measured by performing an assay for the activity of a fixed amount of GPR72 polypeptide in the presence of doses of PUFA analogues that increase at least until the GPR72 polypeptide response is saturated or maximal, and then plotting the measured GPR72 polypeptide activity versus the concentration of PUFA analogues.

As used herein, the term "saturation" refers to the concentration of PUFA or other ligand at which further increases in ligand concentration fail to increase the binding of ligand or GPR72 polypeptide-specific signalling activity.

As used herein, the term "$IC_{50}$" is the concentration of an antagonist or inverse agonist that reduces the maximal activation of a GPR72 polypeptide receptor by 50%.

As used herein, the term "LD50" refers to the dose of a particular agent necessary to kill 50% of the subjects to which it is administered.

As used herein, the term "decrease in binding" refers to a decrease of at least 10% in the amount of ligand binding detected in a given assay with a known or suspected modulator of GPR72 polypeptide relative to binding detected in an assay lacking that known or suspected modulator.

As used herein, the term "delivering," when used in reference to a drug or agent, means the addition of the drug or agent to an assay mixture, or to a cell in culture. The term also refers to the administration of the drug or agent to an animal. Such administration can be, for example, by injection (in a suitable carrier, e.g., sterile saline or water) or by inhalation, or by an oral, transdermal, rectal, vaginal, or other common route of drug administration.

As used herein, the term "standard" refers to a sample taken from an individual who is not affected by a disease or disorder characterized by dysregulation of GPR72 polypeptide activity. The "standard" is used as a reference for the comparison of GPR72 mRNA or polypeptide levels and quality (i.e., mutant vs. wild type), as well as for the comparison of GPR72 polypeptide activities. A "standard" also encompasses a reference sequence, e.g., SEQ ID NO: 1 or SEQ ID NO: 2, with which sequences of nucleic acids or their encoded polypeptides are compared.

As used herein, the term "amplifying," when applied to a nucleic acid sequence, refers to a process whereby one or more copies of a nucleic acid sequence is generated from a template nucleic acid. A preferred method of "amplifying" is PCR or RT/PCR.

As used herein, the term "G-Protein coupled receptor," or "GPCR" refers to a membrane-associated polypeptide with 7 alpha helical transmembrane domains. Functional GPCR's associate with a ligand or agonist and also associate with and activate G-proteins. GPR72 polypeptide is a GPCR.

As used herein, the term "antibody" is the conventional immunoglobulin molecule, as well as fragments thereof which are also specifically reactive with one of the subject polypeptides. Antibodies can be fragmented using conventional techniques and the fragments screened for utility in the same manner as described herein below for whole antibodies. For example, $F(ab)_2$ fragments can be generated by treating antibody with pepsin. The resulting $F(ab)_2$ fragment can be treated to reduce disulfide bridges to produce Fab fragments. The antibody of the present invention is further intended to include bispecific, single-chain, and chimeric and humanised molecules having affinity for a polypeptide conferred by at least one CDR region of the antibody. In preferred embodiments, the antibody further comprises a label attached thereto and able to be detected, (e.g., the label can be a radioisotope, fluorescent compound, chemiluminescent compound, enzyme, or enzyme co-factor). The antibodies, monoclonal or polyclonal and its hypervariable portion thereof (F(ab), F(ab') 2, etc.) as well as the hybridoma cell producing the antibodies are a further aspect of the present invention which find a specific industrial application in the field of diagnostics and monitoring of specific diseases, preferably the ones hereafter described.

Inhibitors and modulators according to the invention include but are not limited to monoclonal or polyclonal antibodies or hypervariable portions of the antibodies.

The term "humanized immunoglobulin" as used herein refers to an immunoglobulin comprising portions of immunoglobulins of a different origin, wherein at least one portion is of human origin. Accordingly, the present invention relates to a humanized immunoglobulin which binds human GPR72, said immunoglobulin comprising an antigen-binding region of nonhuman origin (e.g., rodent) and at least a portion of an immunoglobulin of human origin (e.g., a human framework region, a human constant region or portion thereof). For example, the humanized antibody can comprise portions derived from an immunoglobulin of nonhuman origin with the requisite specificity, such as a mouse, and from immunoglobulin sequences of human origin (e.g., a chimeric immunoglobulin), joined together chemically by conventional techniques (e.g., synthetic) or prepared as contiguous polypeptide using genetic engineering techniques (e.g., DNA encoding the protein portions of the chimeric antibody can be expresses to produce a contiguous polypeptide chain). Another example of a humanized immunoglobulin of the present invention is an immunoglobulin containing one or more immunoglobulin chains comprising a CDR of nonhuman origin (e.g., one or more CDRs derived from an antibody of nonhuman origin) and a framework region derived from a light and/or heavy chain of human origin (e.g., CDR-grafted antibodies with or without framework changes).

Such humanized immunoglobulins can be produced using synthetic and/or recombinant nucleic acids to prepare genes (e.g., cDNA) encoding the desired humanized chain. For example, nucleic acid (e.g., DNA) sequences coding for humanized variable regions can be constructed using PCR mutagenesis methods to alter DNA sequences encoding a human or humanized chain, such as a DNA template form a previously humanized variable region (see e.g., Kamman, M., et al., Nucleic Acids Res., 17: 5404 (1989); Sato, K., et al., Cancer Research, 53: 851-856 (1993); Daugherty, B. L. et al., Nucleic Acids Res., 19(9): 2471-2476 (1991); and Lewis, A. P. and J. S Crowe, Gene, 101: 297-302 (1991)). Using these or other suitable methods, variants can also be readily produced. In one embodiment, cloned variable regions can be mutagenized, and sequences encoding variants with the desired specificity can be selected (e.g., from a phage library; see e.g., Krebber et al., U.S. Pat. No. 5,514,548; Hoogenboom et al., WO 93/06213, published Apr. 1, 1993; Knappik et al., WO 97/08320, published Mar. 6, 1997)).

As used herein, the term "transgenic animal" refers to any animal, preferably a non-human mammal, bird, fish or an amphibian, in which one or more of the cells of the animal contain heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical crossbreeding, or in vitro fertilization, but rather is directed to the introduction of a recombinant DNA molecule. This molecule may be integrated within a chromosome, or it may be extra-chromosomally replicating DNA. In the typical transgenic animals described herein, the transgene causes cells to express a recombinant form of one of the subject polypeptide, e.g. either agonistic or antagonistic forms. However, transgenic animals in which the recombinant gene is silent are also contemplated, as for example, the FLP or CRE recombinase dependent constructs described below. Moreover, "transgenic animal" also includes those recombinant animals in which gene disruption of one or more genes is caused by human intervention, including both recombination and antisense techniques.

Sequences

The invention relates to the nucleotide (SEQ ID NO: 1) and amino acid (SEQ ID NO: 2) sequences encoding GPR72 polypeptide (presented in FIG. 1A and FIG. 1B). The invention also relates to sequences that are homologous to the nucleotide and amino acid sequences encoding GPR72 polypeptide.

Calculation of Sequence Homology

Sequence identity with respect to any of the sequences presented herein can be determined by a simple "eyeball" comparison (i.e. a strict comparison) of any one or more of the sequences with another sequence to see if that other sequence has, for example, at least 80% sequence identity to the sequence(s).

Relative sequence identity can also be determined by commercially available computer programs that can calculate % identity between two or more sequences using any suitable algorithm for determining identity, using for example default parameters. A typical example of such a computer program is CLUSTAL. Other computer program methods to determine identity and similarity between two sequences include but are not limited to the GCG program package (Devereux et al 1984 Nucleic Acids Research 12: 387) and FASTA (Atschul et al 1990 J Molec Biol 403-410).

% homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example, when using the GCG Wisconsin Bestfit package the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (University of Wisconsin, U.S.A.; Devereux et al., 1984, Nucleic Acids Research 12:387). Examples of other software that can perform sequence comparisons include, but are not limited to, the BLAST package (Ausubel et al., 1995, *Short Protocols in Molecular Biology*, 3rd Edition, John Wiley & Sons), FASTA (Atschul et al., 1990, J. Mol. Biol., 403-410) and the GENEWORKS suite of comparison tools. Both BLAST and FASTA are available for offline and online searching (Ausubel et al., 1999 supra, pages 7-58 to 7-60).

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied. It is preferred to use the public default values for the GCG package, or in the case of other software, the default matrix, such as BLOSUM62.

Advantageously, the BLAST algorithm is employed, with parameters set to default values. The BLAST algorithm is described in detail at the website of the National Center for Biotechnology Information. The search parameters are defined as follows, and can be advantageously set to the defined default parameters.

Advantageously, "substantial identity" when assessed by BLAST equates to sequences which match with an EXPECT value of at least about 7, preferably at least about 9 and most preferably 10 or more. The default threshold for EXPECT in BLAST searching is usually 10.

BLAST (Basic Local Alignment Search Tool) is the heuristic search algorithm employed by the programs blastp, blastn, blastx, tblastn, and tblastx; these programs ascribe significance to their findings using the statistical methods of Karlin and Altschul (Karlin and Altschul 1990, Proc. Natl. Acad. Sci. USA 87:2264-68; and Karlin and Altschul, 1993, Proc. Natl. Acad. Sci. USA 90:5873-7), with a few enhancements. The BLAST programs are tailored for sequence similarity searching, for example to identify homologues to a query sequence. For a discussion of basic issues in similarity searching of sequence databases, see Altschul et al (1994) Nature Genetics 6:119-129.

The five BLAST programs available at the website of the National Center for Biotechnology Information perform the following tasks: blastp—compares an amino acid query sequence against a protein sequence database; blastn—compares a nucleotide query sequence against a nucleotide sequence database; blastx—compares the six-frame conceptual translation products of a nucleotide query sequence (both strands) against a protein sequence database; tblastn—compares a protein query sequence against a nucleotide sequence database dynamically translated in all six reading frames (both strands); tblastx—compares the six-frame translations of a nucleotide query sequence against the six-frame translations of a nucleotide sequence database.

BLAST uses the following search parameters:

HISTOGRAM—Display a histogram of scores for each search; default is yes. (See parameter H in the BLAST Manual).

DESCRIPTIONS—Restricts the number of short descriptions of matching sequences reported to the number specified; default limit is 100 descriptions. (See parameter V in the manual page).

EXPECT—The statistical significance threshold for reporting matches against database sequences; the default value is 10, such that 10 matches are expected to be found merely by chance, according to the stochastic model of Karlin and Altschul (1990). If the statistical significance ascribed to a match is greater than the EXPECT threshold, the match will not be reported. Lower EXPECT thresholds are more stringent, leading to fewer chance matches being reported. Fractional values are acceptable. (See parameter E in the BLAST Manual).

CUTOFF—Cutoff score for reporting high-scoring segment pairs. The default value is calculated from the EXPECT value (see above). HSPs are reported for a database sequence only if the statistical significance ascribed to them is at least as high as would be ascribed to a lone HSP having a score equal to the CUTOFF value. Higher CUTOFF values are more stringent, leading to fewer chance matches being reported. (See parameter S in the BLAST Manual). Typically, significance thresholds can be more intuitively managed using EXPECT.

ALIGNMENTS—Restricts database sequences to the number specified for which high-scoring segment pairs (HSPs) are reported; the default limit is 50. If more database sequences than this happen to satisfy the statistical significance threshold for reporting (see EXPECT and CUTOFF below), only the matches ascribed the greatest statistical significance are reported. (See parameter B in the BLAST Manual).

MATRIX—Specify an alternate scoring matrix for BLASTP, BLASTX, TBLASTN and TBLASTX. The default matrix is BLOSUM62 (Henikoff & Henikoff, 1992). The valid alternative choices include: PAM40, PAM120, PAM250 and IDENTITY. No alternate scoring matrices are available for BLASTN; specifying the MATRIX directive in BLASTN requests returns an error response.

STRAND—Restrict a TBLASTN search to just the top or bottom strand of the database sequences; or restrict a BLASTN, BLASTX or TBLASTX search to just reading frames on the top or bottom strand of the query sequence.

FILTER—Mask off segments of the query sequence that have low compositional complexity, as determined by the SEG program of Wootton & Federhen (1993) Computers and Chemistry 17:149-163, or segments consisting of short-periodicity internal repeats, as determined by the XNU program of Claverie & States (1993) Computers and Chemistry 17:191-201, or, for BLASTN, by the DUST program of Tatusov and Lipman. Filtering can eliminate statistically significant but biologically uninteresting reports from the blast output (e.g., hits against common acidic-, basic- or proline-rich regions), leaving the more biologically interesting regions of the query sequence available for specific matching against database sequences.

Low complexity sequence found by a filter program is substituted using the letter "N" in nucleotide sequence (e.g., "NNNNNNNNNNNNN") and the letter "X" in protein sequences (e.g., "XXXXXXXXX").

Filtering is only applied to the query sequence (or its translation products), not to database sequences. Default filtering is DUST for BLASTN, SEG for other programs.

It is not unusual for nothing at all to be masked by SEG, XNU, or both, when applied to sequences in SWISS-PROT, so filtering should not be expected to always yield an effect. Furthermore, in some cases, sequences are masked in their entirety, indicating that the statistical significance of any matches reported against the unfiltered query sequence should be suspect.

NCBI-gi—Causes NCBI gi identifiers to be shown in the output, in addition to the accession and/or locus name.

Most preferably, sequence comparisons are conducted using the simple BLAST search algorithm provided at the website of the National Center for Biotechnology Information. In some embodiments of the present invention, no gap penalties are used when determining sequence identity.

Cells

A cell that is useful according to the invention is preferably selected from the group consisting of bacterial cells, yeast cells, insect cells or mammalian cells.

A cell that is useful according to the invention can be any cell into which a nucleic acid sequence encoding a receptor according to the invention can be introduced such that the receptor is expressed at natural levels or above natural levels, as defined herein. Preferably a receptor of the invention that is expressed in a cell exhibits normal or near normal pharmacology, as defined herein. Most preferably a receptor of the invention that is expressed in a cell comprises the nucleotide represented by SEQ ID NO: 1 or amino acid sequence represented by SEQ ID NO: 2 or a nucleotide or amino acid sequence that is at least 70% identical to the amino acid sequence represented by SEQ ID NO: 2. Preferably, a receptor of the invention that is expressed in a cell will bind PUFA.

According to a preferred embodiment of the present invention, a cell is selected from the group consisting of COS7- cells, a CHO cell, a LM (TK-) cell, a NIH-3T3 cell, HEK-293 cell, K-562 cell or a 1321N1 astrocytoma cell but also other transfectable cell lines.

Assays

I. Assays for the Identification of Agents that Modulate the Activity of GPR72 Polypeptide Agents that modulate the activity of GPR72 polypeptide can be identified in a number of ways that take advantage of the newly discovered interaction of the receptor with PUFAs. For example, the ability to reconstitute GPR72 polypeptide/PUFA binding either in vitro, on cultured cells or in vivo provides a target for the identification of agents that disrupt that binding. Assays based on disruption of binding can identify agents, such as small organic molecules, from libraries or collections of such molecules. Alternatively, such assays can identify agents in samples or extracts from natural sources, e.g., plant, fungal or bacterial extracts or even in human tissue samples (e.g., tumor tissue). In one aspect, the extracts can be made from cells expressing a library of variant nucleic acids, peptides or polypeptides. Modulators of GPR72 polypeptide/PUFA binding can then be screened using a binding assay or a functional assay that measures downstream signalling through the receptor.

Another approach that uses the GPR72 polypeptide/PUFA interaction more directly to identify agents that modulate GPR72 polypeptide function measures changes in GPR72 polypeptide downstream signalling induced by candidate agents or candidate modulators. These functional assays can be performed in isolated cell membrane fractions or on cells expressing the receptor on their surfaces.

The finding that PUFAs is a ligand of the GPR72 polypeptide receptor permits screening assays to identify agonists, antagonists and inverse agonists of receptor activity. The screening assays have two general approaches, detailed below. For the purposes of this section PUFAs as defined herein is used as an exemplary ligand. It should be understood, however, that any AA-PUFAs as defined herein can be used in the assays described.

1) Ligand binding assays, in which cells expressing GPR72 polypeptide, membrane extracts from such cells, or immobilized lipid membranes comprising GPR72 polypeptide are exposed to labelled and candidate compound. Following incubation, the reaction mixture is measured for specific binding of the labelled to the GPR72 polypeptide receptor. Compounds that interfere with binding or displace labelled can be agonists, antagonists or inverse agonists of GPR72 polypeptide activity. Subsequent functional analysis can then be performed on positive compounds to determine in which of these categories they belong.

2) Functional assays, in which a signalling activity of GPR72 polypeptide is measured.

a) For agonist screening, cells expressing GPR72 polypeptide or membranes prepared from them are incubated with a candidate compound, and a signalling activity of GPR72 polypeptide is measured. The activity induced by compounds that modulate receptor activity is compared to that induced by the natural ligand, a PUFA. An agonist or partial agonist will have a maximal biological activity corresponding to at least 10% of the maximal activity of PUFA when the agonist or partial agonist is present at 1 mM or less, and preferably will have a potency which is at least as potent as PUFA.

b) For antagonist or inverse agonist screening, cells expressing GPR72 polypeptide or membranes isolated from them are assayed for signalling activity in the presence of PUFA with or without a candidate compound. Antagonists will reduce the level of PUFA-stimulated receptor activity by at least 10%, relative to reactions lacking the antagonist in the presence of PUFA. Inverse agonists will reduce the constitutive activity of the receptor by at least 10%, relative to reactions lacking the inverse agonist.

c) For inverse agonist screening, cells expressing constitutive GPR72 polypeptide activity or membranes isolated from them are used in a functional assay that measures an activity of the receptor in the presence of a candidate compound. Inverse agonists are those compounds that reduce the constitutive activity of the receptor by at least 10%. Overexpression of GPR72 polypeptide may lead to constitutive activation. GPR72 polypeptide can be overexpressed by placing it under the control of a strong constitutive promoter, e.g., the CMV early promoter. Alternatively, certain mutations of conserved GPCR amino acids or amino acid domains tend to lead to constitutive activity. See for example: Kjelsberg et al., 1992, J. Biol. Chem. 267:1430; McWhinney et al., 2000. J. Biol. Chem. 275:2087; Ren et al., 1993, J. Biol. Chem. 268:16483; Samama et al., 1993, J. Biol. Chem. 268:4625; Parma et al., 1993, Nature 365:649; Parma et al., 1998, J. Pharmacol. Exp. Ther. 286:85; and Parent et al., 1996, J. Biol. Chem. 271: 7949.

Ligand Binding and Displacement Assays:

As noted in (1) above, one can use GPR72 polypeptides expressed on a cell, or isolated membranes containing receptor polypeptides, along with PUFA in order to screen for compounds that inhibit the binding of PUFA to GPR72 polypeptide. For the purposes of this section, PUFA is used as an exemplary ligand. It should be understood however that any AA-PUFA as defined herein can be used in the assays described.

For displacement experiments, cells expressing a GPR72 polypeptide (generally 25,000 cells per assay or 1 to 100 µg of membrane extracts) are incubated in binding buffer with labelled PUFA in the presence or absence of increasing concentrations of a candidate modulator. To validate and calibrate the assay, control competition reactions using increasing concentrations of unlabeled PUFA can be performed. After incubation, cells are washed extensively, and bound, labelled PUFA is measured as appropriate for the given label (e.g., scintillation counting, fluorescence, etc.). A decrease of at least 10% in the amount of labelled PUFA bound in the presence of candidate modulator indicates displacement of binding by the candidate modulator. Candidate modulators are considered to bind specifically in this or other assays described herein if they displace 50% of labelled PUFA (sub-saturating PUFA dose) at a concentration of 1 mM or less.

Alternatively, binding or displacement of binding can be monitored by surface plasmon resonance (SPR). Surface plasmon resonance assays can be used as a quantitative method to measure binding between two molecules by the change in mass near an immobilized sensor caused by the binding or loss of binding of PUFA from the aqueous phase to a GPR72 polypeptide immobilized in a membrane on the sensor. This change in mass is measured as resonance units versus time after injection or removal of the PUFA or candidate modulator and is measured using a Biacore Biosensor (Biacore AB). GPR72 polypeptide can be immobilized on a sensor chip (for example, research grade CM5 chip; Biacore AB) in a thin film lipid membrane according to methods described by Salamon et al. (Salamon et al., 1996, Biophys J. 71: 283-294; Salamon et al., 2001, Biophys. J. 80: 1557-1567; Salamon et al., 1999, Trends Biochem. Sci. 24: 213-219, each of which is incorporated herein by reference.). Sarrio et al. demonstrated that SPR can be used to detect ligand binding to the GPCR A(1) adenosine receptor immobilized in a lipid layer on the chip (Sarrio et al., 2000, Mol. Cell. Biol. 20: 5164-5174, incorporated herein by reference).

Conditions for PUFA binding to GPR72 polypeptide in an SPR assay can be fine-tuned by one of skill in the art using the conditions reported by Sarrio et al. as a starting point.

SPR can assay for modulators of binding in at least two ways. First, PUFA can be pre-bound to immobilized GPR72 polypeptide, followed by injection of candidate modulator at a concentration ranging from 100 nM to 100 µM. Displacement of the bound PUFA can be quantitated, permitting detection of modulator binding. Alternatively, the membrane-bound GPR72 polypeptide can be pre-incubated with candidate modulator and challenged with PUFA. A difference in PUFA binding to the GPR72 polypeptide exposed to modulator relative to that on a chip not pre-exposed to modulator will demonstrate binding or displacement of PUFA in the presence of modulator. In either assay, a decrease of 10% or more in the amount of PUFA bound in the presence of candidate modulator, relative to the amount of a PUFAs bound in the absence of candidate modulator indicates that the candidate modulator inhibits the interaction of GPR72 polypeptide and PUFA.

Another method of detecting inhibition of binding of PUFA to GPR72 polypeptide uses fluorescence resonance energy transfer (FRET). FRET is a quantum mechanical phenomenon that occurs between a fluorescence donor (D) and a fluorescence acceptor (A) in close proximity to each other (usually <100 A of separation) if the emission spectrum of D overlaps with the excitation spectrum of A. The molecules to be tested, e.g. PUFAs and a GPR72 polypeptide, are labelled with a complementary pair of donor and acceptor fluorophores. While bound closely together by the GPR72 polypeptide: PUFA interaction, the fluorescence emitted upon excitation of the donor fluorophore will have a different wavelength than that emitted in response to that excitation wavelength when the PUFA and GPR72 polypeptide are not bound, providing for quantitation of bound versus unbound molecules by measurement of emission intensity at each wavelength. Donor fluorophores with which to label the GPR72 polypeptide are well known in the art. Of particular interest are variants of the A. victoria GFP known as Cyan FP (CFP, Donor (D)) and Yellow FP (YFP, Acceptor(A)). As an example, the YFP variant can be made as a fusion protein with GPR72 polypeptide. Vectors for the expression of GFP variants as fusions (Clontech) as well as fluorophore-labeled compounds (Molecular Probes) are known in the art. The addition of a candidate modulator to the mixture of labelled PUFAs and YFP-GPR72 protein will result in an inhibition of energy transfer evidenced by, for example, a decrease in YFP fluorescence relative to a sample without the candidate modulator. In an assay using FRET for the detection of GPR72 polypeptide: PUFA interaction, a 10% or greater decrease in the intensity of fluorescent emission at the acceptor wavelength in samples containing a candidate modulator, relative to samples without the candidate modulator, indicates that the candidate modulator inhibits the GPR72 polypeptide: PUFA interaction.

A variation on FRET uses fluorescence quenching to monitor molecular interactions. One molecule in the interacting pair can be labelled with a fluorophore, and the other with a molecule that quenches the fluorescence of the fluorophore when brought into close apposition with it. A change in fluorescence upon excitation is indicative of a change in the association of the molecules tagged with the fluorophore:quencher:quencher pair. Generally, an increase in fluorescence of the labelled GPR72 polypeptide is indicative that the PUFA molecule bearing the quencher has been displaced. For quenching assays, a 10% or greater increase in the intensity of fluorescent emission in samples containing a candidate modulator, relative to samples without the candidate modulator, indicates that the candidate modulator inhibits GPR72 polypeptide: PUFA interaction.

In addition to the surface plasmon resonance and FRET methods, fluorescence polarization measurement is useful to quantitate binding. The fluorescence polarization value for a fluorescently-tagged molecule depends on the rotational correlation time or tumbling rate. Complexes, such as those formed by GPR72 polypeptide associating with a fluorescently labelled PUFA, have higher polarization values than uncomplexed, labelled PUFA. The inclusion of a candidate inhibitor of the GPR72 polypeptide: PUFA interaction results in a decrease in fluorescence polarization, relative to a mixture without the candidate inhibitor, if the candidate inhibitor disrupts or inhibits the interaction of GPR72 polypeptide with PUFA. Fluorescence polarization is well suited for the identification of small molecules that disrupt the formation of receptor:ligand complexes. A decrease of 10% or more in fluorescence polarization in samples containing a candidate modulator, relative to fluorescence polarization in a sample lacking the candidate modulator, indicates that the candidate modulator inhibits GPR72 polypeptide: PUFA interaction.

Another alternative for monitoring GPR72 polypeptide: PUFA interactions uses a biosensor assay. ICS biosensors have been described in the art (Australian Membrane Biotechnology Research Institute; www.ambri.com.au/; Cornell B, Braach-Maksvytis V, King L, Osman P, Raguse B, Wieczorek L, and Pace R. "A biosensor that uses ion-channel switches" Nature 1997, 387, 580). In this technology, the association of GPR72 polypeptide and its ligand is coupled to the closing of gramacidin-facilitated ion channels in suspended membrane bilayers and thus to a measurable change in the admittance (similar to impedance) of the biosensor. This approach is linear over six orders of magnitude of admittance change and is ideally suited for large scale, high throughput screening of small molecule combinatorial libraries. A 10% or greater change (increase or decrease) in admittance in a sample containing a candidate modulator, relative to the admittance of a sample lacking the candidate modulator, indicates that the candidate modulator inhibits the interaction of GPR72 polypeptide and PUFA. It is important to note that in assays testing the interaction of GPR72 polypeptide with PUFA, it is possible that a modulator of the interaction need not necessarily interact directly with the domain(s) of the proteins that physically interact with PUFA. It is also possible that a modulator will interact at a location removed from the site of interaction and cause, for example, a conformational change in the GPR72 polypeptide. Modulators (inhibitors or agonists) that act in this manner are nonetheless of interest as agents to modulate the activity of GPR72 polypeptide.

It should be understood that any of the binding assays described herein can be performed with a non-PUFA ligand or a non AA-PUFA ligand (for example, agonist, antagonist, etc.) of GPR72 polypeptide, e.g., a small molecule identified as described herein or PUFA analogues including but not limited to any of the PUFA analogues, a natural or synthetic peptide, a polypeptide, an antibody or antigen-binding fragment thereof, a lipid, a carbohydrate, and a small organic molecule.

Any of the binding assays described can be used to determine the presence of an agent in a sample, e.g., a tissue sample, that binds to the GPR72 polypeptide receptor molecule, or that affects the binding of PUFA to the receptor. To do so, GPR72 polypeptide is reacted with PUFAs or another ligand in the presence or absence of the sample, and PUFA or ligand binding is measured as appropriate for the binding assay being used. A decrease of 10% or more in the binding of PUFA or other ligand indicates that the sample contains an agent that modulates PUFA or ligand binding to the receptor polypeptide.

Functional Assays of Receptor Activity i. GTPase/GTP Binding Assays:

For GPCRs such as GPR72 polypeptide, a measure of receptor activity is the binding of GTP by cell membranes containing receptors. In the method described by Traynor and Nahorski, 1995, Mol. Pharmacol. 47: 848-854, incorporated herein by reference, one essentially measures G-protein coupling to membranes by detecting the binding of labelled GTP. For GTP binding assays, membranes isolated from cells expressing the receptor are incubated in a buffer containing 20 mM HEPES, pH 7.4, 100 mM NaCl, and 10 mM MgCl2, 80 µM $^{35}$S-GTPγS and 3 µM GDP. The assay mixture is incubated for 60 minutes at 30° C., after which unbound labelled GTP is removed by filtration onto GF/B filters. Bound, labelled GTP is measured by liquid or solid (SPA, see below) scintillation counting. In order to assay for modulation of PUFA-induced GPR72 polypeptide activity, membranes prepared from cells expressing a GPR72 polypeptide are mixed with PUFA, and the GTP binding assay is performed in the presence and absence of a candidate modulator of GPR72 polypeptide activity. A decrease of 10% or more in labelled GTP binding as measured by scintillation counting in an assay of this kind containing a candidate modulator, relative to an assay without the modulator, indicates that the candidate modulator inhibits GPR72 polypeptide activity. A similar GTP-binding assay can be performed without PUFA to identify compounds that act as agonists. In this case, PUFA-stimulated GTP binding is used as a standard. A compound is considered an agonist if it induces at least 50, 40, 30, or preferably 20% of the level of GTP binding induced by PUFA when the compound is present at 100 µM or less, and preferably will induce a level the same as or higher than that induced by PUFA.

Scintillation Proximity Assay (SPA) is an homogeneous screening technology applied to receptor binding assays by immobilizing receptors directly onto SPA beads via a suitable coupling method. Once immobilized, the receptor is close enough to the bead so that, should a suitably radiolabelled ligand bind to the receptor, it will be in close enough proximity to stimulate the bead to emit light. Any unbound radioligand is too distant from the bead to transfer energy and goes undetected. The bead, therefore, only detects the population of ligand molecules which are receptor bound. The discrimination of binding by proximity means that no separation of bound and free ligand is required, as in traditional methods. The method is generally applicable to [$^{3}$H], [$^{125}$I], [$^{35}$S] ligands. Approaches involving antibodies and biotinylation can be used for soluble receptors GTPase activity is measured by incubating the membranes containing a GPR72 polypeptide with γ$^{32}$P-GTP. Active GTPase will release the label as inorganic phosphate, which is detected by separation of free inorganic phosphate in a 5% suspension of activated charcoal in 20 mM $H_3PO_4$, followed by scintillation counting. Controls include assays using membranes isolated from cells not expressing GPR72 polypeptide (mock-transfected), in order to exclude possible non-specific effects of the candidate compound.

In order to assay for the effect of a candidate modulator on GPR72 polypeptide-regulated GTPase activity, membrane samples are incubated with PUFAs, with or without the modulator, followed by the GTPase assay. A change (increase or decrease) of 10% or more in the level of GTP binding or GTPase activity relative to samples without modulator is indicative of GPR72 polypeptide modulation by a candidate modulator.

ii. Downstream Pathway Activation Assays:

a. Calcium Flux—The Aequorin-Based Assay.

The aequorin assay takes advantage of the responsiveness of mitochondrial apoaequorin to intracellular calcium release induced by the activation of GPCRs (Stables et al., 1997, Anal. Biochem. 252:115-126; Detheux et al., 2000, J. Exp. Med., 192 1501-1508; both of which are incorporated herein by reference). Briefly, GPR72 polypeptide-expressing clones are transfected to coexpress mitochondrial apoaequorin and Gα16. Cells are incubated with 5 µM Coelenterazine H (Molecular Probes) for 4 hours at room temperature, washed in DMEM-F12 culture medium and resuspended at a concentration of 0.5×10$^6$ cells/ml. Cells are then mixed with test agonist molecules and light emission by the aequorin is recorded with a luminometer for 30 sec. Results are expressed as Relative Light Units (RLU). Controls include assays using membranes isolated from cells not expressing GPR72 polypeptide (mock transfected), in order to exclude possible non-specific effects of the candidate compound.

Aequorin activity or intracellular calcium levels are "changed" if light intensity increases or decreases by 10% or more in a sample of cells, expressing a GPR72 polypeptide and treated with a candidate modulator, relative to a sample of cells expressing the GPR72 polypeptide but not treated with the candidate modulator or relative to a sample of cells not expressing the GPR72 polypeptide (mock-transfected cells) but treated with the candidate modulator.

When performed in the absence of PUFA, the assay can be used to identify an agonist of GPR72 polypeptide activity. When the assay is performed in the presence of PUFA, it can be used to assay for an antagonist.

b. Adenylate Cyclase Assay:

Assays for adenylate cyclase activity are described by Kenimer & Nirenberg, 1981, Mol. Pharmacol. 20: 585-591, incorporated herein by reference. That assay is a modification of the assay taught by Solomon et al., 1974, Anal. Biochem. 58: 541-548, also incorporated herein by reference. Briefly, 100 µl reactions contain 50 mM Tris-Hcl (pH 7.5), 5 mM $MgCl_2$, 20 mM creatine phosphate (disodium salt), 10 units (71 µg of protein) of creatine phosphokinase, 1 mM α-$^{32}$P-ATP (tetrasodium salt, 2 µCi), 0.5 mM cyclic AMP, G-3H-labeled cyclic AMP (approximately 10,000 cpm), 0.5 mM Ro20-1724, 0.25% ethanol, and 50-200 µg of protein homogenate to be tested (i.e., homogenate from cells expressing or not expressing a GPR72 polypeptide, treated or not treated with PUFAs with or without a candidate modulator). Reaction mixtures are generally incubated at 37° C. for 60 minutes. Following incubation, reaction mixtures are deproteinized by the addition of 0.9 ml of cold 6% trichloroacetic acid. Tubes are centrifuged at 1800×g for 20 minutes and each supernatant solution is added to a Dowex AG50W-X4 column. The cAMP fraction from the column is eluted with 4 ml of 0.1 mM imidazole-HCl (pH 7.5) into a counting vial. Assays should be performed in triplicate. Control reactions should also be performed using protein homogenate from cells that do not express a GPR72 polypeptide.

According to the invention, adenylate cyclase activity is "changed" if it increases or decreases by 10% or more in a sample taken from cells treated with a candidate modulator of GPR72 polypeptide activity, relative to a similar sample of cells not treated with the candidate modulator or relative to a sample of cells not expressing the GPR72 polypeptide (mock-transfected cells) but treated with the candidate modulator.

c. cAMP Assay:

Intracellular or extracellular cAMP is measured using a cAMP radioimmunoassay (RIA) or cAMP binding protein according to methods widely known in the art. For example, Horton & Baxendale, 1995, Methods Mol. Biol. 41: 91-105, which is incorporated herein by reference, describes an RIA for cAMP.

A number of kits for the measurement of cAMP are commercially available, such as the High Efficiency Fluorescence Polarization-based homogeneous assay marketed by LJL Biosystems and NEN Life Science Products. Control reactions should be performed using extracts of mock-transfected cells to exclude possible non-specific effects of some candidate modulators.

The level of cAMP is "changed" if the level of cAMP detected in cells, expressing a GPR72 polypeptide and treated with a candidate modulator of GPR72 polypeptide activity (or in extracts of such cells), using the RIA-based assay of Horton & Baxendale, 1995, supra, increases or decreases by at least 10% relative to the cAMP level in similar cells not treated with the candidate modulator.

d. Phospholipid Breakdown, DAG Production and Inositol Trisphosphate Levels:

Receptors that activate the breakdown of phospholipids can be monitored for changes due to the activity of known or suspected modulators of GPR72 polypeptide by monitoring phospholipid breakdown, and the resulting production of second messengers DAG and/or inositol trisphosphate (IP$_3$). Methods of detecting each of these are described in *Phospholipid Signalling Protocols*, edited by Ian M. Bird. Totowa, N.J., Humana Press, 1998, which is incorporated herein by reference. See also Rudolph et al., 1999, J. Biol. Chem. 274: 11824-11831, incorporated herein by reference, which also describes an assay for phosphatidylinositol breakdown. Assays should be performed using cells or extracts of cells expressing GPR72 polypeptide, treated or not treated with PUFA with or without a candidate modulator. Control reactions should be performed using mock-transfected cells, or extracts from them in order to exclude possible non-specific effects of some candidate modulators.

According to the invention, phosphatidylinositol breakdown, and diacylglycerol and/or inositol trisphosphate levels are "changed" if they increase or decrease by at least 10% in a sample from cells expressing a GPR72 polypeptide and treated with a candidate modulator, relative to the level observed in a sample from cells expressing a GPR72 polypeptide that is not treated with the candidate modulator.

e. PKC Activation Assays:

Growth factor receptor tyrosine kinases can signal via a pathway involving activation of Protein Kinase C (PKC), which is a family of phospholipid- and calcium-activated protein kinases. PKC activation ultimately results in the transcription of an array of proto-oncogene transcription factor-encoding genes, including c-fos, c-myc and c-jun, proteases, protease inhibitors, including collagenase type I and plasminogen activator inhibitor, and adhesion molecules, including intracellular adhesion molecule I (ICAM I). Assays designed to detect increases in gene products induced by PKC can be used to monitor PKC activation and thereby receptor activity. In addition, the activity of receptors that signal via PKC can be monitored through the use of reporter gene constructs driven by the control sequences of genes activated by PKC activation. This type of reporter gene-based assay is discussed in more detail below.

For a more direct measure of PKC activity, the method of Kikkawa et al., 1982, J. Biol. Chem. 257: 13341, incorporated herein by reference, can be used. This assay measures phosphorylation of a PKC substrate peptide, which is subsequently separated by binding to phosphocellulose paper. This PKC assay system can be used to measure activity of purified kinase, or the activity in crude cellular extracts. Protein kinase C sample can be diluted in 20 mM HEPES/2 mM DTT immediately prior to assay.

The substrate for the assay is the peptide Ac-FKKSFKL-NH2 (SEQ ID NO: 5), derived from the myristoylated alanine-rich protein kinase C substrate protein (MARCKS). The $K_m$ of the enzyme for this peptide is approximately 50 µM. Other basic, protein kinase C-selective peptides known in the art can also be used, at a concentration of at least 2-3 times their $K_m$. Cofactors required for the assays include calcium, magnesium, ATP, phosphatidylserine and diacylglycerol. Depending upon the intent of the user, the assay can be performed to determine the amount of PKC present (activating conditions) or the amount of active PKC present (non-activating conditions). For most purposes according to the invention, non-activating conditions will be used, such that the PKC, that is active in the sample when it is isolated, is measured, rather than measuring the PKC that can be activated. For non-activating conditions, calcium is omitted from the assay in favor of EGTA.

The assay is performed in a mixture containing 20 mM HEPES, pH 7.4, 1-2 mM DTT, 5 mM MgCl$_2$, 100 µM ATP, ~1 µCi γ-$^{32}$P-ATP, 100 µg/ml peptide substrate (~100 µM), 140 µM/3.8 µM phosphatidylserine/diacylglycerol membranes, and 100 µM calcium (or 500 µM EGTA). 48 µl of sample, diluted in 20 mM HEPES, pH 7.4, 2 mM DTT is used in a final reaction volume of 80 µl. Reactions are performed at 30° C. for 5-10 minutes, followed by addition of 25 µl of 100 mM ATP, 100 mM EDTA, pH 8.0, which stops the reactions.

After the reaction is stopped, a portion (85 µl) of each reaction is spotted onto a Whatman P81 cellulose phosphate filter, followed by washes: four times 500 ml in 0.4% phosphoric acid, (5-10 min per wash); and a final wash in 500 ml 95% EtOH, for 2-5 min. Bound radioactivity is measured by scintillation counting. Specific activity (cpm/nmol) of the labelled ATP is determined by spotting a sample of the reaction onto P81 paper and counting without washing. Units of PKC activity, defined as nmol phosphate transferred per min, are calculated as follows:

The activity, in UNITS (nmol/min) is:

$$\text{The activity, in UNITS (nmol/min) is:} = \frac{(\text{cpm on paper}) \times (105 \text{ µl total}/85 \text{ µl spotted})}{(\text{assay time, min})(\text{specific activity of } ATP \text{ cpm/nmol})}.$$

An alternative assay can be performed using a Protein Kinase C Assay Kit sold by PanVera (Cat. #P2747).

Assays are performed on extracts from cells expressing a GPR72 polypeptide, treated or not treated with PUFA with or without a candidate modulator. Control reactions should be performed using mock-transfected cells, or extracts from them in order to exclude possible non-specific effects of some candidate modulators.

According to the invention, PKC activity is "changed" by a candidate modulator when the units of PKC measured by either assay described above increase or decrease by at least 10%, in extracts from cells expressing GPR72 polypeptide and treated with a candidate modulator, relative to a reaction performed on a similar sample from cells not treated with a candidate modulator.

f. Kinase Assays:

MAP kinase activity can be assayed using any of several kits available commercially, for example, the p38 MAP Kinase assay kit sold by New England Biolabs (Cat #9820) or the FlashPlate™ MAP Kinase assays sold by Perkin-Elmer Life Sciences.

MAP Kinase activity is "changed" if the level of activity is increased or decreased by 10% or more in a sample from cells, expressing a GPR72 polypeptide, treated with a candidate modulator relative to MAP kinase activity in a sample from similar cells not treated with the candidate modulator.

Direct assays for tyrosine kinase activity using known synthetic or natural tyrosine kinase substrates and labelled phosphate are well known, as are similar assays for other types of kinases (e.g., Ser/Thr kinases). Kinase assays can be performed with both purified kinases and crude extracts prepared from cells expressing a GPR72 polypeptide, treated with or without PUFA, with or without a candidate modulator. Control reactions should be performed using mock-transfected cells, or extracts from them in order to exclude possible non-specific effects of some candidate modulators. Substrates can be either full-length protein or synthetic peptides representing the substrate. Pinna & Ruzzene (1996, Biochem. Biophys. Acta 1314: 191-225, incorporated herein by reference) list a number of phosphorylation substrate sites useful for detecting kinase activities. A number of kinase substrate peptides are commercially available. One that is particularly useful is the "Src-related peptide," RRLIEDAEYAARG (SEQ ID NO: 6; available from Sigma # A7433), which is a substrate for many receptor and nonreceptor tyrosine kinases. Because the assay described below requires binding of peptide substrates to filters, the peptide substrates should have a net positive charge to facilitate binding. Generally, peptide substrates should have at least 2 basic residues and a free amino terminus. Reactions generally use a peptide concentration of 0.7-1.5 mM.

Assays are generally carried out in a 25 µl volume comprising 5 µl of 5× kinase buffer (5 mg/mL BSA, 150 mM Tris-Cl (pH 7.5), 100 mM $MgCl_2$; depending upon the exact kinase assayed for, $MnCl_2$ can be used in place of or in addition to the $MgCl_2$), 5 µl of 1.0 mM ATP (0.2 mM final concentration), γ-32P-ATP (100-500 cpm/pmol), 3 µl of 10 mM peptide substrate (1.2 mM final concentration), cell extract containing kinase to be tested (cell extracts used for kinase assays should contain a phosphatase inhibitor (e.g. 0.1-1 mM sodium orthovanadate)), and $H_2O$ to 25 µl. Reactions are performed at 30° C., and are initiated by the addition of the cell extract.

Kinase reactions are performed for 30 seconds to about 30 minutes, followed by the addition of 45 µl of ice-cold 10% trichloroacetic acid (TCA). Samples are spun for 2 minutes in a microcentrifuge, and 35 µl of the supernatant is spotted onto Whatman P81 cellulose phosphate filter circles. The filters are washed three times with 500 ml cold 0.5% phosphoric acid, followed by one wash with 200 ml of acetone at room temperature for 5 minutes. Filters are dried and incorporated $^{32}P$ is measured by scintillation counting. The specific activity of ATP in the kinase reaction (e.g., in cpm/pmol) is determined by spotting a small sample (2-5 µl) of the reaction onto a P81 filter circle and counting directly, without washing. Counts per minute obtained in the kinase reaction (minus blank) are then divided by the specific activity to determine the moles of phosphate transferred in the reaction.

Tyrosine kinase activity is "changed" if the level of kinase activity is increased or decreased by 10% or more in a sample from cells, expressing a GPR72 polypeptide, treated with a candidate modulator relative to kinase activity in a sample from similar cells not treated with the candidate modulator.

g. Transcriptional Reporters for Downstream Pathway Activation:

The intracellular signal initiated by binding of an agonist to a receptor, e.g., GPR72 polypeptide, sets in motion a cascade of intracellular events, the ultimate consequence of which is a rapid and detectable change in the transcription or translation of one or more genes. The activity of the receptor can therefore be monitored by detecting the expression of a reporter gene driven by control sequences responsive to GPR72 activation.

As used herein "promoter" refers to the transcriptional control elements necessary for receptor-mediated regulation of gene expression, including not only the basal promoter, but also any enhancers or transcription-factor binding sites necessary for receptor-regulated expression. By selecting promoters that are responsive to the intracellular signals resulting from agonist binding, and operatively linking the selected promoters to reporter genes whose transcription, translation or ultimate activity is readily detectable and measurable, the transcription based reporter assay provides a rapid indication of whether a given receptor is activated.

Reporter genes such as luciferase, CAT, GFP, β-lactamase or β-galactosidase are well known in the art, as are assays for the detection of their products.

Genes particularly well suited for monitoring receptor activity are the "immediate early" genes, which are rapidly induced, generally within minutes of contact between the receptor and the effector protein or ligand. The induction of immediate early gene transcription does not require the synthesis of new regulatory proteins. In addition to rapid responsiveness to ligand binding, characteristics of preferred genes useful for making reporter constructs include: low or undetectable expression in quiescent cells; induction that is transient and independent of new protein synthesis; subsequent shut-off of transcription requires new protein synthesis; and mRNAs transcribed from these genes have a short half-life. It is preferred, but not necessary that a transcriptional control element have all of these properties for it to be useful.

An example of a gene that is responsive to a number of different stimuli is the c-fos proto-oncogene. The c-fos gene is activated in a protein-synthesis-independent manner by growth factors, hormones, differentiation-specific agents, stress, and other known inducers of cell surface proteins. The induction of c-fos expression is extremely rapid, often occurring within minutes of receptor stimulation. This characteristic makes the c-fos regulatory regions particularly attractive for use as a reporter of receptor activation.

The c-fos regulatory elements include (see, Verma et al., 1987, Cell 51: 513-514): a TATA box that is required for transcription initiation; two upstream elements for basal transcription, and an enhancer, which includes an element with dyad symmetry and which is required for induction by TPA, serum, EGF, and PMA.

The 20 bp c-fos transcriptional enhancer element located between −317 and −298 bp upstream from the c-fos mRNA cap site, is essential for serum induction in serum starved NIH 3T3 cells. One of the two upstream elements is located at −63 to −57 and it resembles the consensus sequence for cAMP regulation.

The transcription factor CREB (cyclic AMP responsive element binding protein) is, as the name implies, responsive to levels of intracellular cAMP. Therefore, the activation of a receptor that signals via modulation of cAMP levels can be monitored by detecting either the binding of the transcription factor, or the expression of a reporter gene linked to a CREB-binding element (termed the CRE, or cAMP response element). The DNA sequence of the CRE is TGACGTCA (SEQ ID NO: 7). Reporter constructs responsive to CREB binding activity are described in U.S. Pat. No. 5,919,649.

Other promoters and transcriptional control elements, in addition to the c-fos elements and CREB-responsive constructs, include the vasoactive intestinal peptide (VIP) gene promoter (cAMP responsive; Fink et al., 1988, Proc. Natl. Acad. Sci. 85:6662-6666); the somatostatin gene promoter (cAMP responsive; Montminy et al., 1986, Proc. Natl. Acad. Sci. 8.3:6682-6686); the proenkephalin promoter (responsive to cAMP, nicotinic agonists, and phorbol esters; Comb et al., 1986, Nature 323:353-356); the phosphoenolpyruvate carboxy-kinase (PEPCK) gene promoter (cAMP responsive; Short et al., 1986, J. Biol. Chem. 261:9721-9726).

Additional examples of transcriptional control elements that are responsive to changes in GPCR activity include, but are not limited to those responsive to the AP-1 transcription factor and those responsive to NF-κB activity. The consensus AP-1 binding site is the palindrome TGA(C/G)TCA (Lee et al., 1987, Nature 325: 368-372; Lee et al., 1987, Cell 49: 741-752). The AP-1 site is also responsible for mediating induction by tumor promoters such as the phorbol ester 12-O-tetradecanoylphorbol-beta-acetate (TPA), and are therefore sometimes also referred to as a TRE, for TPA-response element. AP-1 activates numerous genes that are involved in the early response of cells to growth stimuli. Examples of AP-1-responsive genes include, but are not limited to the genes for Fos and Jun (which proteins themselves make up AP-1 activity), Fos-related antigens (Fra) 1 and 2, IκBα, ornithine decarboxylase, and annexins I and II.

The NF-κB binding element has the consensus sequence GGGGACTTTCC (SEQ ID NO: 8). A large number of genes have been identified as NF-κB responsive, and their control elements can be linked to a reporter gene to monitor GPCR activity. A small sample of the genes responsive to NF-κB includes those encoding IL-1β (Hiscott et al., 1993, Mol. Cell. Biol. 13: 6231-6240), TNF-α (Shakhov et al., 1990, J. Exp. Med. 171: 35-47), CCR5 (Liu et al., 1998, AIDS Res. Hum. Retroviruses 14: 1509-1519), P-selection (Pan & McEver, 1995, J. Biol. Chem. 270: 23077-23083), Fas ligand (Matsui et al., 1998, J. Immunol. 161: 3469-3473), GM-CSF (Schreck & Baeuerle, 1990, Mol. Cell. Biol. 10: 1281-1286) and IκBα (Haskill et al., 1991, Cell 65: 1281-1289). Each of these references is incorporated herein by reference. Vectors encoding NF-κB-responsive reporters are also known in the art or can be readily made by one of skill in the art using, for example, synthetic NF-κB elements and a minimal promoter, or using the NF-κB-responsive sequences of a gene known to be subject to NF-κB regulation. Further, NF-κB responsive reporter constructs are commercially available from, for example, CLONTECH.

A given promoter construct should be tested by exposing GPR72 polypeptide-expressing cells, transfected with the construct, to PUFAs. An increase of at least two-fold in the expression of reporter in response to PUFAs indicates that the reporter is an indicator of GPR72 polypeptide activity.

In order to assay GPR72 polypeptide activity with a transcriptional reporter construct, cells that stably express a GPR72 polypeptide are stably transfected with the reporter construct. To screen for agonists, the cells are left untreated, exposed to candidate modulators, or exposed to PUFAs, and expression of the reporter is measured. The PUFAs-treated cultures serve as a standard for the level of transcription induced by a known agonist. An increase of at least 50% in reporter expression in the presence of a candidate modulator indicates that the candidate is a modulator of GPR72 polypeptide activity. An agonist will induce at least as much, and preferably the same amount or greater reporter expression than PUFAs alone. This approach can also be used to screen for inverse agonists where cells express a GPR72 polypeptide at levels such that there is an elevated basal activity of the reporter in the absence of PUFAs or another agonist. A decrease in reporter activity of 10% or more in the presence of a candidate modulator, relative to its absence, indicates that the compound is an inverse agonist.

To screen for antagonists, the cells expressing GPR72 polypeptide and carrying the reporter construct are exposed to PUFAs (or another agonist) in the presence and absence of candidate modulator. A decrease of 10% or more in reporter expression in the presence of candidate modulator, relative to the absence of the candidate modulator, indicates that the candidate is a modulator of GPR72 polypeptide activity.

Controls for transcription assays include cells not expressing GPR72 polypeptide but carrying the reporter construct, as well as cells with a promoterless reporter construct. Compounds that are identified as modulators of GPR72 polypeptide-regulated transcription should also be analyzed to determine whether they affect transcription driven by other regulatory sequences and by other receptors, in order to determine the specificity and spectrum of their activity.

The transcriptional reporter assay, and most cell-based assays, are well suited for screening expression libraries for proteins for those that modulate GPR72 polypeptide activity. The libraries can be, for example, cDNA libraries from natural sources, e.g., plants, animals, bacteria, etc., or they can be libraries expressing randomly or systematically mutated variants of one or more polypeptides. Genomic libraries in viral vectors can also be used to express the mRNA content of one cell or tissue in the different libraries used for screening of GPR72 polypeptide.

h) Inositol Phosphates (IP) Measurement

Cells of the invention, for example, CHO-K1 cells, are labelled for 24 hours with 10 μCi/ml [$^3$H] inositol in inositol free DMEM containing 5% FCS, antibiotics, amphotericin, sodium pyruvate and 400 μg/ml G418. Cells are incubated for 2 h in Krebs-Ringer Hepes (KRH) buffer of the following composition (124 mM NaCl, 5 mM KCl, 1.25 mM $MgSO_4$, 1.45 mM $CaCl_2$, 1.25 mM $KH_2PO_4$, 25 mM Hepes (pH:7.4) and 8 mM glucose). The cells are then challenged with PUFAs for 30 min. The incubation is stopped by the addition of an ice cold 3% perchloric acid solution. IP are extracted and separated on Dowex columns as previously described (25).

GPR72 Polypeptide Assay

The invention provides for an assay for detecting the activity of a receptor of the invention in a sample. For example, GPR72 polypeptide activity can be measured in a sample comprising a cell or a cell membrane that expresses GPR72 polypeptide. As above, PUFA is used as an example in this section. It should be understood that AA-PUFA as defined herein can be used in these assays. The assay is performed by incubating the sample in the presence or absence of PUFA and carrying out a second messenger assay, as described above. The results of the second messenger assay performed in the presence or absence of PUFA are compared to determine if the GPR72 polypeptide receptor is active. An increase of 10% or more in the detected level of a given second messenger, as defined herein, in the presence of PUFA relative to the amount detected in an assay performed in the absence of PUFA is indicative of GPR72 polypeptide activity.

Any of the assays of receptor activity, including but not limited to the GTP-binding, GTPase, adenylate cyclase, cAMP, phospholipid-breakdown, diacylglycerol, inositol trisphosphate, arachidonic acid release (see below), PKC, kinase and transcriptional reporter assays, can be used to determine the presence of an agent in a sample, e.g., a tissue sample, that affects the activity of the GPR72 polypeptide receptor molecule. To do so, GPR72 polypeptide is assayed for activity in the presence and absence of the sample or an extract of the sample. An increase in GPR72 polypeptide activity in the presence of the sample or extract relative to the absence of the sample indicates that the sample contains an agonist of the receptor activity. A decrease in receptor activity in the presence of PUFA or another agonist and the sample, relative to receptor activity in the presence of PUFA alone, indicates that the sample contains an antagonist of GPR72 polypeptide activity. If desired, samples can then be fractionated and further tested to isolate or purify the agonist or antagonist. The amount of increase or decrease in measured activity necessary for a sample to be said to contain a modulator depends upon the type of assay used. Generally, a 10% or greater change (increase or decrease) relative to an assay performed in the absence of a sample indicates the presence of a modulator in the sample. One exception is the transcriptional reporter assay, in which at least a two-fold increase or 10% decrease in signal is necessary for a sample to be said to contain a modulator. It is preferred that an agonist stimulates at least 50%, and preferably 75% or 100% or more, e.g., 2-fold, 5-fold, 10-fold or greater receptor activation than with PUFA alone.

Other functional assays include, for example, microphysiometer or biosensor assays, for example, assays which consist in a real-time monitoring of morphological changes in living cells by electronic cell sensor arrays. Such an assay is a noninvasive and label-free assay for GPCRs that can be used with both engineered and nonengineered cell lines. It is based on using cell-electrode impedance to measure minute changes in cellular morphology as a result of ligand-dependent GPCR activation. Contributors to the impedance measurements are changes in cell adherence to their substrate, changes in cell shape and volume, and changes in cell-cell interactions. These will affect the flow of extracellular and transcellular current and hence the magnitude and characteristics of the signal measured. Each of these physiological changes can be linked to receptor stimulation through classical signaling pathways that result, for example, in changes in cytoskeletal organization.

Other functional assays include, for example, microphysiometer or biosensor assays (see Hafner, 2000, Biosens. Bioelectron. 15: 149-158, incorporated herein by reference). The intracellular level of arachidonic acid can also be determined as described in Gijon et al., 2000, J. Biol. Chem., 275:20146-20156.

II. Diagnostic Assays Based Upon the Interaction of GPR72 Polypeptide and PUFA:

Signalling through GPCRs is instrumental in the pathology of a large number of diseases and disorders. GPR72 polypeptide, which is expressed in cells of the Central Nervous System, as well as in lymphocytes and thymus, can have a role in CNS and immune processes, as well as in all associated disorders or diseases.

The expression pattern of GPR72 polypeptide and the knowledge with respect to disorders generally mediated by GPCRs suggests that GPR72 polypeptide can be involved in disturbances of migraine, vomiting, psychotic and neurological disorders, including anxiety, schizophrenia, manic depression, depression, delirium, dementia and severe mental retardation, degenerative diseases, neurodegenerative diseases such as Alzheimer's disease or Parkinson's disease, Hyperactivity disorders like attention deficit-hyperactivity disorder (ADHA), dyslexia, depression, senile dementia, bipolar disorders like alcoholism and schizotypy and dyskinasias, such as Huntington's disease or Gilles de la Tourett's syndrome and other related diseases including thrombosis and other cardiovascular diseases, autoimmune and inflammatory diseases such as psoriasis, Eczeme, inflammatory and trophic diseases of skin, rheumatoid arthritis, scleroderma, lupus, polymyositis, dermatomysitis, Crohn's disease, inflammatory bowel disease (IBD), Irritable Bowel Syndrome, Ulcerative Colitis, Asthma, Chronic Obstructive Pulmonary Disease, Allergic Rhinitis, Fibromyalgia, Organ Transplant Rejection, Graft versus host disease, Multiple Sclerosis, Acute, Ischemic Stroke, Infectious diseases, Hepatitis A, Hepatitis B, Hepatitis C, Sepsis, Septic shock, Chronic bronchitis, infections such as bacterial, fungal, protozoan and viral infections, such as infections caused by HIV1 and HIV2, and pain, anorexia, bulimia, asthma, acute heart failure, hypertension, urinary retention, osteoporosis, angina pectoris, myocardial infarction, ulcers, allergies, benign prostatic hypertrophy, and Type 1 Diabetes, Type 2 Diabetes, Osteoarthritis, Diabetic Retinopathy, Diabetic Nephropathy and fertility dysfunctions, foetal developmental disorders, cell migration, cancer, development of tumours and tumour metastasis, inflammatory and neoplastic processes, wound and bone healing and dysfunction of regulatory growth functions, obesity, anorexia, bulimia, acute heart failure, hypotension, hypertension, urinary retention, osteoporosis, angina pectoris, restenosis, atherosclerosis, thrombosis and other cardiovascular diseases, autoimmune and, diseases characterized by excessive smooth muscle cell proliferation, aneurysms, diseases characterized by loss of smooth muscle cells or reduced smooth muscle cell proliferation, stroke, ischemia, ulcers, allergies and prostatic hypertrophy.

The interaction of GPR72 polypeptide with PUFA can be used as the basis of assays for the diagnosis or monitoring of diseases, disorders or processes involving GPR72 polypeptide signalling. Diagnostic assays for GPR72 polypeptide-related diseases or disorders can have several different forms. First, diagnostic assays can measure the amount of GPR72 polypeptides, mRNA or ligand in a sample of tissue. Assays that measure the amount of mRNA encoding GPR72 polypeptide also fit into this category. Second, assays can evaluate the qualities of the receptor or the ligand. For example, assays that determine whether an individual expresses a mutant or variant form of GPR72 polypeptide can be used diagnostically. Third, assays that measure one or more activities of GPR72 polypeptide can be used diagnostically.

A. Assays that Measure the Amount of GPR72 Polypeptide

GPR72 polypeptide levels can be measured and compared to standards in order to determine whether an abnormal level of the receptor or its ligand is present in a sample, either of which indicate probable dysregulation of GPR72 polypeptide signalling. Polypeptide levels are measured, for example, by immunohistochemistry using antibodies specific for the polypeptide. A sample isolated from an individual suspected of suffering from a disease or disorder characterized by GPR72 polypeptide activity is contacted with an antibody for a GPR72 polypeptide, and binding of the antibody is measured as known in the art (e.g., by measurement of the activity of an enzyme conjugated to a secondary antibody).

Another approach to the measurement of GPR72 polypeptide levels uses flow cytometry analysis of cells from an affected tissue. Methods of flow cytometry, including the fluorescent labeling of antibodies specific for GPR72 polypeptide, are well known in the art. Other approaches include radioimmunoassay or ELISA. Methods for each of these are also well known in the art.

The amount of binding detected is compared to the binding in a sample of similar tissue from a healthy individual, or from a site on the affected individual that is not so affected. An increase of 10% or more relative to the standard is diagnostic for a disease or disorder characterized by GPR72 polypeptide dysregulation.

GPR72 polypeptide expression can also be measured by determining the amount of mRNA encoding the polypeptides in a sample of tissue. Levels of mRNA can be measured by quantitative or semi-quantitative PCR. Methods of "quantitative" amplification are well known to those of skill in the art, and primer sequences for the amplification of GPR72 nucleic acid are disclosed herein. A common method of quantitative PCR involves simultaneously co-amplifying a known quantity of a control sequence using the same primers. This provides an internal standard that can be used to calibrate the PCR reaction. Detailed protocols for quantitative PCR are provided in *PCR Protocols, A Guide to Methods and Applications*, Innis et al., Academic Press, Inc. N.Y., (1990), which is incorporated herein by reference. An increase of 10% or more in the amount of mRNA encoding GPR72 polypeptide in a sample, relative to the amount expressed in a sample of like tissue from a healthy individual or in a sample of tissue from an unaffected location in an affected individual is diagnostic for a disease or disorder characterized by dysregulation of GPR72 polypeptide signalling.

B. Qualitative Assays

Assays that evaluate whether or not a GPR72 polypeptide or the mRNA encoding it are wild-type or not can be used diagnostically. In order to diagnose a disease or disorder characterized by GPR72 polypeptide dysregulation in this manner, RNA isolated from a sample is used as a template for PCR amplification of GPR72 polypeptide. The amplified sequences are then either directly sequenced using standard methods, or are first cloned into a vector, followed by sequencing. A difference in the sequence that changes one or more encoded amino acids relative to the sequence of wild-type GPR72 polypeptide can be diagnostic of a disease or disorder characterized by dysregulation of GPR72 polypeptide signalling. It can be useful, when a change in coding sequence is identified in a sample, to express the variant receptor or ligand and compare its activity to that of wild type GPR72 polypeptide. Among other benefits, this approach can provide novel mutants, including constitutively active and null mutants.

In addition to standard sequencing methods, amplified sequences can be assayed for the presence of specific mutations using, for example, hybridization of molecular beacons that discriminate between wild type and variant sequences. Hybridization assays that discriminate on the basis of changes as small as one nucleotide are well known in the art. Alternatively, any of a number of "minisequencing" assays can be performed, including, those described, for example, in U.S. Pat. Nos. 5,888,819, 6,004,744 and 6,013,431 (incorporated herein by reference). These assays and others known in the art can determine the presence, in a given sample, of a nucleic acid with a known polymorphism.

If desired, array or microarray-based methods can be used to analyze the expression or the presence of mutation, in GPR72 polypeptide sequences. Array-based methods for minisequencing and for quantitation of nucleic acid expression are well known in the art.

C. Functional Assays.

Diagnosis of a disease or disorder characterized by the dysregulation of GPR72 polypeptide signalling can also be performed using functional assays. To do so, cell membranes or cell extracts prepared from a tissue sample are used in an assay of GPR72 polypeptide activity as described herein (e.g., ligand binding assays, the GTP-binding assay, GTPase assay, adenylate cyclase assay, cAMP assay, arachidonic acid level, phospholipid breakdown, diacyl glycerol or inositol trisphosphate assays, PKC activation assay, or kinase assay). The activity detected is compared to that in a standard sample taken from a healthy individual or from an unaffected site on the affected individual. As an alternative, a sample or extract of a sample can be applied to cells expressing GPR72 polypeptide, followed by measurement of GPR72 polypeptide signalling activity relative to a standard sample. A difference of 10% or more in the activity measured in any of these assays, relative to the activity of the standard, is diagnostic for a disease or disorder characterized by dysregulation of GPR72 polypeptide signalling.

Modulation of GPR72 Polypeptide Activity in a Cell According to the Invention

The discovery of PUFA as a ligand of GPR72 polypeptide provides methods of modulating the activity of a GPR72 polypeptide in a cell. GPR72 polypeptide activity is modulated in a cell by delivering to that cell an agent that modulates the function of a GPR72 polypeptide. This modulation can be performed in cultured cells as part of an assay for the identification of additional modulating agents, or, for example, in an animal, including a human. Agents include PUFA and other ligands as defined herein, as well as additional modulators identified using the screening methods described herein including but not limited to any of the PUFA analogues.

An agent can be delivered to a cell by adding it to culture medium. The amount to deliver will vary with the identity of the agent and with the purpose for which it is delivered. For example, in a culture assay to identify antagonists of GPR72 polypeptide activity, one will preferably add an amount of agent, e.g., PUFA that half-maximally activates the receptors (e.g., approximately $EC_{50}$), preferably without exceeding the dose required for receptor saturation. This dose can be determined by titrating the amount of PUFA to determine the point at which further addition of PUFA has no additional effect on GPR72 polypeptide activity.

When a modulator of GPR72 polypeptide activity is administered to an animal for the treatment of a disease or disorder, the amount administered can be adjusted by one of skill in the art on the basis of the desired outcome. Successful treatment is achieved when one or more measurable aspects of the pathology (e.g., tumor cell growth, accumulation of inflammatory cells) is changed by at least 10% relative to the value for that aspect prior to treatment.

Candidate Modulators Useful According to the Invention

The invention provides for a compound that is a modulator of a receptor of the invention.

Preferably a candidate modulator is a PUFA or AA-PUFA as defined herein above, a ligand as defined herein above or an agent identified according to the invention.

The candidate compound can be a synthetic compound, or a mixture of compounds, or may be a natural product (e.g. a plant extract or culture supernatant). A candidate compound according to the invention includes but is not limited to a small molecule that can be synthesized, a natural extract, peptides, polypeptides, carbohydrates, lipids, an antibody or antigen-binding fragment thereof, nucleic acids, and a small organic molecules.

Candidate modulator compounds from large libraries of synthetic or natural compounds can be screened. Numerous means are currently used for random and directed synthesis of saccharide, peptide, and nucleic acid based compounds. Synthetic compound libraries are commercially available from a number of companies including Maybridge Chemical Co.

(Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wis.). Combinatorial libraries are available and can be prepared. Alternatively, libraries of natural compounds in the form of bacterial, fungal, plant and animal extracts are available from e.g., Pan Laboratories (Bothell, Wash.) or MycoSearch (NC), or are readily producible by methods well known in the art. Additionally, natural and synthetically produced libraries and compounds are readily modified through conventional chemical, physical, and biochemical means.

Useful compounds may be found within numerous chemical classes. Useful compounds may be organic compounds, or small organic compounds. Small organic compounds have a molecular weight of more than 50 yet less than about 2,500 daltons, preferably less than about 750, more preferably less than about 350 daltons. Exemplary classes include heterocycles, peptides, saccharides, steroids, and the like. The compounds may be modified to enhance efficacy, stability, pharmaceutical compatibility, and the like. Structural identification of an agent may be used to identify, generate, or screen additional agents. For example, where peptide agents are identified, they may be modified in a variety of ways to enhance their stability, such as using an unnatural amino acid, such as a D-amino acid, particularly D-alanine, by functionalizing the amino or carboxylic terminus, e.g. for the amino group, acylation or alkylation, and for the carboxyl group, esterification or amidification, or the like.

For primary screening, a useful concentration of a candidate compound according to the invention is from about 100 nM to about 100 µM or more, (but can also be 1 nM and higher, 1 pM and higher, or 1 fM and higher). The primary screening concentration will be used as an upper limit, along with nine additional concentrations, wherein the additional concentrations are determined by reducing the primary screening concentration at half-log intervals (e.g. for 9 more concentrations) for secondary screens or for generating concentration curves.

Antibodies Useful According to the Invention

The invention provides for antibodies to GPR72 polypeptide. Antibodies can be made using standard protocols known in the art (See, for example, Antibodies: A Laboratory Manual ed. by Harlow and Lane (Cold Spring Harbor Press: 1988)). A mammal, such as a mouse, hamster, or rabbit can be immunized with an immunogenic form of the peptide (e.g., GPR72 polypeptide or an antigenic fragment which is capable of eliciting an antibody response, or a fusion protein as described herein above). Immunogens for raising antibodies are prepared by mixing the polypeptides (e.g., isolated recombinant polypeptides or synthetic peptides) with adjuvants. Alternatively, GPR72 polypeptides or peptides are made as fusion proteins to larger immunogenic proteins. Polypeptides can also be covalently linked to other larger immunogenic proteins, such as keyhole limpet hemocyanin. Alternatively, plasmid or viral vectors encoding GPR72 polypeptide, or a fragment of these proteins, can be used to express the polypeptides and generate an immune response in an animal as described in Costagliola et al., 2000, J. Clin. Invest. 105:803-811, which is incorporated herein by reference. In order to raise antibodies, immunogens are typically administered intradermally, subcutaneously, or intramuscularly to experimental animals such as rabbits, sheep, and mice. In addition to the antibodies discussed above, genetically engineered antibody derivatives can be made, such as single chain antibodies.

The progress of immunization can be monitored by detection of antibody titers in plasma or serum. Standard ELISA, flow cytometry or other immunoassays can also be used with the immunogen as antigen to assess the levels of antibodies. Antibody preparations can be simply serum from an immunized animal, or if desired, polyclonal antibodies can be isolated from the serum by, for example, affinity chromatography using immobilized immunogen.

To produce monoclonal antibodies, antibody-producing splenocytes can be harvested from an immunized animal and fused by standard somatic cell fusion procedures with immortalizing cells such as myeloma cells to yield hybridoma cells. Such techniques are well known in the art, and include, for example, the hybridoma technique (originally developed by Kohler and Milstein, (1975) Nature, 256: 495-497), the human B cell hybridoma technique (Kozbar et al., (1983) Immunology Today, 4: 72), and the EBV-hybridoma technique to produce human monoclonal antibodies (Cole et al., (1985) Monoclonal Antibodies and Cancer Therapy, Alan R. Liss, Inc. pp. 77-96). Hybridoma cells can be screened immunochemically for production of antibodies specifically reactive with GPR72 polypeptide, and monoclonal antibodies isolated from the media of a culture comprising such hybridoma cells.

In addition, a functional fragment of an antibody, including fragment of chimeric, humanized, primatized or single chain antibody, can also be produced. Functional fragments of the foregoing antibodies retain at least one binding function and/or modulation function of the full-length antibody from which they are derived. Preferred functional fragments retain an antigen-binding function of a corresponding full-length antibody (e.g., retain the ability to bind a human GPR72). Particularly preferred functional fragments retain the ability to inhibit or activate one or more functions characteristic of a GPR72, such as a binding activity, a signaling activity, and/or stimulation of a cellular response. For example, in one embodiment, a functional fragment can inhibit or activate the interaction of GPR72 with one or more of its ligands, and/or can inhibit or activate one or more receptor-mediated functions.

For example, antibody fragments capable of binding to a human GPR72 receptor or portion thereof, including, but not limited to, scFv, Fv, Fab, Fab' and F(ab')$^2$ fragments are encompassed by the invention. Such fragments can be produced by enzymatic cleavage or by recombinant techniques, for example. For instance, papain or pepsin cleavage can generate Fab or F(ab')$^2$ fragments, respectively. Antibodies can also be produced in a variety of truncated forms using antibody genes in which one or more stop codons has been introduced upstream of the natural stop site. For example, a chimeric gene encoding a F(ab')$^2$ heavy chain portion can be designed to include DNA sequences encoding the CH1 domain and hinge region of the heavy chain.

Homologous sequences of an antibody sequence according to the invention may include an amino acid or nucleotide sequence encoding a similar sequence which exists in other animal species (rat, human, cat, dog, etc.) or in specific human population groups, but which are involved in the same biochemical pathway.

Such homologous sequences may comprise additions, deletions or substitutions of one or more amino acids or nucleotides, which do not substantially alter the functional characteristics of the antibody or fragment thereof according to the invention. That is, homologs will have at least 90% of the activity of an amino acid sequence of an antibody or fragment thereof and will bind, stimulate or inhibit GPR72 specifically.

Such homologous sequences can also be nucleotide sequences of more than 50, 100, 200, 300, 400, 600, 800 or 1000 nucleotides which are able to hybridize to the amino acid sequence of any antibody or fragment thereof under stringent hybridisation conditions (such as the ones described by SAMBROOK et al., Molecular Cloning, Laboratory Manuel, Cold Spring, Harbor Laboratory press, New York). An example of "stringent hybridization conditions" is as follows: hybridize in 50% formamide, 5×SSC, 50 mM sodium phosphate (pH 6.8), 0.1% sodium pyrophosphate, 5×Denhardt's solution, 50 μg/ml sonicated salmon sperm DNA, 0.1% SDS and 10% dextran sulfate at 42° C.; and wash at 42° C. (or higher, e.g., up to two degrees C. below the $T_m$ of the perfect complement of the probe sequence) in 0.2×SSC and 0.1% SDS.

High Throughput Screening Kit

A high throughput screening kit according to the invention comprises all the necessary means and media for performing the detection of a modulator compound including an agonist, antagonist, inverse agonist or inhibitor to the receptor of the invention in the presence or absence of PUFA, preferably at a concentration in the range of 100 nM to 100 μM. The kit comprises materials to perform the following successive steps. Recombinant cells of the invention, comprising and expressing the nucleotide sequence encoding the GPR72 polypeptide receptor, are grown on a solid support, such as a microtiter plate, more preferably a 96 well microtiter plate, according to methods well known to the person skilled in the art, especially as described in WO 00/02045. Modulator compounds according to the invention, preferably at a concentrations from about 100 nM to 100 μM or more, are added to the culture media of defined wells in the presence or absence of an appropriate concentration of PUFA (preferably in the range of 100 nM to 100 μM).

Kits according to the invention can also comprise materials necessary for second messenger assays amenable to high throughput screening analysis, including but not limited to the measurement of intracellular levels of cAMP, intracellular inositol phosphate, intracellular diacylglycerol concentrations, arachinoid acid concentration or MAP kinase or tyrosine kinase activity (as described above). For example, the GPR72 polypeptide activity, as measured in a cyclic AMP assay, is quantified by a radioimmunoassay as previously described (26). Results are compared to the baseline level of GPR72 polypeptide activity obtained from recombinant cells according to the invention in the presence of PUFA but in the absence of added modulator compound. Wells showing at least 2 fold, preferably 5 fold, more preferably 10 fold and most preferably a 100 fold or more increase or decrease in GPR72 polypeptide activity as compared to the level of activity in the absence of modulator, are selected for further analysis.

Other Kits Useful According to the Invention

The invention provides for kits useful for screening for modulators of GPR72 polypeptide activity, as well as kits useful for diagnosis of diseases or disorders characterized by dysregulation of GPR72 polypeptide signalling. Kits useful according to the invention can include an isolated GPR72 polypeptide (including a membrane- or cell-associated GPR72 polypeptide, e.g., on isolated membranes, cells expressing GPR72 polypeptide, or on an SPR chip). A kit can also comprise an antibody specific for GPR72 polypeptide. Alternatively, or in addition, a kit can contain cells transformed to express GPR72 polypeptide. In a further embodiment, a kit according to the invention can contain a polynucleotide encoding a GPR72 polypeptide. In a still further embodiment, a kit according to the invention may comprise the specific primers useful for amplification of GPR72 polypeptide as described below. All kits according to the invention will comprise the stated items or combinations of items and packaging materials therefor. Kits will also include instructions for use.

Transgenic Animals

Transgenic mice provide a useful tool for genetic and developmental biology studies and for the determination of the function of a novel sequence. According to the method of conventional transgenesis, additional copies of normal or modified genes are injected into the male pronucleus of the zygote and become integrated into the genomic DNA of the recipient mouse. The transgene is transmitted in a Mendelian manner in established transgenic strains. Constructs useful for creating transgenic animals comprise genes under the control of either their normal promoters or an inducible promoter, reporter genes under the control of promoters to be analyzed with respect to their patterns of tissue expression and regulation, and constructs containing dominant mutations, mutant promoters, and artificial fusion genes to be studied with regard to their specific developmental outcome. Typically, DNA fragments on the order of 10 kilobases or less are used to construct a transgenic animal (Reeves, 1998, New. Anat., 253:19). Transgenic animals can be created with a construct comprising a candidate gene containing one or more polymorphisms according to the invention. Alternatively, a transgenic animal expressing a candidate gene containing a single polymorphism can be crossed to a second transgenic animal expressing a candidate gene containing a different polymorphism and the combined effects of the two polymorphisms can be studied in the offspring animals.

Other Transgenic Animals

The invention provides for transgenic animals that include but are not limited to transgenic mice, rabbits, rats, pigs, sheep, horses, cows, goats, etc. A protocol for the production of a transgenic pig can be found in White and Yannoutsos, Current Topics in Complement Research: 64th Forum in Immunology, pp. 88-94; U.S. Pat. No. 5,523,226; U.S. Pat. No. 5,573,933: PCT Application WO93/25071; and PCT Application WO95/04744. A protocol for the production of a transgenic mouse can be found in U.S. Pat. No. 5,530,177. A protocol for the production of a transgenic rat can be found in Bader and Ganten, Clinical and Experimental Pharmacology and Physiology, Supp. 3:S81-S87, 1996. A protocol for the production of a transgenic cow can be found in Transgenic Animal Technology, A Handbook, 1994, ed., Carl A. Pinkert, Academic Press, Inc. A protocol for the production of a transgenic rabbit can be found in Hammer et al., Nature 315:680-683, 1985 and Taylor and Fan, Frontiers in Bioscience 2:d298-308, 1997.

Knock Out Animals i. Standard

Knock out animals are produced by the method of creating gene deletions with homologous recombination. This technique is based on the development of embryonic stem (ES) cells that are derived from embryos, are maintained in culture and have the capacity to participate in the development of every tissue in the mouse when introduced into a host blastocyst. A knock out animal is produced by directing homologous recombination to a specific target gene in the ES cells, thereby producing a null allele of the gene. The potential phenotypic consequences of this null allele (either in heterozygous or homozygous offspring) can be analyzed (Reeves, supra).

ii. In vivo Tissue Specific Knock Out in Mice Using Cre-lox.

The method of targeted homologous recombination has been improved by the development of a system for site-specific recombination based on the bacteriophage P1 site specific recombinase Cre. The Cre-loxP site-specific DNA recombinase from bacteriophage P1 is used in transgenic mouse assays in order to create gene knockouts restricted to defined tissues or developmental stages. Regionally restricted genetic deletion, as opposed to global gene knockout, has the advantage that a phenotype can be attributed to a particular cell/tissue (Marth, 1996, *Clin. Invest.* 97: 1999). In the Cre-loxP system one transgenic mouse strain is engineered such that loxP sites flank one or more exons of the gene of interest. Homozygotes for this so called 'floxed gene' are crossed with a second transgenic mouse that expresses the Cre gene under control of a cell/tissue type transcriptional promoter. Cre protein then excises DNA between loxP recognition sequences and effectively removes target gene function (Sauer, 1998, *Methods,* 14:381). There are now many in vivo examples of this method, including the inducible inactivation of mammary tissue specific genes (Wagner et al., 1997, *Nucleic Acids Res.,* 25:4323).

iii. Bac Rescue of Knock Out Phenotype

In order to verify that a particular genetic polymorphism/mutation is responsible for altered protein function in vivo one can "rescue" the altered protein function by introducing a wild-type copy of the gene in question. In vivo complementation with bacterial artificial chromosome (BAC) clones expressed in transgenic mice can be used for these purposes. This method has been used for the identification of the mouse circadian Clock gene (Antoch et al., 1997, *Cell* 89: 655).

Materials

Trypsin was from Flow Laboratories (Bioggio, Switzerland). Culture media, G418, fetal bovine serum (FBS), restriction enzymes, Pfu DNA Polymerase was purchased from Stratagene and Taq DNA polymerases were purchased from Eurogentec. (Liege, Belgium). The radioactive product myo-D-[2$^3$H]inositol (17.7 Ci/mmol) was from Amersham (Ghent, Belgium). Dowex AG1X8 (formate form) was from Bio-Rad Laboratories (Richmond, Calif.). ATP was obtained from Sigma Chemical Co. (St. Louis, Mo.). Forskolin was purchased from Calbiochem (Bierges, Belgium). Rolipram was a gift from the Laboratories Jacques Logeais (Trappes, France).

Dosage and Mode of Administration

By way of example, a patient can be treated as follows by the administration of a modulator of GPR72 polypeptide (for example, an agonist, antagonist or inhibitor of GPR72 polypeptide, of the invention). A modulator of GPR72 polypeptide of the invention can be administered to the patient, preferably in a biologically compatible solution or a pharmaceutically acceptable delivery vehicle, by ingestion, injection, inhalation or any number of other methods. The dosages administered will vary from patient to patient; a "therapeutically effective dose" can be determined, for example, by the level of enhancement of function (e.g., as determined in a second messenger assay described herein). Monitoring PUFA binding will also enable one skilled in the art to select and adjust the dosages administered. The dosage of a modulator of GPR72 polypeptide of the invention may be repeated daily, weekly, monthly, yearly, or as considered appropriate by the treating physician.

In one embodiment, a patient can be treated to modulate the signalling activity of a GPR72 polypeptide receptor by administering to a patient a sublethal dose of an agent which inhibits or promotes the signalling activity of GPR72 polypeptide. A sublethal dose according to the invention, refers to a dose of an agent for inhibiting or stimulating a GPR72 polypeptide signalling activity which is at or below the LD50 for the particular agent. In one embodiment, the dose of an agent which inhibits the signalling activity of GPR72 polypeptide is between 1 fM and 1 M, preferably between 1 pM and 1 mM, preferably between 1 nM and 1 μM and more preferably between 100 nM and 100 μM. In one embodiment, an agent useful for the modulation of GPR72 polypeptide signalling may be an antibody which specifically binds to the ligand binding site of GPR72 polypeptide. An amount of anti-GPR72 polypeptide antibody needed to achieve a dosage useful for the modulation of GPR72 polypeptide signalling will depend upon the level of expression of GPR72 polypeptide, localization of receptor expression, and general state of the patient's own immune system, but generally range from 0.0005 to 5.0 mg of anti-GPR72 polypeptide antibody or binding protein thereof per kilogram of body weight, with doses of 0.05 to 2.0 mg/kg/dose being more commonly used.

Pharmaceutical Compositions

The invention provides for compositions comprising a GPR72 polypeptide modulator according to the invention admixed with a physiologically compatible carrier. As used herein, "physiologically compatible carrier" refers to a physiologically acceptable diluent such as water, phosphate buffered saline, or saline, and further may include an adjuvant. Adjuvants such as incomplete Freund's adjuvant, aluminium phosphate, aluminium hydroxide, or alum are materials well known in the art.

The invention also provides for pharmaceutical compositions. In addition to the active ingredients, these pharmaceutical compositions may contain suitable pharmaceutically acceptable carrier preparations which can be used pharmaceutically.

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, or other plants; cellulose such as methyl cellulose, hydroxypropylmethyl-cellulose, or sodium carboxymethyl cellulose; and gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating such as glycerol or sorbitol. Push-fit capsules can contain active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Pharmaceutical formulations for parenteral administration include aqueous solutions of active compounds. For injection, the pharmaceutical compositions of the invention may be formulated in aqueous solutions, preferably in physiologically compatible buffers such as Hank's solution, Ringer' solution, or physiologically buffered saline. Aqueous injection suspensions may contain substances which increase the viscosity of the suspension, such as sodium carboxymethyl cellulose, sorbitol, or dextran. Additionally, suspensions of the active solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For nasal administration, penetrants appropriate to the particular barrier to be permeated are used in the formulation. Such penetrants are generally known in the art.

The pharmaceutical compositions of the present invention may be manufactured in a manner known in the art, e.g. by means of conventional mixing, dissolving, granulating, dragee-making, levitating, emulsifying, encapsulating, entrapping or lyophilizing processes.

The pharmaceutical composition may be provided as a salt and can be formed with many acids, including but not limited to hydrochloric, sulfuric, acetic, lactic, tartaric, malic, succinic, etc. . . . Salts tend to be more soluble in aqueous or other protonic solvents that are the corresponding free base forms. In other cases, the preferred preparation may be a lyophilized powder in 1 mM-50 mM histidine, 0.1%-2% sucrose, 2%-7% mannitol at a pH range of 4.5 to 5.5 that is combined with buffer prior to use.

After pharmaceutical compositions comprising a compound of the invention formulated in a acceptable carrier have been prepared, they can be placed in an appropriate container and labeled for treatment of an indicated condition with information including amount, frequency and method of administration.

EXAMPLES

Example 1

Cloning of Human and Mouse GPR72 Receptors

Specific oligonucleotide primers were synthesized on the basis of the sequence of the GPR72 human receptor: a sense primer 5'-ACCATGGTCCCTCACCTCTTG-3' (SEQ ID NO: 9) and an antisense primer 5'-CTAACTCATCGTCA-CAATG-3' (SEQ ID NO: 10). A polymerase chain reaction (PCR) was performed on Human Brain Marathon Ready cDNAs (Clontech). The amplification conditions for 25 cycles were as follows: 94° C. for 30 s; 55° C. for 60 s and 72° C. for 80 s followed by 7 min extension at 72° C. Amplifications resulted in a fragment of 1.3 kilobase containing the entire coding sequence of the GPR72 gene. The PCR product was then cloned using the pCR-BluntII-TOPO (Invitrogen). Coding sequence was then subcloned by enzymatic restriction between the SpeI and EcoRV of the pCR-BluntII-TOPO and then inserted into the pEFIN3 expression vector in the EcoRV-XbaI sites (FIG. 1A and FIG. 1B).

Specific oligonucleotide primers were synthesized on the basis of the sequence of the GPR72 mouse receptor: a sense primer 5'-CAGTGGCTGGACATGAAGGTTCCTC-3' (SEQ ID NO: 11) and an antisense primer 5'-CAGCTTTC-CCTAACTCATGGCCAC-3' (SEQ ID NO: 12). A polymerase chain reaction (PCR) was performed on Mouse Brain Marathon Ready cDNAs (Clontech). The amplification conditions for 25 cycles were as follows: 94° C. for 30 s; 61° C. for 60 s and 72° C. for 80 s followed by 7 min extension at 72° C. Amplifications resulted in a fragment of 1.3 kilobase containing the entire coding sequence of the GPR72 gene. The PCR product was then cloned using the pCR-BluntII-TOPO (Invitrogen). Coding sequence was then subcloned by enzymatic restriction between the SpeI and EcoRV of the pCR-BluntII-TOPO and then inserted into the pEFIN3 expression vector in the EcoRV-XbaI sites (FIG. 2A and FIG. 2B).

Example 2

Tissue Distribution of GPR72

Tissue distribution of human GPR72-Reverse transcription-polymerase chain reaction (RT-PCR) experiments were carried out using a panel of poly(A)+ RNA (pituitary gland, spinal cord, thymus, pancreas, small intestine, uterus, placenta, stomach, liver, lung, spleen, testis, brain, heart, kidney, skeletal muscle). Aldolase mRNA was chosen as standard and amplified in a separate reaction. The Aldolase primers were 5'-ggcaagggcatcctggctgc-3' (forward) (SEQ ID NO: 13) and 5'-taacgggccagaacattggc-3' (reverse) (SEQ ID NO: 14), with an expected product size of 443 bp. The GPR72 primers were 5'-cgcacttcttctcttggaac-3' (forward) (SEQ ID NO: 15) and 5'-catgtgctgttcacaaagcg-3' (reverse) (SEQ ID NO: 16), with an expected product size of 276 bp. Approximately 500 ng of Poly(A)+ RNA was reverse transcribed with Superscript II (Invitrogen) and used for PCR. PCR was performed using the TaqDNA polymerase under the following conditions: denaturation at 94° C. for 3 min, 34 cycles at 94° C. for 1 min, 58° C. for 2 min, and 72° C. for 3 min. Aliquots (10 µl) of the PCRs were analyzed by 1% agarose gel electrophoresis.

A strong band of expected size was detected in brain and spinal cord, and at lower levels in pituitary gland, thymus, small intestine, uterus, stomach, liver, spleen, testis, heart and kidney (FIG. 3).

Example 3

Purification of a Natural Ligand of GPR72 and Identification of Arachidonic Acid Arachidonic acid was isolated and identified from a methanol extract of porcine cortex using 4 successive HPLC steps. After each step, collected fractions were tested for specific activity on GPR72 using Aequorin assay. First, second and fourth step were performed on reversed phase C18 columns; elutions were performed using linear gradients of acetonitrile+0.02% formic acid. Third step was performed on a normal phase column; elution was performed using a linear gradient from 0.5% MTBE in heptane to MTBE-IPA (9:1) containing 0.02% acetic acid. Active fraction from the fourth step was subjected to electrospray mass spectrometry (ESI-MS) analysis using a triple quadrupole-mass spectrometer. Results indicated that the active molecule formula is $C_{20}H_{32}O_2$, which is the formula of arachidonic acid (FIG. 4). Spectrum of authentic (all-Z)-5,8,11,14-Eicosatetraenoic acid; 5,8,11,14-all-cis-eicosatetraenoic acid (arachidonic acid) was compared to the active fraction spectrum and results showed remarkable similarities leading to the conclusion that the active molecule is 5,8,11,14-all-cis-eicosatetraenoic acid also known as arachidonic acid.

Example 4

Functional Assay for GPR72

GPR72 expressing clones have been obtained by transfection of CHO-K1 cells to coexpressing mitochondrial apoaequorin and Galpha66, limiting dilution and selection by RT-PCR. Positive clones were used for biological extract library screening with porcine spleen extracts prepared as described above. A functional assay based on the luminescence of mitochondrial aequorin intracellular $Ca^{2+}$ release (Stables et al., 1997, Anal. Biochem. 252:115-126; incorporated herein by reference) was performed as described (Detheux et al., 2000, J. Exp. Med., 192 1501-1508; incorporated herein by reference). Briefly, cells were collected from plates in PBS containing 5 mM EDTA, pelleted and resuspended at $5\times10^6$ cells/ml in DMEM-F12 medium. Cells were incubated with 5 µM Coelenterazine H (Molecular Probes) for 4 hours at room temperature. Cells were then washed in DMEM-F12 medium and resuspended at a concentration of $0.5\times10^6$ cells/ml. Cells were then mixed with test agonist peptides or plates containing tissue extracts and the light emission was recorded for 30 sec using a Microlumat luminometer (Perkin Elmer). Results are expressed as Relative Light Units (RLU).

Example 5

Activation of GPR72 by Arachidonic Acid

After being identified from active porcine cortex fraction, ability of arachidonic acid to trigger intracellular calcium release was tested on CHO-K1 cell lines coexpressing the human or the mouse GPR72 receptor and apoaequorin. We have used the aequorin assay as previously described in Detheux et al. (2000) J exp Med. 192, 1501-1508. As shown in FIG. 5, arachidonic acid was able to activate specifically the human GPR72 at concentration around 5 micromolar. CHO-K1 cells transfected with the bicistronic plasmid that does not encode the human GPR72 were used as control cells (mock-transfected). Arachidonic acid was also able to activate specifically the mouse GPR72 at concentration around 5 micromolar (FIG. 6).

Example 6

Activities of PUFAs and AA-PUFAs on GPR72

PUFAs were tested on CHO-K1 cells stably expressing the human GPR72 for their ability to trigger intracellular calcium using aequorin. Obtained EC50 are in the 1-20 µM range (FIG. 7).

Example 7

Structure-activity Relationship (SAR) of Arachidonic Acid on GPR72 Activation

Structure-activity relationship (SAR) of arachidonic acid showed that, when considered with the inactivity of closely structurally-related compounds, the acidic moiety is required for activity on GPR72, this moiety being branched at the extremity of a carbon chain comprising at least 18 carbon atoms, linear or not. For example arachidonic acid is active while arachidonic acid methyl ester is not active. In addition modification of the acidic moiety from a carboxylic function to a sulfonic acid modulate the activity but does not abolish it (for example both N-arachidonoyl-L-taurine and N-arachidonoyl-glycine are active). Double bonds (unsaturations), ranging from 2 to 6, are necessary for activation of GPR72 as saturated fatty acids homologues ranging from C16 to C21 are inactive. When the alpha amino group of an amino acid forms an amide bond with the carboxylic acid of a PUFA, activity on GPR72 is conserved. Substitutions with other functions differently modulate the activity on the human GPR72 receptor (FIG. 8).

Example 8

Activities of Additional PUFAs on GPR72

Additional PUFAs, Octadeca-6Z,9Z,12Z,15Z-tetraenoic acid (Stearidonic acid), Eicosa-11Z,14Z,17Z-trienoic acid, Docosa-7Z,10Z,13Z,16Z-tetraenoic acid (Adrenic acid), Eicosa-5,8,11,14-tetraynoic acid, Eicosa-5,8,11-triynoic acid and 13-cis-Retinoic acid, were tested on CHO-K1 cells stably expressing the human GPR72 for their ability to trigger intracellular calcium using aequorin. Obtained EC50 are given in FIG. 9.

Example 9

Activities of Three Thiazolidinediones on GPR72

Three thiazolidinediones, Ciglitazone, MCC-555 and Troglitazone, were tested on CHO-K1 cells stably expressing the human GPR72 for their ability to trigger intracellular calcium using aequorin. Obtained EC50 are given in FIG. 10. FIG. 11 shows the aequorin calcium response of human GPR72 to Ciglitazone and MCC-555.

REFERENCES

1. Abbrachio, M. P. and Burnstock, G. (1994) Pharmacol. Ther. 64, 445-475.
2. Fredholm, B. B. et al. (1997) Trends Pharmacol. Sci. 18, 79-82.
3. Webb, T. E. et al. (1993) FEBS Lett. 324, 219-225.
4. Léon, C. et al. (1997) FEBS Lett. 403, 26-30.
5. Communi, D. et al. (1997) J. Biol. Chem. 272, 31969-31973.
6. Lustig, K. D. et al. (1993) Proc. Natl. Acad. Sci. U.S.A. 90, 5113-5117.
7. Parr, C. E. et al. (1994) Proc. Natl. Acad. Sci. U.S.A. 91, 3275-3279.
8. Bogdanov, Y. et al. (1997) J. Biol. Chem. 272, 12583-12590.
9. Boyer, J. L. et al. (2000) Mol. Pharmacol. 57, 805-810.
10. Webb, T. E. et al. (1996) Mol. Pharmacol. 50, 258-265.
11. Chang, K. et al. (1995) J. Biol. Chem. 270, 26152-26158.
12. Communi, D. et al. (1996) Biochem. Biophys. Res. Commun. 222, 303-308.
13. Nicholas, R. A. et al. (1996) Mol. Pharmacol. 50, 224-229.
14. Communi, D. et al. (1995) J. Biol. Chem. 270, 30849-30852.
15. Nguyen, T. et al. (1995) J. Biol. Chem. 270, 30845-30848.
16. Webb, T. E. et al. (1996) Biochem. Biophys. Res. Commun. 219, 105-110.

17. Akbar, G. K. M. et al. (1996) J. Biol. Chem. 271, 18363-18367.
18. Yokomizo, T. et al. (1997) Nature 387, 620-624.
19. Li, Q. et al. (1997) Biochem. Biophys. Res. Commun. 236, 455-460.
20. Janssens, R. et al. (1997) Biochem. Biophys. Res. Commun. 226, 106-112.
21. Zhang, F. L et al. (2001) J. Biol. Chem. 276 (11), 8608-8615.
22. Hollopeter, G. et al. (2001) Nature 409, 202-207.
23. Chambers, J. K. et al. (2000) J. Biol. Chem. 275 (15), 10767-10771.
24. Wittenberger, T. et al. (2001) J. Mol. Biol. 307, 799-813.
25. Communi, D. et al. (1995b). Circ. Res., 76, 191-198.
26. Brooker, G. et al. (1979) Adv. Cyclic Nucleotide Res. 10, 1-33.
27. Minamide, L. S. and Bamburg, J. R. (1990) Anal. Biochem. 190, 66-70.
28. Erb, L. et al. (1995) J. Biol. Chem. 270, 4185-4188.
29. Baltensperger, K. and Porzig, H. (1997) J. Biol. Chem. 272, 10151-10159.
30. Eason, M. G. et al. (1992) J. Biol. Chem. 267 (22), 15795-15801.
31. Chabre, O. et al. (1994) J. Biol. Chem. 269 (8), 5730-5734.
32. Boyer, J. L. et al. (1993) J. Pharmacol. Exp. Ther. 267, 1140-1146.
33. Simon, J. et al. (2001) Br. J. Pharmacol. 132, 173-182.
34. Gudermann et al. (1995) J. Mol. Med. 73, 51-63.
35. Lundquist F. (1960) Acta Physiol. Scand. 175, 97
36. Bergman E. (1990) Physiol. Rev. 70, 567-590
37. Cummings J. H., et al. (1987) Gut 28:1221-7
38. Mirzabekov et al. (2000) Nature Biotechnology 18, 649-654
39. Ernst, S., C. Lange, A. Wilbers, V. Goebeler, V. Gerke, and U. Rescher. 2004, J. Immunol. 172:7669-7676.
40. Christophe, T., A. Karlsson, C. Dugave, M. J. Rabiet, F. Boulay, and C. Dahlgren. 2001. J. Biol. Chem. 276: 21585-21593.
41. Yang, D., Q. Chen, B. Gertz, R. He, M. Phulsuksombati, R. D. Ye, and J. J. Oppenheim. 2002. J. Leukoc. Biol. 72:598-607.
42. Stables, J., A. Green, F. Marshall, N. Fraser, E. Knight, M. Sautel, G. Milligan, M. Lee, and S. Rees. 1997. Anal. Biochem. 252:115-126.
43. Gourlet, P., J. Rathe, P. De Neef, J. Cnudde, M. C. Vandermeers-Piret, M. Waelbroeck, and P. Robberecht. 1998. Eur. J. Pharmacol. 354:105-111.
44. Migeotte, I., J. D. Franssen, S. Goriely, F. Willems, and M. Parmentier. 2002. Eur. J. Immunol. 32:494-501.
45. Costagliola, S., P. Rodien, M. C. Many, M. Ludgate, and G. Vassart. 1998. J. Immunol. 160:1458-1465.
46. Kotani, M., M. Detheux, A. Vandenbogaerde, D. Communi, J. M. Vanderwinden, E. Le Poul, S. Brezillon, R. Tyldesley, N. Suarez-Huerta, F. Vandeput, C. Blanpain, S. N. Schiffmann, G. Vassart, and M. Parmentier. 2001. J. Biol. Chem. 276:34631-34636.
47. Taketani, S., Y. Adachi, H. Kohno, S. Ikehara, R. Tokunaga, and T. Ishii. 1998. J. Biol. Chem. 273:31388-31394.
48. Adams et al. Molecular Brain Research 117 (2003) 39-46
49. Brezillon et al. Brain research 921 (2001) 21-30
50. Broadhurst et al. Br J Nutr 79 (1998) 3-21
51. Buydens-Branchey et al. Psychiatry Res 120 (2003) 29-35
52. Cao et al. Life Sciences 78 (2005) 74-81
53. Christensen and Christensen Acta Psychiatr Scand 78 (1988) 586-591
54. Clandinin Lipids; 34 (1999) 131-137
55. De Moerlooze et al., Cell Genet. 90 (2000) 146-150
56. Green et al. J Lipid Res 46 (2005). 1093-6
57. Harrigan et al. Mol. Cell. Biol. 9 (1989) 3438-3446
58. Harrigan et al. Mol. Endocrinol. 5 (1991) 1331-1338
59. Hibbeln & Salem Am J Clin Nutr 62 (1995) 1-9
60. Hashimoto et al. J Nutr 135 (2005) 549-555
61. Horrobin et al. Schizophr Res 30 (1998) 193-208
62. Huang et al. JBC 276 (2001) 42639-42644
63. Kalmijn et al. Ann Neurol; 42 (1997):776-82
64. Kazushige et al. J. Neurochem 63 (1994) 727-736
65. Laborit et al. Chem Biol Interact 10 (1975) 309-312
66. Milman et al. PNAS 103 (2006) 2428-2433
67. Parker et al. Biochimica et Biophysica Acta, 1491 (2000) 369-375
68. Peet M I, et al. editors. (1999). Carnforth, UK: Marius Press.
69. Pesini et al. Molecular brain research 57 (1998) 281-300
70. Rosenberger et al. J. Neurochem 88 (2004) 1168-1178
74. Sah et al. Neuroscience 133 (2005) 281-292
75. Stevens et al. Physiol Behav 59 (1996) 915-20
76. Stevens et al. Am J Clin Nutr 62 (1995) 761-8
77. Stordy Dyslexia Rev 9 (1997) 1-3
78. Wang et al. The journal of neuroscience 21 (2001) 9027-9035

The invention claimed is:

1. A method of identifying an agent that binds to a GPR72 polypeptide comprising an amino acid sequence selected from the group consisting of SEQ ID NO: 2 and SEQ ID NO:4, wherein said GPR72 polypeptide is capable of binding to a polyunsaturated fatty acid (PUFA), said method comprising:
   (a) contacting said GPR72 polypeptide with said polyunsaturated fatty acid (PUFA) in the presence or absence of a candidate binding agent under conditions permitting binding of said PUFA to said GPR72 polypeptide;
   (b) permitting the PUFA to bind to the GPR72 polypeptide; and,
   (c) measuring binding of said GPR72 polypeptide to said PUFA, wherein a decrease in binding in the presence of said candidate binding agent, relative to binding in the absence of said candidate binding agent, identifies said candidate binding agent as an agent that binds to GPR72 polypeptide.

2. The method according to claim 1, wherein said PUFA is detectably labeled.

3. The method of claim 2, wherein the label is chosen from the group consisting of a radioisotope, a fluorophore, a quencher of fluorescence, an enzyme, an affinity tag and an epitope tag.

4. The method according to any of claims 1 to 3, wherein said agent is present in a sample.

5. A method of identifying an agent that increases the signaling activity of a GPR72 polypeptide comprising an amino acid sequence selected from the group consisting of SEQ ID NO: 2 and SEQ ID NO:4, wherein said GPR72 polypeptide is capable of binding to a polyunsaturated fatty acid (PUFA), said method comprising:
   (a) contacting said GPR72 polypeptide with an agent;
   (b) measuring a signaling activity of said GPR72 polypeptide in the presence of said agent; and,
   (c) comparing said activity measured in the presence of said agent to the activity measured in a reaction in which said GPR72 polypeptide is contacted with said polyunsaturated fatty acid (PUFA) which binds to the GPR72 polypeptide, wherein said agent is identified as an agonist that increases the signaling of said GPR72 polypeptide when the amount of said activity measured in the presence of said agent is at least 10% of the amount induced by said PUFA.

6. The method according to claim 5, wherein said agent is present in a sample.

7. A method of identifying an agent that decreases the signaling activity of a GPR72 polypeptide comprising an amino acid sequence selected from the group consisting of SEQ ID NO: 2 and SEQ ID NO:4, wherein said GPR72 polypeptide is capable of binding to a polyunsaturated fatty acid (PUFA), said method comprising:
   (a) contacting said GPR72 polypeptide with said polyunsaturated fatty acid (PUFA) which binds to GRP72 polypeptide in the presence or absence of said agent;
   (b) measuring a signaling activity of said GPR72 polypeptide;
   (c) comparing the amount of said activity measured in a reaction containing GPR72 polypeptide and said PUFA without said agent to the amount of said activity measured in a reaction containing said GPR72 polypeptide, said PUFA and said agent, wherein a decrease in said activity in the presence of said agent relative to the activity in the absence of said agent identifies said agent as an antagonist or inverse agonist for said GPR72 polypeptide.

8. The method according to claim 7 wherein said agent is present in a sample.

9. The method according to any one of claims 1, 5 and 7, wherein said GPR72 polypeptide is expressed by cells on their surface.

10. The method according to any one of claims 1, 5 and 7, wherein said GPR72 polypeptide is comprised in cell membranes.

11. The method according to any one of claims 1, 5 and 7, wherein said GPR72 polypeptide is present in or on virus-induced budding membranes.

12. The method according to claim 10 wherein said cells are selected from the group consisting of: COS7-cells, a CHO cell, a LM (TK-) cell, a NIH-3T3 cell, HEK-293 cell, K-562 cell and a 1321N1 astrocytoma cell and other cell lines, or wherein said cell membranes are derived from one of said cell lines.

13. The method according to any one of claims 1, 5 and 7, further performed in the presence of Gα16 polypeptide.

14. The method according to any one of claims 1, 5 and 7, wherein said measuring or said detecting is performed using a method selected from label displacement, surface plasmon resonance, fluorescence resonance energy transfer, fluorescence quenching, and fluorescence polarization.

15. The method according to any one of claims 1, 5 and 7, wherein said agent is selected from the group consisting of a natural or synthetic peptide, a polypeptide, an antibody or antigen-binding fragment thereof, a lipid, a carbohydrate, a nucleic acid, and a small organic molecule.

16. The method according to any one of claims 1, 5 and 7, wherein said detecting or measuring a signaling activity or measuring the binding of said GPR72 polypeptide comprises detecting a change in the level of a second messenger.

17. The method according to any one of claims 1, 5 and 7, wherein the step of detecting or measuring a signaling activity or measuring the binding of said GPR72 polypeptide comprises measurement of guanine nucleotide binding or exchange, adenylate cyclase activity, camp, protein kinase c activity, phosphatidylinositol breakdown, diacylglycerol, inositol trisphosphate, intracellular calcium, arachinoid acid concentration, map kinase activity, tyrosine kinase activity, or, reporter gene expression.

18. The method according to any one of claims 1, 5 and 7, wherein said detecting or measuring a signaling activity comprises using an aequorin-based assay.

19. The method of any one of claims 1, 5 and 7, wherein said PUFA is selected from the group consisting of N Arachidonoly-g-aminobutyric, Arachidonoyl Glycine, Arachidonic Acid, Docosahexaenoic Acid, Eicosapentaenoic Acid, Palmitic acid, 9Z-Palmitoleic acid, Stearic acid, 17-Octadecynoic acid, 6Z-Petroselinic acid, 9E-Elaidic acid, Octadeca-9Z,12Z,15Z-trienoic acid (a-Linolenic acid), Octadeca-6Z,9Z,12Z-trienoic acid (y-Linolenic acid), Nonadecanoic acid, 9-cis-Retinoic acid, All trans retinoic acid,All trans retinal, Eicosanoic acid (Arachidic acid), Eicosa-11Z,14Z-dienoic acid, Eicosa-8Z,11Z,14Z-trienoic acid (Dihomo-y linolenic acid), Eicosa-5Z,8Z,11Z-trienoic acid (Mead acid), Eicosa-5Z,8Z,11Z,14Z-tetraenoic acid (Arachidonic acid), Eicosa-8Z,11Z,14Z,17Z-tetraenoic acid, Arachidonic acid methyl ester, Eicosa-5Z,8Z,11Z,14Z,17Z-pentaenoic acid, Eicosa-8Z,11Z,14Z,17Z-tetraenoic acid, Arachidonic acid methyl ester, Eicosa-5Z,8Z,11Z,14Z,17Z-pentaenoic acid, Heneicosanoic acid, Docosa-13Z-enoic acid, Docosa-13Z,16Z,19Z-trienoic acid, Docosa-7Z,1 OZ,1 3Z,16Z,1 9Z-pentaenoic α Docosa-4Z,7Z,1 OZ,1 3Z,16Z,1 9Z-hexaenoic, and N-arachidonoyl-L-taurine.

\* \* \* \* \*